US012797451B2

(12) United States Patent
Chiarle et al.

(10) Patent No.: US 12,797,451 B2
(45) Date of Patent: Nov. 17, 2026

(54) ANAPLASTIC LYMPHOMA KINASE (ALK) CANCER VACCINE AND METHODS OF USE

(71) Applicant: Children's Medical Center Corporation, Boston, MA (US)

(72) Inventors: Roberto Chiarle, Boston, MA (US); Rafael Blasco-Patino, Boston, MA (US)

(73) Assignee: Children's Medical Center Corporation, Boston, MA (US)

(*) Notice: Subject to any disclaimer, the term of this patent is extended or adjusted under 35 U.S.C. 154(b) by 1119 days.

(21) Appl. No.: 17/761,371

(22) PCT Filed: Sep. 17, 2020

(86) PCT No.: PCT/US2020/051237
§ 371 (c)(1),
(2) Date: Mar. 17, 2022

(87) PCT Pub. No.: WO2021/055580
PCT Pub. Date: Mar. 25, 2021

(65) Prior Publication Data

US 2023/0020894 A1 Jan. 19, 2023

Related U.S. Application Data

(60) Provisional application No. 62/902,096, filed on Sep. 18, 2019.

(51) Int. Cl.
*A61K 39/00* (2006.01)
*A61P 35/00* (2006.01)
*C12N 9/12* (2006.01)

(52) U.S. Cl.
CPC ................. *A61K 39/001162* (2018.08); *A61K 39/001196* (2018.08); *A61P 35/00* (2018.01); *C12N 9/12* (2013.01); *A61K 2039/6093* (2013.01)

(58) Field of Classification Search
CPC .. A61K 2039/55566; A61K 39/001162; A61K 39/001196; A61K 39/39558; A61K 38/00; A61K 31/4439; A61K 2300/00; A61K 2039/86; A61K 2039/6093; A61P 35/00; C07K 16/2818; C12N 9/12; C04B 2235/5445
See application file for complete search history.

(56) References Cited

U.S. PATENT DOCUMENTS

| | | | | |
|---|---|---|---|---|
| 8,980,287 B2 * | 3/2015 | Chiarle | A61P 31/00 514/19.2 | |
| 9,650,614 B2 * | 5/2017 | Chiarle | A61K 39/001162 | |
| 10,317,402 B2 * | 6/2019 | Parenteau | G01N 33/574 | |
| 11,016,091 B2 * | 5/2021 | Parenteau | A61K 35/17 | |
| 2003/0157101 A1 | 8/2003 | Gambacorti-Passerini et al. | | |
| 2016/0161486 A1 * | 6/2016 | Parenteau | G01N 33/574 435/6.12 | |
| 2023/0101046 A1 | 3/2023 | Chiarle et al. | | |
| 2025/0057930 A1 | 2/2025 | Chiarle et al. | | |

FOREIGN PATENT DOCUMENTS

| | | | |
|---|---|---|---|
| WO | 2016090177 A1 | 6/2016 | |
| WO | WO2016090177 A * | 6/2016 | G01N 33/50 |
| WO | 2017132555 A1 | 8/2017 | |

OTHER PUBLICATIONS

Chen et al. Immunol Res. 2012, vol. 53, pp. 182-190.*
International Search Report and Written Opinion mailed Mar. 12, 2021 in corresponding PCT Patent Application No. PCT/US2020/051237 (14 pages).
Extended European Search Report received in corresponding European Application No. 24186643.3, dated Feb. 4, 2025, (10 pages).
Awad et al., "Epitope mapping of spontaneous autoantibodies to anaplastic lymphoma kinase (ALK) in non-small cell lung cancer," Oncotarget, 2017, vol. 8, No. 54, pp. 92265-92274.
Mota et al., "ALK peptide vaccination restores the immunogenicity of ALK-rearranged non-small cell lung cancer," Nature Cancer, Jul. 2023, vol. 4, pp. 1016-1035.
Partial Supplementary European Search Report dated Sep. 11, 2023 in corresponding European Patent Application No. 20864504.4 (16 pages).
Abelin et al., "Mass Spectrometry Profiling of HLA-Associated Peptidomes in Mono-allelic Cells Enables More Accurate Epitope Prediction," Immunity, Feb. 21, 2017, vol. 46, pp. 315-326.
GenBank Accession No. AAA58698.1, downloaded Nov. 3, 2022 (2 pages).
GenBank Accession No. AB274722.1, downloaded Nov. 3, 2022 (3 pages).

(Continued)

*Primary Examiner* — Bao Q Li
(74) *Attorney, Agent, or Firm* — Greenberg Traurig, LLP; Melissa Hunter-Ensor; Leslie Serunian

(57) ABSTRACT

Provided herein are isolated anaplastic lymphoma kinase (ALK) peptides that are fragments of the cytoplasmic portion of an ALK protein shared by cancers having an ALK rearrangement and cancers expressing the ALK protein, that bind a human leukocyte antigen (HLA), and elicit an immune response against one or more ALK-positive cancers. Also provided are isolated ALK peptides that are modified with an amphiphilic conjugate to increase T-cell expansion and greatly enhance anti-tumor efficacy. The invention also provides polynucleotides encoding isolated ALK peptides, vaccines comprising an isolated ALK peptide or polynucleotide, immunogenic compositions thereof, and kits for administering the same. Methods of treatment and methods of generating an immune response in a subject by administering the ALK-specific peptide antigens, immunogens, vaccines, or immunogenic compositions thereof are provided.

15 Claims, 18 Drawing Sheets

Specification includes a Sequence Listing.

(56) References Cited

OTHER PUBLICATIONS

GenBank Accession No. ACI47591, downloaded Nov. 3, 2022 (2 pages).
GenBank Accession No. ACY79563, downloaded Nov. 3, 2022 (2 pages).
GenBank Accession No. BAD92714.1, downloaded Nov. 3, 2022 (2 pages).
GenBank Accession No. BAF73611.1, downloaded Nov. 3, 2022 (2 pages).
GenBank Accession No. BAM37627.1, downloaded Nov. 3, 2022 (2 pages).
Lin et al., "Impact of EML4-ALK Variant on Resistance Mechanisms and Clinical Outcomes in ALK-Positive Lung Cancer," Journal of Clinical Oncology, Apr. 20, 2018, vol. 36, No. 12, pp. 1199-1206.
Liu et al., "Structure-based Programming of Lymph Node Targeting in Molecular Vaccines," Nature, Mar. 27, 2014, vol. 507, No. 7493, pp. 519-522.
Shimizu et al., "Production of human cells expressing individual transferred HLA-A,-B,-C genes using an HLA-A,-B,-C null human cell line," The Journal of Immunology, May 1, 1989, vol. 142, No. 9, pp. 3320-3328.
Extended European Search Report dated Dec. 12, 2023 in corresponding European Patent Application No. 20864504.4 (14 pages).
Office Action dated Jan. 8, 2024 in corresponding European Patent Application No. 20864504.4 (1 page).
Office Action dated May 6, 2026, in corresponding Australian Patent Application No. 2020351168 (6 pages).
Communication pursuant to Article 94(3) mailed in corresponding European Application No. 24186643.3, dated Jan. 13, 2026, (6 pages).

* cited by examiner

| peptide | allele | length | msec |
|---|---|---|---|
| **IVRCIGVSL** | **B0702** | **9** | **0.718** |
| IVRCIGVSL | C1203 | 9 | 0.447 |
| IVRCIGVSL | C0802 | 9 | 0.251 |
| **IVRCIGVSL** | **C0401** | **9** | **0.209** |
| IVRCIGVSL | C0602 | 9 | 0.206 |
| **IVRCIGVSL** | **B3501** | **9** | **0.197** |
| IVRCIGVSL | A0201 | 9 | 0.113 |
| **IVRCIGVSL** | **A0301** | **9** | **0.097** |
| **IVRCIGVSL** | **C0702** | **9** | **0.095** |

| peptide | allele | length | msec |
|---|---|---|---|
| **RPRPSQPSSL** | **B0702** | **10** | **0.922** |
| **RPRPSQPSSL** | **A0301** | **10** | **0.368** |
| **RPRPSQPSSL** | **C0702** | **10** | **0.322** |
| **RPRPSQPSSL** | **B3501** | **10** | **0.321** |
| RPRPSQPSSL | C1203 | 10 | 0.190 |
| RPRPSQPSSL | C0802 | 10 | 0.189 |
| **RPRPSQPSSL** | **C0401** | **10** | **0.073** |
| RPRPSQPSSL | A0201 | 10 | 0.054 |
| RPRPSQPSSL | C0602 | 10 | 0.047 |

| peptide | allele | length | msec |
|---|---|---|---|
| **VPRKNITLI** | **B0702** | **9** | **0.914** |
| **VPRKNITLI** | **B3501** | **9** | **0.327** |
| VPRKNITLI | C0602 | 9 | 0.199 |
| VPRKNITLI | C1203 | 9 | 0.082 |
| VPRKNITLI | A0201 | 9 | 0.047 |
| **VPRKNITLI** | **C0401** | **9** | **0.041** |
| **VPRKNITLI** | **C0702** | **9** | **0.018** |
| VPRKNITLI | C0802 | 9 | 0.012 |
| **VPRKNITLI** | **A0301** | **9** | **0.007** |

SEQUENCE LISTING

```
<160> NUMBER OF SEQ ID NOS: 89

<210> SEQ ID NO 1
<211> LENGTH: 9
<212> TYPE: PRT
<213> ORGANISM: Homo sapiens

<400> SEQUENCE: 1

Ala Met Leu Asp Leu Leu His Val Ala
1               5


<210> SEQ ID NO 2
<211> LENGTH: 10
<212> TYPE: PRT
<213> ORGANISM: Homo sapiens

<400> SEQUENCE: 2

Arg Pro Arg Pro Ser Gln Pro Ser Ser Leu
1               5                   10


<210> SEQ ID NO 3
<211> LENGTH: 9
<212> TYPE: PRT
<213> ORGANISM: Homo sapiens

<400> SEQUENCE: 3

Ile Val Arg Cys Ile Gly Val Ser Leu
```

1 5

<210> SEQ ID NO 4
<211> LENGTH: 9
<212> TYPE: PRT
<213> ORGANISM: Homo sapiens

<400> SEQUENCE: 4

Val Pro Arg Lys Asn Ile Thr Leu Ile
1 5

<210> SEQ ID NO 5
<211> LENGTH: 9
<212> TYPE: PRT
<213> ORGANISM: Homo sapiens

<400> SEQUENCE: 5

Thr Ala Ala Glu Val Ser Val Arg Val
1 5

<210> SEQ ID NO 6
<211> LENGTH: 1626
<212> TYPE: PRT
<213> ORGANISM: Homo sapiens

<400> SEQUENCE: 6

Thr Ala Ser Ser Gly Gly Met Gly Ala Ile Gly Leu Leu Trp Leu Leu
1 5 10 15

Pro Leu Leu Leu Ser Thr Ala Ala Val Gly Ser Gly Met Gly Thr Gly
20 25 30

Gln Arg Ala Gly Ser Pro Ala Ala Gly Pro Pro Leu Gln Pro Arg Glu
35 40 45

Pro Leu Ser Tyr Ser Arg Leu Gln Arg Lys Ser Leu Ala Val Asp Phe
50 55 60

Val Val Pro Ser Leu Phe Arg Val Tyr Ala Arg Asp Leu Leu Leu Pro
65 70 75 80

Pro Ser Ser Ser Glu Leu Lys Ala Gly Arg Pro Glu Ala Arg Gly Ser
85 90 95

Leu Ala Leu Asp Cys Ala Pro Leu Leu Arg Leu Leu Gly Pro Ala Pro
100 105 110

Gly Val Ser Trp Thr Ala Gly Ser Pro Ala Pro Ala Glu Ala Arg Thr
115 120 125

Leu Ser Arg Val Leu Lys Gly Gly Ser Val Arg Lys Leu Arg Arg Ala
130 135 140

Lys Gln Leu Val Leu Glu Leu Gly Glu Glu Ala Ile Leu Glu Gly Cys
145 150 155 160

Val Gly Pro Pro Gly Glu Ala Ala Val Gly Leu Leu Gln Phe Asn Leu
165 170 175

Ser Glu Leu Phe Ser Trp Trp Ile Arg Gln Gly Glu Gly Arg Leu Arg
180 185 190

Ile Arg Leu Met Pro Glu Lys Lys Ala Ser Glu Val Gly Arg Glu Gly
195 200 205

Arg Leu Ser Ala Ala Ile Arg Ala Ser Gln Pro Arg Leu Leu Phe Gln
210 215 220

Ile Phe Gly Thr Gly His Ser Ser Leu Glu Ser Pro Thr Asn Met Pro
225 230 235 240

Ser Pro Ser Pro Asp Tyr Phe Thr Trp Asn Leu Thr Trp Ile Met Lys
245 250 255

```
Asp Ser Phe Pro Phe Leu Ser His Arg Ser Arg Tyr Gly Leu Glu Cys
            260                 265                 270

Ser Phe Asp Phe Pro Cys Glu Leu Glu Tyr Ser Pro Pro Leu His Asp
        275                 280                 285

Leu Arg Asn Gln Ser Trp Ser Trp Arg Arg Ile Pro Ser Glu Glu Ala
    290                 295                 300

Ser Gln Met Asp Leu Leu Asp Gly Pro Gly Ala Glu Arg Ser Lys Glu
305                 310                 315                 320

Met Pro Arg Gly Ser Phe Leu Leu Leu Asn Thr Ser Ala Asp Ser Lys
                325                 330                 335

His Thr Ile Leu Ser Pro Trp Met Arg Ser Ser Ser Glu His Cys Thr
            340                 345                 350

Leu Ala Val Ser Val His Arg His Leu Gln Pro Ser Gly Arg Tyr Ile
        355                 360                 365

Ala Gln Leu Leu Pro His Asn Glu Ala Ala Arg Glu Ile Leu Leu Met
    370                 375                 380

Pro Thr Pro Gly Lys His Gly Trp Thr Val Leu Gln Gly Arg Ile Gly
385                 390                 395                 400

Arg Pro Asp Asn Pro Phe Arg Val Ala Leu Glu Tyr Ile Ser Ser Gly
                405                 410                 415

Asn Arg Ser Leu Ser Ala Val Asp Phe Phe Ala Leu Lys Asn Cys Ser
            420                 425                 430

Glu Gly Thr Ser Pro Gly Ser Lys Met Ala Leu Gln Ser Ser Phe Thr
        435                 440                 445

Cys Trp Asn Gly Thr Val Leu Gln Leu Gly Gln Ala Cys Asp Phe His
    450                 455                 460

Gln Asp Cys Ala Gln Gly Glu Asp Glu Ser Gln Met Cys Arg Lys Leu
465                 470                 475                 480

Pro Val Gly Phe Tyr Cys Asn Phe Glu Asp Gly Phe Cys Gly Trp Thr
                485                 490                 495

Gln Gly Thr Leu Ser Pro His Thr Pro Gln Trp Gln Val Arg Thr Leu
            500                 505                 510

Lys Asp Ala Arg Phe Gln Asp His Gln Asp His Ala Leu Leu Leu Ser
        515                 520                 525

Thr Thr Asp Val Pro Ala Ser Glu Ser Ala Thr Val Thr Ser Ala Thr
    530                 535                 540

Phe Pro Ala Pro Ile Lys Ser Ser Pro Cys Glu Leu Arg Met Ser Trp
545                 550                 555                 560

Leu Ile Arg Gly Val Leu Arg Gly Asn Val Ser Leu Val Leu Val Glu
                565                 570                 575

Asn Lys Thr Gly Lys Glu Gln Gly Arg Met Val Trp His Val Ala Ala
            580                 585                 590

Tyr Glu Gly Leu Ser Leu Trp Gln Trp Met Val Leu Pro Leu Leu Asp
        595                 600                 605

Val Ser Asp Arg Phe Trp Leu Gln Met Val Ala Trp Trp Gly Gln Gly
    610                 615                 620

Ser Arg Ala Ile Val Ala Phe Asp Asn Ile Ser Ile Ser Leu Asp Cys
625                 630                 635                 640

Tyr Leu Thr Ile Ser Gly Glu Asp Lys Ile Leu Gln Asn Thr Ala Pro
                645                 650                 655

Lys Ser Arg Asn Leu Phe Glu Arg Asn Pro Asn Lys Glu Leu Lys Pro
            660                 665                 670
```

```
Gly Glu Asn Ser Pro Arg Gln Thr Pro Ile Phe Asp Pro Thr Val His
        675                 680                 685

Trp Leu Phe Thr Thr Cys Gly Ala Ser Gly Pro His Gly Pro Thr Gln
    690                 695                 700

Ala Gln Cys Asn Asn Ala Tyr Gln Asn Ser Asn Leu Ser Val Glu Val
705                 710                 715                 720

Gly Ser Glu Gly Pro Leu Lys Gly Ile Gln Ile Trp Lys Val Pro Ala
                725                 730                 735

Thr Asp Thr Tyr Ser Ile Ser Gly Tyr Gly Ala Ala Gly Gly Lys Gly
            740                 745                 750

Gly Lys Asn Thr Met Met Arg Ser His Gly Val Ser Val Leu Gly Ile
        755                 760                 765

Phe Asn Leu Glu Lys Asp Asp Met Leu Tyr Ile Leu Val Gly Gln Gln
    770                 775                 780

Gly Glu Asp Ala Cys Pro Ser Thr Asn Gln Leu Ile Gln Lys Val Cys
785                 790                 795                 800

Ile Gly Glu Asn Asn Val Ile Glu Glu Glu Ile Arg Val Asn Arg Ser
                805                 810                 815

Val His Glu Trp Ala Gly Gly Gly Gly Gly Gly Gly Gly Ala Thr Tyr
            820                 825                 830

Val Phe Lys Met Lys Asp Gly Val Pro Val Pro Leu Ile Ile Ala Ala
        835                 840                 845

Gly Gly Gly Gly Arg Ala Tyr Gly Ala Lys Thr Asp Thr Phe His Pro
    850                 855                 860

Glu Arg Leu Glu Asn Asn Ser Ser Val Leu Gly Leu Asn Gly Asn Ser
865                 870                 875                 880

Gly Ala Ala Gly Gly Gly Gly Gly Trp Asn Asp Asn Thr Ser Leu Leu
                885                 890                 895

Trp Ala Gly Lys Ser Leu Gln Glu Gly Ala Thr Gly Gly His Ser Cys
            900                 905                 910

Pro Gln Ala Met Lys Lys Trp Gly Trp Glu Thr Arg Gly Gly Phe Gly
        915                 920                 925

Gly Gly Gly Gly Gly Cys Ser Ser Gly Gly Gly Gly Gly Gly Tyr Ile
    930                 935                 940

Gly Gly Asn Ala Ala Ser Asn Asn Asp Pro Glu Met Asp Gly Glu Asp
945                 950                 955                 960

Gly Val Ser Phe Ile Ser Pro Leu Gly Ile Leu Tyr Thr Pro Ala Leu
                965                 970                 975

Lys Val Met Glu Gly His Gly Glu Val Asn Ile Lys His Tyr Leu Asn
            980                 985                 990

Cys Ser His Cys Glu Val Asp Glu  Cys His Met Asp Pro  Glu Ser His
        995                 1000                1005

Lys Val  Ile Cys Phe Cys Asp  His Gly Thr Val Leu  Ala Glu Asp
    1010                1015                1020

Gly Val  Ser Cys Ile Val Ser  Pro Thr Pro Glu Pro  His Leu Pro
    1025                1030                1035

Leu Ser  Leu Ile Leu Ser Val  Val Thr Ser Ala Leu  Val Ala Ala
    1040                1045                1050

Leu Val  Leu Ala Phe Ser Gly  Ile Met Ile Val Tyr  Arg Arg Lys
    1055                1060                1065

His Gln  Glu Leu Gln Ala Met  Gln Met Glu Leu Gln  Ser Pro Glu
    1070                1075                1080

Tyr Lys  Leu Ser Lys Leu Arg  Thr Ser Thr Ile Met  Thr Asp Tyr
```

```
    1085                1090                1095

Asn Pro  Asn Tyr Cys Phe Ala  Gly Lys Thr Ser Ser  Ile Ser Asp
    1100                1105                1110

Leu Lys  Glu Val Pro Arg Lys  Asn Ile Thr Leu Ile  Arg Gly Leu
    1115                1120                1125

Gly His  Gly Ala Phe Gly Glu  Val Tyr Glu Gly Gln  Val Ser Gly
    1130                1135                1140

Met Pro  Asn Asp Pro Ser Pro  Leu Gln Val Ala Val  Lys Thr Leu
    1145                1150                1155

Pro Glu  Val Cys Ser Glu Gln  Asp Glu Leu Asp Phe  Leu Met Glu
    1160                1165                1170

Ala Leu  Ile Ile Ser Lys Phe  Asn His Gln Asn Ile  Val Arg Cys
    1175                1180                1185

Ile Gly  Val Ser Leu Gln Ser  Leu Pro Arg Phe Ile  Leu Leu Glu
    1190                1195                1200

Leu Met  Ala Gly Gly Asp Leu  Lys Ser Phe Leu Arg  Glu Thr Arg
    1205                1210                1215

Pro Arg  Pro Ser Gln Pro Ser  Ser Leu Ala Met Leu  Asp Leu Leu
    1220                1225                1230

His Val  Ala Arg Asp Ile Ala  Cys Gly Cys Gln Tyr  Leu Glu Glu
    1235                1240                1245

Asn His  Phe Ile His Arg Asp  Ile Ala Ala Arg Asn  Cys Leu Leu
    1250                1255                1260

Thr Cys  Pro Gly Pro Gly Arg  Val Ala Lys Ile Gly  Asp Phe Gly
    1265                1270                1275

Met Ala  Arg Asp Ile Tyr Arg  Ala Ser Tyr Tyr Arg  Lys Gly Gly
    1280                1285                1290

Cys Ala  Met Leu Pro Val Lys  Trp Met Pro Pro Glu  Ala Phe Met
    1295                1300                1305

Glu Gly  Ile Phe Thr Ser Lys  Thr Asp Thr Trp Ser  Phe Gly Val
    1310                1315                1320

Leu Leu  Trp Glu Ile Phe Ser  Leu Gly Tyr Met Pro  Tyr Pro Ser
    1325                1330                1335

Lys Ser  Asn Gln Glu Val Leu  Glu Phe Val Thr Ser  Gly Gly Arg
    1340                1345                1350

Met Asp  Pro Pro Lys Asn Cys  Pro Gly Pro Val Tyr  Arg Ile Met
    1355                1360                1365

Thr Gln  Cys Trp Gln His Gln  Pro Glu Asp Arg Pro  Asn Phe Ala
    1370                1375                1380

Ile Ile  Leu Glu Arg Ile Glu  Tyr Cys Thr Gln Asp  Pro Asp Val
    1385                1390                1395

Ile Asn  Thr Ala Leu Pro Ile  Glu Tyr Gly Pro Leu  Val Glu Glu
    1400                1405                1410

Glu Glu  Lys Val Pro Val Arg  Pro Lys Asp Pro Glu  Gly Val Pro
    1415                1420                1425

Pro Leu  Leu Val Ser Gln Gln  Ala Lys Arg Glu Glu  Glu Arg Ser
    1430                1435                1440

Pro Ala  Ala Pro Pro Pro Leu  Pro Thr Thr Ser Ser  Gly Lys Ala
    1445                1450                1455

Ala Lys  Lys Pro Thr Ala Ala  Glu Ile Ser Val Arg  Val Pro Arg
    1460                1465                1470

Gly Pro  Ala Val Glu Gly Gly  His Val Asn Met Ala  Phe Ser Gln
    1475                1480                1485
```

```
Ser Asn  Pro Pro Ser Glu Leu  His Lys Val His Gly  Ser Arg Asn
    1490                 1495                 1500

Lys Pro  Thr Ser Leu Trp Asn  Pro Thr Tyr Gly Ser  Trp Phe Thr
    1505                 1510                 1515

Glu Lys  Pro Thr Lys Lys Asn  Asn Pro Ile Ala Lys  Lys Glu Pro
    1520                 1525                 1530

His Asp  Arg Gly Asn Leu Gly  Leu Glu Gly Ser Cys  Thr Val Pro
    1535                 1540                 1545

Pro Asn  Val Ala Thr Gly Arg  Leu Pro Gly Ala Ser  Leu Leu Leu
    1550                 1555                 1560

Glu Pro  Ser Ser Leu Thr Ala  Asn Met Lys Glu Val  Pro Leu Phe
    1565                 1570                 1575

Arg Leu  Arg His Phe Pro Cys  Gly Asn Val Asn Tyr  Gly Tyr Gln
    1580                 1585                 1590

Gln Gln  Gly Leu Pro Leu Glu  Ala Ala Thr Ala Pro  Gly Ala Gly
    1595                 1600                 1605

His Tyr  Glu Asp Thr Ile Leu  Lys Ser Lys Asn Ser  Met Asn Gln
    1610                 1615                 1620

Pro Gly  Pro
    1625


<210> SEQ ID NO 7
<211> LENGTH: 38
<212> TYPE: PRT
<213> ORGANISM: Homo sapiens

<400> SEQUENCE: 7

Gly Ala Ala Ala Val Val Ala Ala Gly Thr Ser Arg Arg Leu Cys Ser
1               5                   10                  15

Glu Gly Arg Gly Ala Pro Arg Cys Phe Pro Ala Ala Leu Trp Ser Ala
            20                  25                  30

Thr Gln Ser Arg Gly Arg
        35


<210> SEQ ID NO 8
<211> LENGTH: 1620
<212> TYPE: PRT
<213> ORGANISM: Homo sapiens

<400> SEQUENCE: 8

Met Gly Ala Ile Gly Leu Leu Trp Leu Leu Pro Leu Leu Leu Ser Thr
1               5                   10                  15

Ala Ala Val Gly Ser Gly Met Gly Thr Gly Gln Arg Ala Gly Ser Pro
            20                  25                  30

Ala Ala Gly Pro Pro Leu Gln Pro Arg Glu Pro Leu Ser Tyr Ser Arg
        35                  40                  45

Leu Gln Arg Lys Ser Leu Ala Val Asp Phe Val Val Pro Ser Leu Phe
    50                  55                  60

Arg Val Tyr Ala Arg Asp Leu Leu Leu Pro Pro Ser Ser Ser Glu Leu
65                  70                  75                  80

Lys Ala Gly Arg Pro Glu Ala Arg Gly Ser Leu Ala Leu Asp Cys Ala
                85                  90                  95

Pro Leu Leu Arg Leu Leu Gly Pro Ala Pro Gly Val Ser Trp Thr Ala
            100                 105                 110

Gly Ser Pro Ala Pro Ala Glu Ala Arg Thr Leu Ser Arg Val Leu Lys
        115                 120                 125
```

```
Gly Gly Ser Val Arg Lys Leu Arg Arg Ala Lys Gln Leu Val Leu Glu
    130                 135                 140

Leu Gly Glu Glu Ala Ile Leu Glu Gly Cys Val Gly Pro Pro Gly Glu
145                 150                 155                 160

Ala Ala Val Gly Leu Leu Gln Phe Asn Leu Ser Glu Leu Phe Ser Trp
                165                 170                 175

Trp Ile Arg Gln Gly Glu Gly Arg Leu Arg Ile Arg Leu Met Pro Glu
            180                 185                 190

Lys Lys Ala Ser Glu Val Gly Arg Glu Gly Arg Leu Ser Ala Ala Ile
        195                 200                 205

Arg Ala Ser Gln Pro Arg Leu Leu Phe Gln Ile Phe Gly Thr Gly His
    210                 215                 220

Ser Ser Leu Glu Ser Pro Thr Asn Met Pro Ser Pro Ser Pro Asp Tyr
225                 230                 235                 240

Phe Thr Trp Asn Leu Thr Trp Ile Met Lys Asp Ser Phe Pro Phe Leu
                245                 250                 255

Ser His Arg Ser Arg Tyr Gly Leu Glu Cys Ser Phe Asp Phe Pro Cys
            260                 265                 270

Glu Leu Glu Tyr Ser Pro Pro Leu His Asp Leu Arg Asn Gln Ser Trp
        275                 280                 285

Ser Trp Arg Arg Ile Pro Ser Glu Glu Ala Ser Gln Met Asp Leu Leu
    290                 295                 300

Asp Gly Pro Gly Ala Glu Arg Ser Lys Glu Met Pro Arg Gly Ser Phe
305                 310                 315                 320

Leu Leu Leu Asn Thr Ser Ala Asp Ser Lys His Thr Ile Leu Ser Pro
                325                 330                 335

Trp Met Arg Ser Ser Ser Glu His Cys Thr Leu Ala Val Ser Val His
            340                 345                 350

Arg His Leu Gln Pro Ser Gly Arg Tyr Ile Ala Gln Leu Leu Pro His
        355                 360                 365

Asn Glu Ala Ala Arg Glu Ile Leu Leu Met Pro Thr Pro Gly Lys His
    370                 375                 380

Gly Trp Thr Val Leu Gln Gly Arg Ile Gly Arg Pro Asp Asn Pro Phe
385                 390                 395                 400

Arg Val Ala Leu Glu Tyr Ile Ser Ser Gly Asn Arg Ser Leu Ser Ala
                405                 410                 415

Val Asp Phe Phe Ala Leu Lys Asn Cys Ser Glu Gly Thr Ser Pro Gly
            420                 425                 430

Ser Lys Met Ala Leu Gln Ser Ser Phe Thr Cys Trp Asn Gly Thr Val
        435                 440                 445

Leu Gln Leu Gly Gln Ala Cys Asp Phe His Gln Asp Cys Ala Gln Gly
    450                 455                 460

Glu Asp Glu Ser Gln Met Cys Arg Lys Leu Pro Val Gly Phe Tyr Cys
465                 470                 475                 480

Asn Phe Glu Asp Gly Phe Cys Gly Trp Thr Gln Gly Thr Leu Ser Pro
                485                 490                 495

His Thr Pro Gln Trp Gln Val Arg Thr Leu Lys Asp Ala Arg Phe Gln
            500                 505                 510

Asp His Gln Asp His Ala Leu Leu Leu Ser Thr Thr Asp Val Pro Ala
        515                 520                 525

Ser Glu Ser Ala Thr Val Thr Ser Ala Thr Phe Pro Ala Pro Ile Lys
    530                 535                 540
```

Ser Ser Pro Cys Glu Leu Arg Met Ser Trp Leu Ile Arg Gly Val Leu
545 550 555 560

Arg Gly Asn Val Ser Leu Val Leu Val Glu Asn Lys Thr Gly Lys Glu
565 570 575

Gln Gly Arg Met Val Trp His Val Ala Ala Tyr Glu Gly Leu Ser Leu
580 585 590

Trp Gln Trp Met Val Leu Pro Leu Leu Asp Val Ser Asp Arg Phe Trp
595 600 605

Leu Gln Met Val Ala Trp Trp Gly Gln Gly Ser Arg Ala Ile Val Ala
610 615 620

Phe Asp Asn Ile Ser Ile Ser Leu Asp Cys Tyr Leu Thr Ile Ser Gly
625 630 635 640

Glu Asp Lys Ile Leu Gln Asn Thr Ala Pro Lys Ser Arg Asn Leu Phe
645 650 655

Glu Arg Asn Pro Asn Lys Glu Leu Lys Pro Gly Glu Asn Ser Pro Arg
660 665 670

Gln Thr Pro Ile Phe Asp Pro Thr Val His Trp Leu Phe Thr Thr Cys
675 680 685

Gly Ala Ser Gly Pro His Gly Pro Thr Gln Ala Gln Cys Asn Asn Ala
690 695 700

Tyr Gln Asn Ser Asn Leu Ser Val Glu Val Gly Ser Glu Gly Pro Leu
705 710 715 720

Lys Gly Ile Gln Ile Trp Lys Val Pro Ala Thr Asp Thr Tyr Ser Ile
725 730 735

Ser Gly Tyr Gly Ala Ala Gly Gly Lys Gly Gly Lys Asn Thr Met Met
740 745 750

Arg Ser His Gly Val Ser Val Leu Gly Ile Phe Asn Leu Glu Lys Asp
755 760 765

Asp Met Leu Tyr Ile Leu Val Gly Gln Gln Gly Glu Asp Ala Cys Pro
770 775 780

Ser Thr Asn Gln Leu Ile Gln Lys Val Cys Ile Gly Glu Asn Asn Val
785 790 795 800

Ile Glu Glu Glu Ile Arg Val Asn Arg Ser Val His Glu Trp Ala Gly
805 810 815

Gly Gly Gly Gly Gly Gly Gly Ala Thr Tyr Val Phe Lys Met Lys Asp
820 825 830

Gly Val Pro Val Pro Leu Ile Ile Ala Ala Gly Gly Gly Gly Arg Ala
835 840 845

Tyr Gly Ala Lys Thr Asp Thr Phe His Pro Glu Arg Leu Glu Asn Asn
850 855 860

Ser Ser Val Leu Gly Leu Asn Gly Asn Ser Gly Ala Ala Gly Gly Gly
865 870 875 880

Gly Gly Trp Asn Asp Asn Thr Ser Leu Leu Trp Ala Gly Lys Ser Leu
885 890 895

Gln Glu Gly Ala Thr Gly Gly His Ser Cys Pro Gln Ala Met Lys Lys
900 905 910

Trp Gly Trp Glu Thr Arg Gly Gly Phe Gly Gly Gly Gly Gly Gly Cys
915 920 925

Ser Ser Gly Gly Gly Gly Gly Gly Tyr Ile Gly Gly Asn Ala Ala Ser
930 935 940

Asn Asn Asp Pro Glu Met Asp Gly Glu Asp Gly Val Ser Phe Ile Ser
945 950 955 960

Pro Leu Gly Ile Leu Tyr Thr Pro Ala Leu Lys Val Met Glu Gly His

-continued

```
                965                 970                 975

Gly Glu Val Asn Ile Lys His Tyr Leu Asn Cys Ser His Cys Glu Val
            980                 985                 990

Asp Glu Cys His Met Asp Pro Glu  Ser His Lys Val Ile  Cys Phe Cys
        995                 1000                1005

Asp His  Gly Thr Val Leu Ala  Glu Asp Gly Val Ser  Cys Ile Val
    1010                1015                1020

Ser Pro  Thr Pro Glu Pro His  Leu Pro Leu Ser Leu  Ile Leu Ser
    1025                1030                1035

Val Val  Thr Ser Ala Leu Val  Ala Ala Leu Val Leu  Ala Phe Ser
    1040                1045                1050

Gly Ile  Met Ile Val Tyr Arg  Arg Lys His Gln Glu  Leu Gln Ala
    1055                1060                1065

Met Gln  Met Glu Leu Gln Ser  Pro Glu Tyr Lys Leu  Ser Lys Leu
    1070                1075                1080

Arg Thr  Ser Thr Ile Met Thr  Asp Tyr Asn Pro Asn  Tyr Cys Phe
    1085                1090                1095

Ala Gly  Lys Thr Ser Ser Ile  Ser Asp Leu Lys Glu  Val Pro Arg
    1100                1105                1110

Lys Asn  Ile Thr Leu Ile Arg  Gly Leu Gly His Gly  Ala Phe Gly
    1115                1120                1125

Glu Val  Tyr Glu Gly Gln Val  Ser Gly Met Pro Asn  Asp Pro Ser
    1130                1135                1140

Pro Leu  Gln Val Ala Val Lys  Thr Leu Pro Glu Val  Cys Ser Glu
    1145                1150                1155

Gln Asp  Glu Leu Asp Phe Leu  Met Glu Ala Leu Ile  Ile Ser Lys
    1160                1165                1170

Phe Asn  His Gln Asn Ile Val  Arg Cys Ile Gly Val  Ser Leu Gln
    1175                1180                1185

Ser Leu  Pro Arg Phe Ile Leu  Leu Glu Leu Met Ala  Gly Gly Asp
    1190                1195                1200

Leu Lys  Ser Phe Leu Arg Glu  Thr Arg Pro Arg Pro  Ser Gln Pro
    1205                1210                1215

Ser Ser  Leu Ala Met Leu Asp  Leu Leu His Val Ala  Arg Asp Ile
    1220                1225                1230

Ala Cys  Gly Cys Gln Tyr Leu  Glu Glu Asn His Phe  Ile His Arg
    1235                1240                1245

Asp Ile  Ala Ala Arg Asn Cys  Leu Leu Thr Cys Pro  Gly Pro Gly
    1250                1255                1260

Arg Val  Ala Lys Ile Gly Asp  Phe Gly Met Ala Arg  Asp Ile Tyr
    1265                1270                1275

Arg Ala  Ser Tyr Tyr Arg Lys  Gly Gly Cys Ala Met  Leu Pro Val
    1280                1285                1290

Lys Trp  Met Pro Pro Glu Ala  Phe Met Glu Gly Ile  Phe Thr Ser
    1295                1300                1305

Lys Thr  Asp Thr Trp Ser Phe  Gly Val Leu Leu Trp  Glu Ile Phe
    1310                1315                1320

Ser Leu  Gly Tyr Met Pro Tyr  Pro Ser Lys Ser Asn  Gln Glu Val
    1325                1330                1335

Leu Glu  Phe Val Thr Ser Gly  Gly Arg Met Asp Pro  Pro Lys Asn
    1340                1345                1350

Cys Pro  Gly Pro Val Tyr Arg  Ile Met Thr Gln Cys  Trp Gln His
    1355                1360                1365
```

```
Gln Pro  Glu Asp Arg Pro Asn  Phe Ala Ile Ile Leu  Glu Arg Ile
    1370                 1375                 1380

Glu Tyr  Cys Thr Gln Asp Pro  Asp Val Ile Asn Thr  Ala Leu Pro
    1385                 1390                 1395

Ile Glu  Tyr Gly Pro Leu Val  Glu Glu Glu Glu Lys  Val Pro Val
    1400                 1405                 1410

Arg Pro  Lys Asp Pro Glu Gly  Val Pro Pro Leu Leu  Val Ser Gln
    1415                 1420                 1425

Gln Ala  Lys Arg Glu Glu Glu  Arg Ser Pro Ala Ala  Pro Pro Pro
    1430                 1435                 1440

Leu Pro  Thr Thr Ser Ser Gly  Lys Ala Ala Lys Lys  Pro Thr Ala
    1445                 1450                 1455

Ala Glu  Ile Ser Val Arg Val  Pro Arg Gly Pro Ala  Val Glu Gly
    1460                 1465                 1470

Gly His  Val Asn Met Ala Phe  Ser Gln Ser Asn Pro  Pro Ser Glu
    1475                 1480                 1485

Leu His  Lys Val His Gly Ser  Arg Asn Lys Pro Thr  Ser Leu Trp
    1490                 1495                 1500

Asn Pro  Thr Tyr Gly Ser Trp  Phe Thr Glu Lys Pro  Thr Lys Lys
    1505                 1510                 1515

Asn Asn  Pro Ile Ala Lys Lys  Glu Pro His Asp Arg  Gly Asn Leu
    1520                 1525                 1530

Gly Leu  Glu Gly Ser Cys Thr  Val Pro Pro Asn Val  Ala Thr Gly
    1535                 1540                 1545

Arg Leu  Pro Gly Ala Ser Leu  Leu Leu Glu Pro Ser  Ser Leu Thr
    1550                 1555                 1560

Ala Asn  Met Lys Glu Val Pro  Leu Phe Arg Leu Arg  His Phe Pro
    1565                 1570                 1575

Cys Gly  Asn Val Asn Tyr Gly  Tyr Gln Gln Gln Gly  Leu Pro Leu
    1580                 1585                 1590

Glu Ala  Ala Thr Ala Pro Gly  Ala Gly His Tyr Glu  Asp Thr Ile
    1595                 1600                 1605

Leu Lys  Ser Lys Asn Ser Met  Asn Gln Pro Gly Pro
    1610                 1615                 1620


<210> SEQ ID NO 9
<211> LENGTH: 6221
<212> TYPE: DNA
<213> ORGANISM: Homo sapiens

<400> SEQUENCE: 9

ggggcggcag cggtggtagc agctggtacc tcccgccgcc tctgttcgga gggtcgcggg      60

gcaccgaggt gctttccggc cgccctctgg tcggccaccc aaagccgcgg gcgctgatga     120

tgggtgagga gggggcggca agatttcggg cgcccctgcc ctgaacgccc tcagctgctg     180

ccgccggggc cgctccagtg cctgcgaact ctgaggagcc gaggcgccgg tgagagcaag     240

gacgctgcaa acttgcgcag cgcgggggct gggattcacg cccagaagtt cagcaggcag     300

acagtccgaa gccttcccgc agcggagaga tagcttgagg gtgcgcaaga cggcagcctc     360

cgccctcggt tcccgcccag accgggcaga agagcttgga ggagccaaaa ggaacgcaaa     420

aggcggccag gacagcgtgc agcagctggg agccgccgtt ctcagcctta aaagttgcag     480

agattggagg ctgccccgag aggggacaga ccccagctcc gactgcgggg ggcaggagag     540

gacggtaccc aactgccacc tcccttcaac catagtagtt cctctgtacc gagcgcagcg     600
```

```
agctacagac gggggcgcgg cactcggcgc ggagagcggg aggctcaagg tcccagccag    660
tgagcccagt gtgcttgagt gtctctggac tcgcccctga gcttccaggt ctgtttcatt    720
tagactcctg ctcgcctccg tgcagttggg ggaaagcaag agacttgcgc gcacgcacag    780
tcctctggag atcaggtgga aggagccgct gggtaccaag gactgttcag agcctcttcc    840
catctcgggg agagcgaagg gtgaggctgg gcccggagag cagtgtaaac ggcctcctcc    900
ggcgggatgg gagccatcgg gctcctgtgg ctcctgccgc tgctgctttc cacggcagct    960
gtgggctccg ggatggggac cggccagcgc gcgggctccc cagctgcggg gccgccgctg   1020
cagccccggg agccactcag ctactcgcgc ctgcagagga agagtctggc agttgacttc   1080
gtggtgccct cgctcttccg tgtctacgcc cgggacctac tgctgccacc atcctcctcg   1140
gagctgaagg ctggcaggcc cgaggcccgc ggctcgctag ctctggactg cgccccgctg   1200
ctcaggttgc tggggccggc gccgggggtc tcctggaccg ccggttcacc agccccggca   1260
gaggcccgga cgctgtccag ggtgctgaag ggcggctccg tgcgcaagct ccggcgtgcc   1320
aagcagttgg tgctggagct gggcgaggag gcgatcttgg agggttgcgt cgggcccccc   1380
ggggaggcgg ctgtggggct gctccagttc aatctcagcg agctgttcag ttggtggatt   1440
cgccaaggcg aagggcgact gaggatccgc ctgatgcccg agaagaaggc gtcggaagtg   1500
ggcagagagg gaaggctgtc cgcggcaatt cgcgcctccc agccccgcct tctcttccag   1560
atcttcggga ctggtcatag ctccttggaa tcaccaacaa acatgccttc tccttctcct   1620
gattatttta catggaatct cacctggata atgaaagact ccttcccttt cctgtctcat   1680
cgcagccgat atggtctgga gtgcagcttt gacttcccct gtgagctgga gtattcccct   1740
ccactgcatg acctcaggaa ccagagctgg tcctggcgcc gcatcccctc cgaggaggcc   1800
tcccagatgg acttgctgga tgggcctggg gcagagcgtt ctaaggagat gcccagaggc   1860
tcctttctcc ttctcaacac ctcagctgac tccaagcaca ccatcctgag tccgtggatg   1920
aggagcagca gtgagcactg cacactggcc gtctcggtgc acaggcacct gcagccctct   1980
ggaaggtaca ttgcccagct gctgccccac aacgaggctg caagagagat cctcctgatg   2040
cccactccag ggaagcatgg ttggacagtg ctccagggaa gaatcgggcg tccagacaac   2100
ccatttcgag tggccctgga atacatctcc agtggaaacc gcagcttgtc tgcagtggac   2160
ttctttgccc tgaagaactg cagtgaagga acatccccag gctccaagat ggccctgcag   2220
agctccttca cttgttggaa tgggacagtc ctccagcttg ggcaggcctg tgacttccac   2280
caggactgtg cccagggaga agatgagagc cagatgtgcc ggaaactgcc tgtgggtttt   2340
tactgcaact ttgaagatgg cttctgtggc tggacccaag gcacactgtc accccacact   2400
cctcaatggc aggtcaggac cctaaaggat gcccggttcc aggaccacca agaccatgct   2460
ctattgctca gtaccactga tgtccccgct tctgaaagtg ctacagtgac cagtgctacg   2520
tttcctgcac cgatcaagag ctctccatgt gagctccgaa tgtcctggct cattcgtgga   2580
gtcttgaggg gaaacgtgtc cttggtgcta gtggagaaca aaaccgggaa ggagcaaggc   2640
aggatggtct ggcatgtcgc cgcctatgaa ggcttgagcc tgtggcagtg gatggtgttg   2700
cctctcctcg atgtgtctga caggttctgg ctgcagatgg tcgcatggtg gggacaagga   2760
tccagagcca tcgtggcttt tgacaatatc tccatcagcc tggactgcta cctcaccatt   2820
agcggagagg acaagatcct gcagaataca gcacccaaat caagaaacct gtttgagaga   2880
aacccaaaca aggagctgaa acccggggaa aattcaccaa gacagacccc catctttgac   2940
```

-continued

```
cctacagttc attggctgtt caccacatgt ggggccagcg ggccccatgg ccccacccag   3000
gcacagtgca acaacgccta ccagaactcc aacctgagcg tggaggtggg gagcgagggc   3060
cccctgaaag gcatccagat ctggaaggtg ccagccaccg acacctacag catctcgggc   3120
tacggagctg ctggcgggaa aggcgggaag aacaccatga tgcggtccca cggcgtgtct   3180
gtgctgggca tcttcaacct ggagaaggat gacatgctgt acatcctggt tgggcagcag   3240
ggagaggacg cctgccccag tacaaaccag ttaatccaga aagtctgcat tggagagaac   3300
aatgtgatag aagaagaaat ccgtgtgaac agaagcgtgc atgagtgggc aggaggcgga   3360
ggaggagggg gtggagccac ctacgtattt aagatgaagg atggagtgcc ggtgcccctg   3420
atcattgcag ccggaggtgg tggcagggcc tacggggcca agacagacac gttccaccca   3480
gagagactgg agaataactc ctcggttcta gggctaaacg gcaattccgg agccgcaggt   3540
ggtggaggtg gctggaatga taacacttcc ttgctctggg ccggaaaatc tttgcaggag   3600
ggtgccaccg gaggacattc ctgcccccag gccatgaaga agtgggggtg ggagacaaga   3660
gggggtttcg gagggggtgg agggggggtgc tcctcaggtg gaggaggcgg aggatatata   3720
ggcggcaatg cagcctcaaa caatgacccc gaaatggatg gggaagatgg ggtttccttc   3780
atcagtccac tgggcatcct gtacacccca gctttaaaag tgatggaagg ccacggggaa   3840
gtgaatatta agcattatct aaactgcagt cactgtgagg tagacgaatg tcacatggac   3900
cctgaaagcc acaaggtcat ctgcttctgt gaccacggga cggtgctggc tgaggatggc   3960
gtctcctgca ttgtgtcacc caccccggag ccacacctgc cactctcgct gatcctctct   4020
gtggtgacct ctgccctcgt ggccgccctg gtcctggctt tctccggcat catgattgtg   4080
taccgccgga agcaccagga gctgcaagcc atgcagatgg agctgcagag ccctgagtac   4140
aagctgagca agctccgcac ctcgaccatc atgaccgact acaaccccaa ctactgcttt   4200
gctggcaaga cctcctccat cagtgacctg aaggaggtgc cgcggaaaaa catcaccctc   4260
attcggggtc tgggccatgg cgcctttggg gaggtgtatg aaggccaggt gtccggaatg   4320
cccaacgacc caagcccccct gcaagtggct gtgaagacgc tgcctgaagt gtgctctgaa   4380
caggacgaac tggatttcct catggaagcc ctgatcatca gcaaattcaa ccaccagaac   4440
attgttcgct gcattggggt gagcctgcaa tccctgcccc ggttcatcct gctggagctc   4500
atggcggggg gagacctcaa gtccttcctc cgagagaccc gccctcgccc gagccagccc   4560
tcctccctgg ccatgctgga ccttctgcac gtggctcggg acattgcctg tggctgtcag   4620
tatttggagg aaaaccactt catccaccga gacattgctg ccagaaactg cctcttgacc   4680
tgtccaggcc ctggaagagt ggccaagatt ggagacttcg ggatggcccg agacatctac   4740
agggcgagct actatagaaa gggaggctgt gccatgctgc cagttaagtg gatgccccca   4800
gaggccttca tggaaggaat attcacttct aaaacagaca catggtcctt tggagtgctg   4860
ctatgggaaa tcttttctct tggatatatg ccataccccca gcaaaagcaa ccaggaagtt   4920
ctggagtttg tcaccagtgg aggccggatg gacccaccca agaactgccc tgggcctgta   4980
taccggataa tgactcagtg ctggcaacat cagcctgaag acaggcccaa ctttgccatc   5040
attttggaga ggattgaata ctgcacccag gacccggatg taatcaacac cgctttgccg   5100
atagaatatg gtccacttgt ggaagaggaa gagaaagtgc ctgtgaggcc caaggaccct   5160
gagggggttc ctcctctcct ggtctctcaa caggcaaaac gggaggagga gcgcagccca   5220
gctgccccac cacctctgcc taccacctcc tctggcaagg ctgcaaagaa acccacagct   5280
gcagagatct ctgttcgagt ccctagaggg ccggccgtgg aagggggaca cgtgaatatg   5340
```

```
gcattctctc agtccaaccc tccttcggag ttgcacaagg tccacggatc cagaaacaag   5400

cccaccagct tgtggaaccc aacgtacggc tcctggttta cagagaaacc caccaaaaag   5460

aataatccta tagcaaagaa ggagccacac gacaggggta acctggggct ggagggaagc   5520

tgtactgtcc cacctaacgt tgcaactggg agacttccgg gggcctcact gctcctagag   5580

ccctcttcgc tgactgccaa tatgaaggag gtacctctgt tcaggctacg tcacttccct   5640

tgtgggaatg tcaattacgg ctaccagcaa cagggcttgc ccttagaagc cgctactgcc   5700

cctggagctg gtcattacga ggataccatt ctgaaaagca agaatagcat gaaccagcct   5760

gggccctgag ctcggtcgca cactcacttc tcttccttgg gatccctaag accgtggagg   5820

agagagaggc aatggctcct tcacaaacca gagaccaaat gtcacgtttt gttttgtgcc   5880

aacctatttt gaagtaccac caaaaaagct gtattttgaa aatgctttag aaaggttttg   5940

agcatgggtt catcctattc tttcgaaaga agaaaatatc ataaaaatga gtgataaata   6000

caaggcccag atgtggttgc ataaggtttt tatgcatgtt tgttgtatac ttccttatgc   6060

ttctttcaaa ttgtgtgtgc tctgcttcaa tgtagtcaga attagctgct tctatgtttc   6120

atagttgggg tcatagatgt ttccttgcct tgttgatgtg gacatgagcc atttgagggg   6180

agagggaacg gaaataaagg agttatttgt aatgactaaa a                        6221

<210> SEQ ID NO 10
<211> LENGTH: 680
<212> TYPE: PRT
<213> ORGANISM: Homo sapiens

<400> SEQUENCE: 10

Met Glu Asp Ser Met Asp Met Asp Met Ser Pro Leu Arg Pro Gln Asn
1               5                   10                  15

Tyr Leu Phe Gly Cys Glu Leu Lys Ala Asp Lys Asp Tyr His Phe Lys
            20                  25                  30

Val Asp Asn Asp Glu Asn Glu His Gln Leu Ser Leu Arg Thr Val Ser
        35                  40                  45

Leu Gly Ala Gly Ala Lys Asp Glu Leu His Ile Val Glu Ala Glu Ala
    50                  55                  60

Met Asn Tyr Glu Gly Ser Pro Ile Lys Val Thr Leu Ala Thr Leu Lys
65                  70                  75                  80

Met Ser Val Gln Pro Thr Val Ser Leu Gly Gly Phe Glu Ile Thr Pro
                85                  90                  95

Pro Val Val Leu Arg Leu Lys Cys Gly Ser Gly Pro Val His Ile Ser
            100                 105                 110

Gly Gln His Leu Val Val Tyr Arg Arg Lys His Gln Glu Leu Gln Ala
        115                 120                 125

Met Gln Met Glu Leu Gln Ser Pro Glu Tyr Lys Leu Ser Lys Leu Arg
    130                 135                 140

Thr Ser Thr Ile Met Thr Asp Tyr Asn Pro Asn Tyr Cys Phe Ala Gly
145                 150                 155                 160

Lys Thr Ser Ser Ile Ser Asp Leu Lys Glu Val Pro Arg Lys Asn Asn
                165                 170                 175

Thr Leu Ile Arg Gly Leu Gly His Gly Ala Phe Gly Glu Val Tyr Glu
            180                 185                 190

Gly Gln Val Ser Gly Met Pro Asn Asp Pro Ser Pro Leu Gln Val Ala
        195                 200                 205

Val Lys Thr Leu Pro Glu Val Cys Ser Glu Gln Asp Glu Leu Asp Phe
```

```
    210                 215                 220

Leu Met Glu Ala Leu Ile Ile Ser Lys Phe Asn His Gln Asn Ile Val
225                 230                 235                 240

Arg Cys Ile Gly Val Ser Leu Gln Ser Leu Pro Arg Phe Ile Leu Leu
                245                 250                 255

Glu Leu Met Ala Gly Gly Asp Leu Lys Ser Phe Leu Arg Glu Thr Arg
            260                 265                 270

Pro Arg Pro Ser Gln Pro Ser Ser Leu Ala Met Leu Asp Leu Leu His
        275                 280                 285

Val Ala Arg Asp Ile Ala Cys Gly Cys Gln Tyr Leu Glu Glu Asn His
    290                 295                 300

Phe Ile His Arg Asp Ile Ala Ala Arg Asn Cys Leu Leu Thr Cys Pro
305                 310                 315                 320

Gly Pro Gly Arg Val Ala Lys Ile Gly Asp Phe Gly Met Ala Arg Asp
                325                 330                 335

Ile Tyr Arg Ala Ser Tyr Tyr Arg Lys Gly Gly Cys Ala Met Leu Pro
            340                 345                 350

Val Lys Trp Met Pro Pro Glu Ala Phe Met Glu Gly Ile Phe Thr Ser
        355                 360                 365

Lys Thr Asp Thr Trp Ser Phe Gly Val Leu Leu Trp Glu Ile Phe Ser
    370                 375                 380

Leu Gly Tyr Met Pro Tyr Pro Ser Lys Ser Asn Gln Glu Val Leu Glu
385                 390                 395                 400

Phe Val Thr Ser Gly Gly Arg Met Asp Pro Pro Lys Asn Cys Pro Gly
                405                 410                 415

Pro Val Tyr Arg Ile Met Thr Gln Cys Trp Gln His Gln Pro Glu Asp
            420                 425                 430

Arg Pro Asn Phe Ala Ile Ile Leu Glu Arg Ile Glu Tyr Cys Thr Gln
        435                 440                 445

Asp Pro Asp Val Ile Asn Thr Ala Leu Pro Ile Glu Tyr Gly Pro Leu
    450                 455                 460

Val Glu Glu Glu Glu Lys Val Pro Val Arg Pro Lys Asp Pro Glu Gly
465                 470                 475                 480

Val Pro Pro Leu Leu Val Ser Gln Gln Ala Lys Arg Glu Glu Glu Arg
                485                 490                 495

Ser Pro Ala Ala Pro Pro Pro Leu Pro Thr Thr Ser Ser Gly Lys Ala
            500                 505                 510

Ala Lys Lys Pro Thr Ala Ala Glu Val Ser Val Arg Val Pro Arg Gly
        515                 520                 525

Pro Ala Val Glu Gly Gly His Val Asn Met Ala Phe Ser Gln Ser Asn
    530                 535                 540

Pro Pro Ser Glu Leu His Arg Val His Gly Ser Arg Asn Lys Pro Thr
545                 550                 555                 560

Ser Leu Trp Asn Pro Thr Tyr Gly Ser Trp Phe Thr Glu Lys Pro Thr
                565                 570                 575

Lys Lys Asn Asn Pro Ile Ala Lys Lys Glu Pro His Glu Arg Gly Asn
            580                 585                 590

Leu Gly Leu Glu Gly Ser Cys Thr Val Pro Pro Asn Val Ala Thr Gly
        595                 600                 605

Arg Leu Pro Gly Ala Ser Leu Leu Leu Glu Pro Ser Ser Leu Thr Ala
    610                 615                 620

Asn Met Lys Glu Val Pro Leu Phe Arg Leu Arg His Phe Pro Cys Gly
625                 630                 635                 640
```

Asn Val Asn Tyr Gly Tyr Gln Gln Gln Gly Leu Pro Leu Glu Ala Ala
645 650 655

Thr Ala Pro Gly Ala Gly His Tyr Glu Asp Thr Ile Leu Lys Ser Lys
660 665 670

Asn Ser Met Asn Gln Pro Gly Pro
675 680

<210> SEQ ID NO 11
<211> LENGTH: 680
<212> TYPE: PRT
<213> ORGANISM: Homo sapiens

<400> SEQUENCE: 11

Met Glu Asp Ser Met Asp Met Asp Met Ser Pro Leu Arg Pro Gln Asn
1 5 10 15

Tyr Leu Phe Gly Cys Glu Leu Lys Ala Asp Lys Asp Tyr His Phe Lys
20 25 30

Val Asp Asn Asp Glu Asn Glu His Gln Leu Ser Leu Arg Thr Val Ser
35 40 45

Leu Gly Ala Gly Ala Lys Asp Glu Leu His Ile Val Glu Ala Glu Ala
50 55 60

Met Asn Tyr Glu Gly Ser Pro Ile Lys Val Thr Leu Ala Thr Leu Lys
65 70 75 80

Met Ser Val Gln Pro Thr Val Ser Leu Gly Gly Phe Glu Ile Thr Pro
85 90 95

Pro Val Val Leu Arg Leu Lys Cys Gly Ser Gly Pro Val His Ile Ser
100 105 110

Gly Gln His Leu Val Val Tyr Arg Arg Lys His Gln Glu Leu Gln Ala
115 120 125

Met Gln Met Glu Leu Gln Ser Pro Glu Tyr Lys Leu Ser Lys Leu Arg
130 135 140

Thr Ser Thr Ile Met Thr Asp Tyr Asn Pro Asn Tyr Cys Phe Ala Gly
145 150 155 160

Lys Thr Ser Ser Ile Ser Asp Leu Lys Glu Val Pro Arg Lys Asn Ile
165 170 175

Thr Leu Ile Arg Gly Leu Gly His Gly Ala Phe Gly Glu Val Tyr Glu
180 185 190

Gly Gln Val Ser Gly Met Pro Asn Asp Pro Ser Pro Leu Gln Val Ala
195 200 205

Val Lys Thr Leu Pro Glu Val Cys Ser Glu Gln Asp Glu Leu Asp Phe
210 215 220

Leu Met Glu Ala Leu Ile Ile Ser Lys Phe Asn His Gln Asn Ile Val
225 230 235 240

Arg Cys Ile Gly Val Ser Leu Gln Ser Leu Pro Arg Phe Ile Leu Leu
245 250 255

Glu Leu Met Ala Gly Gly Asp Leu Lys Ser Phe Leu Arg Glu Thr Arg
260 265 270

Pro Arg Pro Ser Gln Pro Ser Ser Leu Ala Met Leu Asp Leu Leu His
275 280 285

Val Ala Arg Asp Ile Ala Cys Gly Cys Gln Tyr Leu Glu Glu Asn His
290 295 300

Phe Ile His Arg Asp Ile Ala Ala Arg Asn Cys Leu Leu Thr Cys Pro
305 310 315 320

Gly Pro Gly Arg Val Ala Lys Ile Gly Asp Phe Gly Met Ala Arg Asp

```
                325                 330                 335

Ile Tyr Arg Ala Ser Tyr Tyr Arg Lys Gly Gly Cys Ala Met Leu Pro
            340                 345                 350

Val Lys Trp Met Pro Pro Glu Ala Phe Met Glu Gly Ile Phe Thr Ser
        355                 360                 365

Lys Thr Asp Thr Trp Ser Phe Gly Val Leu Leu Trp Glu Ile Phe Ser
    370                 375                 380

Leu Gly Tyr Met Pro Tyr Pro Ser Lys Ser Asn Gln Glu Val Leu Glu
385                 390                 395                 400

Phe Val Thr Ser Gly Gly Arg Met Asp Pro Pro Lys Asn Cys Pro Gly
                405                 410                 415

Pro Val Tyr Arg Ile Met Thr Gln Cys Trp Gln His Gln Pro Glu Asp
            420                 425                 430

Arg Pro Asn Phe Ala Ile Ile Leu Glu Arg Ile Glu Tyr Cys Thr Gln
        435                 440                 445

Asp Pro Asp Val Ile Asn Thr Ala Leu Pro Ile Glu Tyr Gly Pro Leu
    450                 455                 460

Val Glu Glu Glu Glu Lys Val Pro Val Arg Pro Lys Asp Pro Glu Gly
465                 470                 475                 480

Val Pro Pro Leu Leu Val Ser Gln Gln Ala Lys Arg Glu Glu Glu Arg
                485                 490                 495

Ser Pro Ala Ala Pro Pro Pro Leu Pro Thr Thr Ser Ser Gly Lys Ala
            500                 505                 510

Ala Lys Lys Pro Thr Ala Ala Glu Val Ser Val Arg Val Pro Arg Gly
        515                 520                 525

Pro Ala Val Glu Gly Gly His Val Asn Met Ala Phe Ser Gln Ser Asn
    530                 535                 540

Pro Pro Ser Glu Leu His Lys Val His Gly Ser Arg Asn Lys Pro Thr
545                 550                 555                 560

Ser Leu Trp Asn Pro Thr Tyr Gly Ser Trp Phe Thr Glu Lys Pro Thr
                565                 570                 575

Lys Lys Asn Asn Pro Ile Ala Lys Lys Glu Pro His Asp Arg Gly Asn
            580                 585                 590

Leu Gly Leu Glu Gly Ser Cys Thr Val Pro Pro Asn Val Ala Thr Gly
        595                 600                 605

Arg Leu Pro Gly Ala Ser Leu Leu Leu Glu Pro Ser Ser Leu Thr Ala
    610                 615                 620

Asn Met Lys Glu Val Pro Leu Phe Arg Leu Arg His Phe Pro Cys Gly
625                 630                 635                 640

Asn Val Asn Tyr Gly Tyr Gln Gln Gln Gly Leu Pro Leu Glu Ala Ala
                645                 650                 655

Thr Ala Pro Gly Ala Gly His Tyr Glu Asp Thr Ile Leu Lys Ser Lys
            660                 665                 670

Asn Ser Met Asn Gln Pro Gly Pro
        675                 680
```

<210> SEQ ID NO 12
<211> LENGTH: 2043
<212> TYPE: DNA
<213> ORGANISM: Homo sapiens

<400> SEQUENCE: 12

```
atggaagatt cgatggacat ggacatgagc cccctgaggc cccagaacta tcttttcggt      60

tgtgaactaa aggccgacaa agattatcac tttaaggtgg ataatgatga aaatgagcac     120
```

cagttatctt taagaacggt cagtttaggg gctggtgcaa aggatgagtt gcacattgtt 180
gaagcagagg caatgaatta cgaaggcagt ccaattaaag taacactggc aactttgaaa 240
atgtctgtac agccaacggt ttcccttggg ggctttgaaa taacaccacc agtggtctta 300
aggttgaagt gtggttcagg gccagtgcat attagtggac agcacttagt agtgtaccgc 360
cggaagcacc aggagctgca agccatgcag atggagctgc agagccctga gtacaagctg 420
agcaagctcc gcacctcgac catcatgacc gactacaacc ccaactactg ctttgctggc 480
aagacctcct ccatcagtga cctgaaggag gtgccgcgga aaaacatcac cctcattcgg 540
ggtctgggcc atggcgcctt tggggaggtg tatgaaggcc aggtgtccgg aatgcccaac 600
gacccaagcc ccctgcaagt ggctgtgaag acgctgcctg aagtgtgctc tgaacaggac 660
gaactggatt tcctcatgga agccctgatc atcagcaaat tcaaccacca gaacattgtt 720
cgctgcattg gggtgagcct gcaatccctg ccccggttca tcctgctgga gctcatggcg 780
gggggagacc tcaagtcctt cctccgagag acccgccctc gcccgagcca gccctcctcc 840
ctggccatgc tggaccttct gcacgtggct cgggacattg cctgtggctg tcagtatttg 900
gaggaaaacc acttcatcca ccgagacatt gctgccagaa actgcctctt gacctgtcca 960
ggccctggaa gagtggccaa gattggagac ttcgggatgg cccgagacat ctacagggcg 1020
agctactata gaaagggagg ctgtgccatg ctgccagtta agtggatgcc cccagaggcc 1080
ttcatggaag gaatattcac ttctaaaaca gacacatggt cctttggagt gctgctatgg 1140
gaaatctttt ctcttggata tatgccatac cccagcaaaa gcaaccagga agttctggag 1200
tttgtcacca gtggaggccg gatggaccca cccaagaact gccctgggcc tgtataccgg 1260
ataatgactc agtgctggca acatcagcct gaagacaggc ccaactttgc catcattttg 1320
gagaggattg aatactgcac ccaggacccg gatgtaatca acaccgcttt gccgatagaa 1380
tatggtccac ttgtggaaga ggaagagaaa gtgcctgtga ggcccaagga ccctgagggg 1440
gttcctcctc tcctggtctc tcaacaggca aaacgggagg aggagcgcag cccagctgcc 1500
ccaccacctc tgcctaccac ctcctctggc aaggctgcaa agaaacccac agctgcagag 1560
gtctctgttc gagtccctag agggccggcc gtggaagggg gacacgtgaa tatggcattc 1620
tctcagtcca accctccttc ggagttgcac aaggtccacg gatccagaaa caagcccacc 1680
agcttgtgga acccaacgta cggctcctgg tttacagaga aacccaccaa aaagaataat 1740
cctatagcaa agaaggagcc acacgacagg ggtaacctgg ggctggaggg aagctgtact 1800
gtcccaccta acgttgcaac tgggagactt ccgggggcct cactgctcct agagccctct 1860
tcgctgactg ccaatatgaa ggaggtacct ctgttcaggc tacgtcactt ccccttgtggg 1920 aatgtcaatt acggctacca gcaacagggc ttgcccttag aagccgctac tgcccctgga 1980
gctggtcatt acgaggatac cattctgaaa agcaagaata gcatgaacca gcctgggccc 2040
tga 2043

<210> SEQ ID NO 13
<211> LENGTH: 1129
<212> TYPE: PRT
<213> ORGANISM: Homo sapiens

<400> SEQUENCE: 13

Met Asp Gly Phe Ala Gly Ser Leu Asp Asp Ser Ile Ser Ala Ala Ser
1 5 10 15

Thr Ser Asp Val Gln Asp Arg Leu Ser Ala Leu Glu Ser Arg Val Gln

```
                20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190

Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
    210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Val Leu Phe Asn Tyr Glu Glu Arg Thr Gln Arg His
    290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
        355                 360                 365

Leu Asp Phe Ser Lys Ala Asp Ser Gly Val His Leu Cys Val Ile Asp
    370                 375                 380

Asp Ser Asn Glu His Met Leu Thr Val Trp Asp Trp Gln Arg Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
            420                 425                 430

Ile Phe Phe Trp Thr Trp Ser Gly Asn Ser Leu Thr Arg Lys Gln Gly
        435                 440                 445
```

```
Ile Phe Gly Lys Tyr Glu Lys Pro Lys Phe Val Gln Cys Leu Ala Phe
    450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
                485                 490                 495

Gly Val Tyr Gln Ile Ser Lys Gln Ile Lys Ala His Asp Gly Ser Val
            500                 505                 510

Phe Thr Leu Cys Gln Met Arg Asn Gly Met Leu Leu Thr Gly Gly Gly
        515                 520                 525

Lys Asp Arg Lys Ile Ile Leu Trp Asp His Asp Leu Asn Pro Glu Arg
    530                 535                 540

Glu Ile Glu Phe Ser Ala Ser Arg Ala Arg Leu Pro Gly His Val Ala
545                 550                 555                 560

Ala Asp His Pro Pro Ala Val Tyr Arg Arg Lys His Gln Glu Leu Gln
                565                 570                 575

Ala Met Gln Met Glu Leu Gln Ser Pro Glu Tyr Lys Leu Ser Lys Leu
            580                 585                 590

Arg Thr Ser Thr Ile Met Thr Asp Tyr Asn Pro Asn Tyr Cys Phe Ala
        595                 600                 605

Gly Lys Thr Ser Ser Ile Ser Asp Leu Lys Glu Val Pro Arg Lys Asn
    610                 615                 620

Ile Thr Leu Ile Arg Gly Leu Gly His Gly Ala Phe Gly Glu Val Tyr
625                 630                 635                 640

Glu Gly Gln Val Ser Gly Met Pro Asn Asp Pro Ser Pro Leu Gln Val
                645                 650                 655

Ala Val Lys Thr Leu Pro Glu Val Cys Ser Glu Gln Asp Glu Leu Asp
            660                 665                 670

Phe Leu Met Glu Ala Leu Ile Ile Ser Lys Phe Asn His Gln Asn Ile
        675                 680                 685

Val Arg Cys Ile Gly Val Ser Leu Gln Ser Leu Pro Arg Phe Ile Leu
    690                 695                 700

Leu Glu Leu Met Ala Gly Gly Asp Leu Lys Ser Phe Leu Arg Glu Thr
705                 710                 715                 720

Arg Pro Arg Pro Ser Gln Pro Ser Ser Leu Ala Met Leu Asp Leu Leu
                725                 730                 735

His Val Ala Arg Asp Ile Ala Cys Gly Cys Gln Tyr Leu Glu Glu Asn
            740                 745                 750

His Phe Ile His Arg Asp Ile Ala Ala Arg Asn Cys Leu Leu Thr Cys
        755                 760                 765

Pro Gly Pro Gly Arg Val Ala Lys Ile Gly Asp Phe Gly Met Ala Arg
    770                 775                 780

Asp Ile Tyr Arg Ala Ser Tyr Tyr Arg Lys Gly Gly Cys Ala Met Leu
785                 790                 795                 800

Pro Val Lys Trp Met Pro Pro Glu Ala Phe Met Glu Gly Ile Phe Thr
                805                 810                 815

Ser Lys Thr Asp Thr Trp Ser Phe Gly Val Leu Leu Trp Glu Ile Phe
            820                 825                 830

Ser Leu Gly Tyr Met Pro Tyr Pro Ser Lys Ser Asn Gln Glu Val Leu
        835                 840                 845

Glu Phe Val Thr Ser Gly Gly Arg Met Asp Pro Pro Lys Asn Cys Pro
    850                 855                 860
```

```
Gly Pro Val Tyr Arg Ile Met Thr Gln Cys Trp Gln His Gln Pro Glu
865                 870                 875                 880

Asp Arg Pro Asn Phe Ala Ile Ile Leu Glu Arg Ile Glu Tyr Cys Thr
                885                 890                 895

Gln Asp Pro Asp Val Ile Asn Thr Ala Leu Pro Ile Glu Tyr Gly Pro
            900                 905                 910

Leu Val Glu Glu Glu Glu Lys Val Pro Val Arg Pro Lys Asp Pro Glu
        915                 920                 925

Gly Val Pro Pro Leu Leu Val Ser Gln Gln Ala Lys Arg Glu Glu Glu
    930                 935                 940

Arg Ser Pro Ala Ala Pro Pro Pro Leu Pro Thr Thr Ser Ser Gly Lys
945                 950                 955                 960

Ala Ala Lys Lys Pro Thr Ala Ala Glu Ile Ser Val Arg Val Pro Arg
                965                 970                 975

Gly Pro Ala Val Glu Gly Gly His Val Asn Met Ala Phe Ser Gln Ser
            980                 985                 990

Asn Pro Pro Ser Glu Leu His Lys  Val His Gly Ser Arg  Asn Lys Pro
        995                 1000                1005

Thr Ser  Leu Trp Asn Pro Thr  Tyr Gly Ser Trp Phe  Thr Glu Lys
    1010                1015                1020

Pro Thr  Lys Lys Asn Asn Pro  Ile Ala Lys Lys Glu  Pro His Asp
    1025                1030                1035

Arg Gly  Asn Leu Gly Leu Glu  Gly Ser Cys Thr Val  Pro Pro Asn
    1040                1045                1050

Val Ala  Thr Gly Arg Leu Pro  Gly Ala Ser Leu Leu  Leu Glu Pro
    1055                1060                1065

Ser Ser  Leu Thr Ala Asn Met  Lys Glu Val Pro Leu  Phe Arg Leu
    1070                1075                1080

Arg His  Phe Pro Cys Gly Asn  Val Asn Tyr Gly Tyr  Gln Gln Gln
    1085                1090                1095

Gly Leu  Pro Leu Glu Ala Ala  Thr Ala Pro Gly Ala  Gly His Tyr
    1100                1105                1110

Glu Asp  Thr Ile Leu Lys Ser  Lys Asn Ser Met Asn  Gln Pro Gly
    1115                1120                1125

Pro
```

<210> SEQ ID NO 14
<211> LENGTH: 3926
<212> TYPE: DNA
<213> ORGANISM: Homo sapiens

<400> SEQUENCE: 14

```
ggcggcgcgg cgcggcgctc gcggctgctg cctgggaggg aggccgggca ggcggctgag     60

cggcgcggct ctcaacgtga cggggaagtg gttcgggcgg ccgcggctta ctaccccagg    120

gcgaacggac ggacgacgga ggcgggagcc ggtagccgag ccgggcgacc tagagaacga    180

gcgggtcagg ctcagcgtcg gccactctgt cggtccgctg aatgaagtgc ccgcccctct    240

gagcccggag cccggcgctt tccccgcaag atggacggtt tcgccggcag tctcgatgat    300

agtatttctg ctgcaagtac ttctgatgtt caagatcgcc tgtcagctct tgagtcacga    360

gttcagcaac aagaagatga aatcactgtg ctaaaggcgg ctttggctga tgttttgagg    420

cgtcttgcaa tctctgaaga tcatgtggcc tcagtgaaaa aatcagtctc aagtaaaggc    480

caaccaagcc ctcgagcagt tattcccatg tcctgtataa ccaatggaag tggtgcaaac    540
```

-continued

```
agaaaaccaa gtcataccag tgctgtctca attgcaggaa aagaaactct ttcatctgct    600
gctaaaagtg gtacagaaaa aaagaaagaa aaaccacaag gacagagaga aaaaaaagag    660
gaatctcatt ctaatgatca aagtccacaa attcgagcat caccttctcc ccagccctct    720
tcacaacctc tccaaataca cagacaaact ccagaaagca agaatgctac tcccaccaaa    780
agcataaaac gaccatcacc agctgaaaag tcacataatt cttgggaaaa ttcagatgat    840
agccgtaata aattgtcgaa aataccttca acacccaaat taataccaaa agttaccaaa    900
actgcagaca agcataaaga tgtcatcatc aaccaagaag gagaatatat taaaatgttt    960
atgcgcggtc ggccaattac catgttcatt ccttccgatg ttgacaacta tgatgacatc   1020
agaacggaac tgcctcctga gaagctcaaa ctggagtggg catatggtta tcgaggaaag   1080
gactgtagag ctaatgttta ccttcttccg accggggaaa tagtttattt cattgcatca   1140
gtagtagtac tatttaatta tgaggagaga actcagcgac actacctggg ccatacagac   1200
tgtgtgaaat gccttgctat acatcctgac aaaattagga ttgcaactgg acagatagct   1260
ggcgtggata aagatggaag gcctctacaa ccccacgtca gagtgtggga ttctgttact   1320
ctatccacac tgcagattat tggacttggc acttttgagc gtggagtagg atgcctggat   1380
ttttcaaaag cagattcagg tgttcattta tgtgttattg atgactccaa tgagcatatg   1440
cttactgtat gggactggca gaagaaagca aaaggagcag aaataaagac aacaaatgaa   1500
gttgttttgg ctgtggagtt tcacccaaca gatgcaaata ccataattac atgcggtaaa   1560
tctcatattt tcttctggac ctggagcggc aattcactaa caagaaaaca gggaattttt   1620
gggaaatatg aaaagccaaa atttgtgcag tgtttagcat tcttggggaa tggagatgtt   1680
cttactggag actcaggtgg agtcatgctt atatggagca aaactactgt agagcccaca   1740
cctgggaaag gacctaaagt gtaccgccgg aagcaccagg agctgcaagc catgcagatg   1800
gagctgcaga gccctgagta caagctgagc aagctccgca cctcgaccat catgaccgac   1860
tacaacccca actactgctt tgctggcaag acctcctcca tcagtgacct gaaggaggtg   1920
ccgcggaaaa acatcaccct cattcggggt ctgggccatg gagcctttgg ggaggtgtat   1980
gaaggccagg tgtccggaat gcccaacgac ccaagccccc tgcaagtggc tgtgaagacg   2040
ctgcctgaag tgtgctctga acaggacgaa ctggatttcc tcatggaagc cctgatcatc   2100
agcaaattca accaccagaa cattgttcgc tgcattgggg tgagcctgca atccctgccc   2160
cggttcatcc tgctggagct catggcgggg ggagacctca agtccttcct ccgagagacc   2220
cgccctcgcc cgagccagcc ctcctccctg gccatgctgg accttctgca cgtggctcgg   2280
gacattgcct gtggctgtca gtatttggag gaaaaccact tcatccaccg agacattgct   2340
gccagaaact gcctcttgac ctgtccaggc cctggaagag tggccaagat tggagacttc   2400
gggatggccc gagacatcta cagggcgagc tactatagaa agggaggctg tgccatgctg   2460
ccagttaagt ggatgccccc agaggccttc atggaaggaa tattcacttc taaaacagac   2520
acatggtcct ttggagtgct gctatgggaa atcttttctc ttggatatat gccatacccc   2580
agcaaaagca accaggaagt tctggagttt gtcaccagtg gaggccggat ggacccaccc   2640
aagaactgcc ctgggcctgt ataccggata atgactcagt gctggcaaca tcagcctgaa   2700
gacaggccca actttgccat cattttggag aggattgaat actgcaccca ggacccggat   2760
gtaatcaaca ccgctttgcc gatagaatat ggtccacttg tggaagagga agagaaagtg   2820
cctgtgaggc ccaaggaccc tgagggggtt cctcctctcc tggtctctca acaggcaaaa   2880
cgggaggagg agcgcagccc agctgcccca ccacctctgc ctaccacctc ctctggcaag   2940
```

```
gctgcaaaga aacccacagc tgcagaggtc tctgttcgag tccctagagg gccggccgtg   3000

gaagggggac acgtgaatat ggcattctct cagtccaacc ctccttcgga gttgcacagg   3060

gtccacggat ccagaaacaa gcccaccagc ttgtggaacc caacgtacgg ctcctggttt   3120

acagagaaac ccaccaaaaa gaataatcct atagcaaaga aggagccaca cgagaggggt   3180

aacctggggc tggagggaag ctgtactgtc ccacctaacg ttgcaactgg gagacttccg   3240

ggggcctcac tgctcctaga gccctcttcg ctgactgcca atatgaagga ggtacctctg   3300

ttcaggctac gtcacttccc ttgtgggaat gtcaattacg gctaccagca acagggcttg   3360

cccttagaag ccgctactgc ccctggagct ggtcattacg aggataccat tctgaaaagc   3420

aagaatagca tgaaccagcc tgggccctga gctcggtcac acactcactt ctcttccttg   3480

ggatccctaa gaccgtggag gagagagagg caatcaatgg ctccttcaca aaccagagac   3540

caaatgtcac gttttgtttt gtgccaacct attttgaagt accaccaaaa aagctgtatt   3600

ttgaaaatgc tttagaaagg ttttgagcat gggttcatcc tattctttcg aaagaagaaa   3660

atatcataaa aatgagtgat aaatacaagg cccagatgtg gttgcataag gtttttatgc   3720

atgtttgttg tatacttcct tatgcttctt ttaaattgtg tgtgctctgc ttcaatgtag   3780

tcagaattag ctgcttctat gtttcatagt tggggtcata gatgtttcct tgccttgttg   3840

atgtggacat gagccatttg aggggagagg gaacggaaat aaaggagtta tttgtaatga   3900

aaaaaaaaaa aaaaaaaaaa aaaaaa                                        3926


<210> SEQ ID NO 15
<211> LENGTH: 1059
<212> TYPE: PRT
<213> ORGANISM: Homo sapiens

<400> SEQUENCE: 15

Met Asp Gly Phe Ala Gly Ser Leu Asp Asp Ser Ile Ser Ala Ala Ser
1               5                   10                  15

Thr Ser Asp Val Gln Asp Arg Leu Ser Ala Leu Glu Ser Arg Val Gln
            20                  25                  30

Gln Gln Glu Asp Glu Ile Thr Val Leu Lys Ala Ala Leu Ala Asp Val
        35                  40                  45

Leu Arg Arg Leu Ala Ile Ser Glu Asp His Val Ala Ser Val Lys Lys
    50                  55                  60

Ser Val Ser Ser Lys Gly Gln Pro Ser Pro Arg Ala Val Ile Pro Met
65                  70                  75                  80

Ser Cys Ile Thr Asn Gly Ser Gly Ala Asn Arg Lys Pro Ser His Thr
                85                  90                  95

Ser Ala Val Ser Ile Ala Gly Lys Glu Thr Leu Ser Ser Ala Ala Lys
            100                 105                 110

Ser Gly Thr Glu Lys Lys Lys Glu Lys Pro Gln Gly Gln Arg Glu Lys
        115                 120                 125

Lys Glu Glu Ser His Ser Asn Asp Gln Ser Pro Gln Ile Arg Ala Ser
    130                 135                 140

Pro Ser Pro Gln Pro Ser Ser Gln Pro Leu Gln Ile His Arg Gln Thr
145                 150                 155                 160

Pro Glu Ser Lys Asn Ala Thr Pro Thr Lys Ser Ile Lys Arg Pro Ser
                165                 170                 175

Pro Ala Glu Lys Ser His Asn Ser Trp Glu Asn Ser Asp Asp Ser Arg
            180                 185                 190
```

```
Asn Lys Leu Ser Lys Ile Pro Ser Thr Pro Lys Leu Ile Pro Lys Val
        195                 200                 205

Thr Lys Thr Ala Asp Lys His Lys Asp Val Ile Ile Asn Gln Glu Gly
    210                 215                 220

Glu Tyr Ile Lys Met Phe Met Arg Gly Arg Pro Ile Thr Met Phe Ile
225                 230                 235                 240

Pro Ser Asp Val Asp Asn Tyr Asp Asp Ile Arg Thr Glu Leu Pro Pro
                245                 250                 255

Glu Lys Leu Lys Leu Glu Trp Ala Tyr Gly Tyr Arg Gly Lys Asp Cys
            260                 265                 270

Arg Ala Asn Val Tyr Leu Leu Pro Thr Gly Glu Ile Val Tyr Phe Ile
        275                 280                 285

Ala Ser Val Val Val Leu Phe Asn Tyr Glu Glu Arg Thr Gln Arg His
    290                 295                 300

Tyr Leu Gly His Thr Asp Cys Val Lys Cys Leu Ala Ile His Pro Asp
305                 310                 315                 320

Lys Ile Arg Ile Ala Thr Gly Gln Ile Ala Gly Val Asp Lys Asp Gly
                325                 330                 335

Arg Pro Leu Gln Pro His Val Arg Val Trp Asp Ser Val Thr Leu Ser
            340                 345                 350

Thr Leu Gln Ile Ile Gly Leu Gly Thr Phe Glu Arg Gly Val Gly Cys
        355                 360                 365

Leu Asp Phe Ser Lys Ala Asp Ser Gly Val His Leu Cys Val Ile Asp
    370                 375                 380

Asp Ser Asn Glu His Met Leu Thr Val Trp Asp Trp Gln Lys Lys Ala
385                 390                 395                 400

Lys Gly Ala Glu Ile Lys Thr Thr Asn Glu Val Val Leu Ala Val Glu
                405                 410                 415

Phe His Pro Thr Asp Ala Asn Thr Ile Ile Thr Cys Gly Lys Ser His
            420                 425                 430

Ile Phe Phe Trp Thr Trp Ser Gly Asn Ser Leu Thr Arg Lys Gln Gly
        435                 440                 445

Ile Phe Gly Lys Tyr Glu Lys Pro Lys Phe Val Gln Cys Leu Ala Phe
    450                 455                 460

Leu Gly Asn Gly Asp Val Leu Thr Gly Asp Ser Gly Gly Val Met Leu
465                 470                 475                 480

Ile Trp Ser Lys Thr Thr Val Glu Pro Thr Pro Gly Lys Gly Pro Lys
                485                 490                 495

Val Tyr Arg Arg Lys His Gln Glu Leu Gln Ala Met Gln Met Glu Leu
            500                 505                 510

Gln Ser Pro Glu Tyr Lys Leu Ser Lys Leu Arg Thr Ser Thr Ile Met
        515                 520                 525

Thr Asp Tyr Asn Pro Asn Tyr Cys Phe Ala Gly Lys Thr Ser Ser Ile
    530                 535                 540

Ser Asp Leu Lys Glu Val Pro Arg Lys Asn Ile Thr Leu Ile Arg Gly
545                 550                 555                 560

Leu Gly His Gly Ala Phe Gly Glu Val Tyr Glu Gly Gln Val Ser Gly
                565                 570                 575

Met Pro Asn Asp Pro Ser Pro Leu Gln Val Ala Val Lys Thr Leu Pro
            580                 585                 590

Glu Val Cys Ser Glu Gln Asp Glu Leu Asp Phe Leu Met Glu Ala Leu
        595                 600                 605

Ile Ile Ser Lys Phe Asn His Gln Asn Ile Val Arg Cys Ile Gly Val
```

```
    610                 615                 620

Ser Leu Gln Ser Leu Pro Arg Phe Ile Leu Leu Glu Leu Met Ala Gly
625                 630                 635                 640

Gly Asp Leu Lys Ser Phe Leu Arg Glu Thr Arg Pro Arg Pro Ser Gln
                645                 650                 655

Pro Ser Ser Leu Ala Met Leu Asp Leu Leu His Val Ala Arg Asp Ile
            660                 665                 670

Ala Cys Gly Cys Gln Tyr Leu Glu Glu Asn His Phe Ile His Arg Asp
        675                 680                 685

Ile Ala Ala Arg Asn Cys Leu Leu Thr Cys Pro Gly Pro Gly Arg Val
    690                 695                 700

Ala Lys Ile Gly Asp Phe Gly Met Ala Arg Asp Ile Tyr Arg Ala Ser
705                 710                 715                 720

Tyr Tyr Arg Lys Gly Gly Cys Ala Met Leu Pro Val Lys Trp Met Pro
                725                 730                 735

Pro Glu Ala Phe Met Glu Gly Ile Phe Thr Ser Lys Thr Asp Thr Trp
            740                 745                 750

Ser Phe Gly Val Leu Leu Trp Glu Ile Phe Ser Leu Gly Tyr Met Pro
        755                 760                 765

Tyr Pro Ser Lys Ser Asn Gln Glu Val Leu Glu Phe Val Thr Ser Gly
    770                 775                 780

Gly Arg Met Asp Pro Pro Lys Asn Cys Pro Gly Pro Val Tyr Arg Ile
785                 790                 795                 800

Met Thr Gln Cys Trp Gln His Gln Pro Glu Asp Arg Pro Asn Phe Ala
                805                 810                 815

Ile Ile Leu Glu Arg Ile Glu Tyr Cys Thr Gln Asp Pro Asp Val Ile
            820                 825                 830

Asn Thr Ala Leu Pro Ile Glu Tyr Gly Pro Leu Val Glu Glu Glu Glu
        835                 840                 845

Lys Val Pro Val Arg Pro Lys Asp Pro Glu Gly Val Pro Pro Leu Leu
    850                 855                 860

Val Ser Gln Gln Ala Lys Arg Glu Glu Glu Arg Ser Pro Ala Ala Pro
865                 870                 875                 880

Pro Pro Leu Pro Thr Thr Ser Ser Gly Lys Ala Ala Lys Lys Pro Thr
                885                 890                 895

Ala Ala Glu Val Ser Val Arg Val Pro Arg Gly Pro Ala Val Glu Gly
            900                 905                 910

Gly His Val Asn Met Ala Phe Ser Gln Ser Asn Pro Pro Ser Glu Leu
        915                 920                 925

His Arg Val His Gly Ser Arg Asn Lys Pro Thr Ser Leu Trp Asn Pro
    930                 935                 940

Thr Tyr Gly Ser Trp Phe Thr Glu Lys Pro Thr Lys Lys Asn Asn Pro
945                 950                 955                 960

Ile Ala Lys Lys Glu Pro His Glu Arg Gly Asn Leu Gly Leu Glu Gly
                965                 970                 975

Ser Cys Thr Val Pro Pro Asn Val Ala Thr Gly Arg Leu Pro Gly Ala
            980                 985                 990

Ser Leu Leu Leu Glu Pro Ser Ser  Leu Thr Ala Asn Met  Lys Glu Val
        995                 1000                1005

Pro Leu  Phe Arg Leu Arg His  Phe Pro Cys Gly Asn  Val Asn Tyr
    1010                1015                1020

Gly Tyr  Gln Gln Gln Gly Leu  Pro Leu Glu Ala Ala  Thr Ala Pro
    1025                1030                1035
```

Gly Ala Gly His Tyr Glu Asp Thr Ile Leu Lys Ser Lys Asn Ser
1040 1045 1050

Met Asn Gln Pro Gly Pro
1055

<210> SEQ ID NO 16
<211> LENGTH: 10
<212> TYPE: PRT
<213> ORGANISM: Homo sapiens

<400> SEQUENCE: 16

Ser Leu Ala Met Leu Asp Leu Leu His Val
1 5 10

<210> SEQ ID NO 17
<211> LENGTH: 680
<212> TYPE: PRT
<213> ORGANISM: Homo sapiens

<400> SEQUENCE: 17

Met Glu Asp Ser Met Asp Met Asp Met Ser Pro Leu Arg Pro Gln Asn
1 5 10 15

Tyr Leu Phe Gly Cys Glu Leu Lys Ala Asp Lys Asp Tyr His Phe Lys
20 25 30

Val Asp Asn Asp Glu Asn Glu His Gln Leu Ser Leu Arg Thr Val Ser
35 40 45

Leu Gly Ala Gly Ala Lys Asp Glu Leu His Ile Val Glu Ala Glu Ala
50 55 60

Met Asn Tyr Glu Gly Ser Pro Ile Lys Val Thr Leu Ala Thr Leu Lys
65 70 75 80

Met Ser Val Gln Pro Thr Val Ser Leu Gly Gly Phe Glu Ile Thr Pro
85 90 95

Pro Val Val Leu Arg Leu Lys Cys Gly Ser Gly Pro Val His Ile Ser
100 105 110

Gly Gln His Leu Val Val Tyr Arg Arg Lys His Gln Glu Leu Gln Ala
115 120 125

Met Gln Met Glu Leu Gln Ser Pro Glu Tyr Lys Leu Ser Lys Leu Arg
130 135 140

Thr Ser Thr Ile Met Thr Asp Tyr Asn Pro Asn Tyr Cys Phe Ala Gly
145 150 155 160

Lys Thr Ser Ser Ile Ser Asp Leu Lys Glu Val Pro Arg Lys Asn Ile
165 170 175

Thr Leu Ile Arg Gly Leu Gly His Gly Ala Phe Gly Glu Val Tyr Glu
180 185 190

Gly Gln Val Ser Gly Met Pro Asn Asp Pro Ser Pro Leu Gln Val Ala
195 200 205

Val Lys Thr Leu Pro Glu Val Cys Ser Glu Gln Asp Glu Leu Asp Phe
210 215 220

Leu Met Glu Ala Leu Ile Ile Ser Lys Phe Asn His Gln Asn Ile Val
225 230 235 240

Arg Cys Ile Gly Val Ser Leu Gln Ser Leu Pro Arg Phe Ile Leu Leu
245 250 255

Glu Leu Met Ala Gly Gly Asp Leu Lys Ser Phe Leu Arg Glu Thr Arg
260 265 270

Pro Arg Pro Ser Gln Pro Ser Ser Leu Ala Met Leu Asp Leu Leu His
275 280 285

```
Val Ala Arg Asp Ile Ala Cys Gly Cys Gln Tyr Leu Glu Glu Asn His
    290                 295                 300

Phe Ile His Arg Asp Ile Ala Ala Arg Asn Cys Leu Leu Thr Cys Pro
305                 310                 315                 320

Gly Pro Gly Arg Val Ala Lys Ile Gly Asp Phe Gly Met Ala Arg Asp
                325                 330                 335

Ile Tyr Arg Ala Ser Tyr Tyr Arg Lys Gly Gly Cys Ala Met Leu Pro
            340                 345                 350

Val Lys Trp Met Pro Pro Glu Ala Phe Met Glu Gly Ile Phe Thr Ser
        355                 360                 365

Lys Thr Asp Thr Trp Ser Phe Gly Val Leu Leu Trp Glu Ile Phe Ser
    370                 375                 380

Leu Gly Tyr Met Pro Tyr Pro Ser Lys Ser Asn Gln Glu Val Leu Glu
385                 390                 395                 400

Phe Val Thr Ser Gly Gly Arg Met Asp Pro Pro Lys Asn Cys Pro Gly
                405                 410                 415

Pro Val Tyr Arg Ile Met Thr Gln Cys Trp Gln His Gln Pro Glu Asp
            420                 425                 430

Arg Pro Asn Phe Ala Ile Ile Leu Glu Arg Ile Glu Tyr Cys Thr Gln
        435                 440                 445

Asp Pro Asp Val Ile Asn Thr Ala Leu Pro Ile Glu Tyr Gly Pro Leu
    450                 455                 460

Val Glu Glu Glu Glu Lys Val Pro Val Arg Pro Lys Asp Pro Glu Gly
465                 470                 475                 480

Val Pro Pro Leu Leu Val Ser Gln Gln Ala Lys Arg Glu Glu Glu Arg
                485                 490                 495

Ser Pro Ala Ala Pro Pro Pro Leu Pro Thr Thr Ser Ser Gly Lys Ala
            500                 505                 510

Ala Lys Lys Pro Thr Ala Ala Glu Val Ser Val Arg Val Pro Arg Gly
        515                 520                 525

Pro Ala Val Glu Gly Gly His Val Asn Met Ala Phe Ser Gln Ser Asn
    530                 535                 540

Pro Pro Ser Glu Leu His Lys Val His Gly Ser Arg Asn Lys Pro Thr
545                 550                 555                 560

Ser Leu Trp Asn Pro Thr Tyr Gly Ser Trp Phe Thr Glu Lys Pro Thr
                565                 570                 575

Lys Lys Asn Asn Pro Ile Ala Lys Lys Glu Pro His Asp Arg Gly Asn
            580                 585                 590

Leu Gly Leu Glu Gly Ser Cys Thr Val Pro Pro Asn Val Ala Thr Gly
        595                 600                 605

Arg Leu Pro Gly Ala Ser Leu Leu Leu Glu Pro Ser Ser Leu Thr Ala
    610                 615                 620

Asn Met Lys Glu Val Pro Leu Phe Arg Leu Arg His Phe Pro Cys Gly
625                 630                 635                 640

Asn Val Asn Tyr Gly Tyr Gln Gln Gln Gly Leu Pro Leu Glu Ala Ala
                645                 650                 655

Thr Ala Pro Gly Ala Gly His Tyr Glu Asp Thr Ile Leu Lys Ser Lys
            660                 665                 670

Asn Ser Met Asn Gln Pro Gly Pro
        675                 680
```

<210> SEQ ID NO 18
<211> LENGTH: 9

<212> TYPE: PRT
<213> ORGANISM: Homo sapiens

<400> SEQUENCE: 18

Val Leu Leu Trp Glu Ile Phe Ser Leu
1 5

<210> SEQ ID NO 19
<211> LENGTH: 9
<212> TYPE: PRT
<213> ORGANISM: Homo sapiens

<400> SEQUENCE: 19

Phe Leu Met Glu Ala Leu Ile Ile Ser
1 5

<210> SEQ ID NO 20
<211> LENGTH: 9
<212> TYPE: PRT
<213> ORGANISM: Homo sapiens

<400> SEQUENCE: 20

Lys Thr Asp Thr Trp Ser Phe Gly Val
1 5

<210> SEQ ID NO 21
<211> LENGTH: 9
<212> TYPE: PRT
<213> ORGANISM: Homo sapiens

<400> SEQUENCE: 21

Gly Met Ala Arg Asp Ile Tyr Arg Ala
1 5

<210> SEQ ID NO 22
<211> LENGTH: 10
<212> TYPE: PRT
<213> ORGANISM: Homo sapiens

<400> SEQUENCE: 22

Phe Leu Met Glu Ala Leu Ile Ile Ser Lys
1 5 10

<210> SEQ ID NO 23
<211> LENGTH: 10
<212> TYPE: PRT
<213> ORGANISM: Homo sapiens

<400> SEQUENCE: 23

Ser Leu Pro Arg Phe Ile Leu Leu Glu Leu
1 5 10

<210> SEQ ID NO 24
<211> LENGTH: 10
<212> TYPE: PRT
<213> ORGANISM: Homo sapiens

<400> SEQUENCE: 24

Leu Leu Leu Glu Pro Ser Ser Leu Thr Ala
1 5 10

<210> SEQ ID NO 25
<211> LENGTH: 10
<212> TYPE: PRT
<213> ORGANISM: Homo sapiens

<400> SEQUENCE: 25

Gly Val Leu Leu Trp Glu Ile Phe Ser Leu
1 5 10

<210> SEQ ID NO 26
<211> LENGTH: 9
<212> TYPE: PRT
<213> ORGANISM: Homo sapiens

<400> SEQUENCE: 26

Lys Pro Thr Lys Lys Asn Asn Pro Ile
1 5

<210> SEQ ID NO 27
<211> LENGTH: 9
<212> TYPE: PRT
<213> ORGANISM: Homo sapiens

<400> SEQUENCE: 27

Arg Pro Ser Gln Pro Ser Ser Leu Ala
1 5

<210> SEQ ID NO 28
<211> LENGTH: 9
<212> TYPE: PRT
<213> ORGANISM: Homo sapiens

<400> SEQUENCE: 28

Leu Pro Arg Phe Ile Leu Leu Glu Leu
1 5

<210> SEQ ID NO 29
<211> LENGTH: 9
<212> TYPE: PRT
<213> ORGANISM: Homo sapiens

<400> SEQUENCE: 29

Arg Pro Arg Pro Ser Gln Pro Ser Ser
1 5

<210> SEQ ID NO 30
<211> LENGTH: 10
<212> TYPE: PRT
<213> ORGANISM: Homo sapiens

<400> SEQUENCE: 30

Arg Pro Ser Gln Pro Ser Ser Leu Ala Met
1 5 10

<210> SEQ ID NO 31
<211> LENGTH: 10
<212> TYPE: PRT
<213> ORGANISM: Homo sapiens

<400> SEQUENCE: 31

Tyr Pro Ser Lys Ser Asn Gln Glu Val Leu
1 5 10

<210> SEQ ID NO 32
<211> LENGTH: 10
<212> TYPE: PRT
<213> ORGANISM: Homo sapiens

<400> SEQUENCE: 32

```
Leu Pro Arg Phe Ile Leu Leu Glu Leu Met
1               5                   10


<210> SEQ ID NO 33
<211> LENGTH: 10
<212> TYPE: PRT
<213> ORGANISM: Homo sapiens

<400> SEQUENCE: 33

Ser Pro Leu Gln Val Ala Val Lys Thr Leu
1               5                   10


<210> SEQ ID NO 34
<211> LENGTH: 9
<212> TYPE: PRT
<213> ORGANISM: Homo sapiens

<400> SEQUENCE: 34

Tyr Tyr Arg Lys Gly Gly Cys Ala Met
1               5


<210> SEQ ID NO 35
<211> LENGTH: 9
<212> TYPE: PRT
<213> ORGANISM: Homo sapiens

<400> SEQUENCE: 35

Val Tyr Glu Gly Gln Val Ser Gly Met
1               5


<210> SEQ ID NO 36
<211> LENGTH: 9
<212> TYPE: PRT
<213> ORGANISM: Homo sapiens

<400> SEQUENCE: 36

Tyr Arg Lys Gly Gly Cys Ala Met Leu
1               5


<210> SEQ ID NO 37
<211> LENGTH: 9
<212> TYPE: PRT
<213> ORGANISM: Homo sapiens

<400> SEQUENCE: 37

Val Tyr Arg Arg Lys His Gln Glu Leu
1               5


<210> SEQ ID NO 38
<211> LENGTH: 9
<212> TYPE: PRT
<213> ORGANISM: Homo sapiens

<400> SEQUENCE: 38

Lys Trp Met Pro Pro Glu Ala Phe Met
1               5


<210> SEQ ID NO 39
<211> LENGTH: 9
<212> TYPE: PRT
<213> ORGANISM: Homo sapiens

<400> SEQUENCE: 39

Val Arg Val Pro Arg Gly Pro Ala Val
```

1 5

<210> SEQ ID NO 40
<211> LENGTH: 9
<212> TYPE: PRT
<213> ORGANISM: Homo sapiens

<400> SEQUENCE: 40

Gly Arg Leu Pro Gly Ala Ser Leu Leu
1 5

<210> SEQ ID NO 41
<211> LENGTH: 10
<212> TYPE: PRT
<213> ORGANISM: Homo sapiens

<400> SEQUENCE: 41

Tyr Tyr Arg Lys Gly Gly Cys Ala Met Leu
1 5 10

<210> SEQ ID NO 42
<211> LENGTH: 10
<212> TYPE: PRT
<213> ORGANISM: Homo sapiens

<400> SEQUENCE: 42

Ser Tyr Tyr Arg Lys Gly Gly Cys Ala Met
1 5 10

<210> SEQ ID NO 43
<211> LENGTH: 10
<212> TYPE: PRT
<213> ORGANISM: Homo sapiens

<400> SEQUENCE: 43

Glu Arg Ser Pro Ala Ala Pro Pro Pro Leu
1 5 10

<210> SEQ ID NO 44
<211> LENGTH: 10
<212> TYPE: PRT
<213> ORGANISM: Homo sapiens

<400> SEQUENCE: 44

Arg Arg Lys His Gln Glu Leu Gln Ala Met
1 5 10

<210> SEQ ID NO 45
<211> LENGTH: 11
<212> TYPE: PRT
<213> ORGANISM: Homo sapiens

<400> SEQUENCE: 45

Glu Arg Ser Ala Pro Ala Ala Pro Pro Pro Leu
1 5 10

<210> SEQ ID NO 46
<211> LENGTH: 10
<212> TYPE: PRT
<213> ORGANISM: Homo sapiens

<400> SEQUENCE: 46

Gly Arg Leu Pro Gly Ala Ser Leu Leu Leu
1 5 10

<210> SEQ ID NO 47
<211> LENGTH: 10
<212> TYPE: PRT
<213> ORGANISM: Homo sapiens

<400> SEQUENCE: 47

Ser Phe Gly Val Leu Leu Trp Glu Ile Phe
1 5 10

<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Val Tyr Arg Arg Lys His Gln Glu Leu Gln Ala Met Gln Met Glu Leu
1 5 10 15

Gln Ser Pro Glu Tyr Lys Leu Ser Lys Leu Arg Thr Ser Thr Ile Met
20 25 30

Thr Asp Tyr Asn
35

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 49

Lys Leu Arg Thr Ser Thr Ile Met Thr Asp Tyr Asn Pro Asn Tyr Cys
1 5 10 15

Phe Ala Gly Lys Thr Ser Ser Ile Ser Asp Leu Lys Glu Val Pro Arg
20 25 30

Lys Asn Ile Thr
35

<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 50

Ser Asp Leu Lys Glu Val Pro Arg Lys Asn Ile Thr Leu Ile Arg Gly
1 5 10 15

Leu Gly His Gly Ala Phe Gly Glu Val Tyr Glu Gly Gln Val Ser Gly
20 25 30

Met Pro Asn Asp
35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

Val Tyr Glu Gly Gln Val Ser Gly Met Pro Asn Asp Pro Ser Pro Leu
1               5                   10                  15

Gln Val Ala Val Lys Thr Leu Pro Glu Val Cys Ser Glu Gln Asp Glu
            20                  25                  30

Leu Asp Phe Leu
        35

<210> SEQ ID NO 52
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Glu Val Cys Ser Glu Gln Asp Glu Leu Asp Phe Leu Met Glu Ala Leu
1               5                   10                  15

Ile Ile Ser Lys Phe Asn His Gln Asn Ile Val Arg Cys Ile Gly Val
            20                  25                  30

Ser Leu Gln Ser
        35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Asn Ile Val Arg Cys Ile Gly Val Ser Leu Gln Ser Leu Pro Arg Phe
1               5                   10                  15

Ile Leu Leu Glu Leu Met Ala Gly Gly Asp Leu Lys Ser Phe Leu Arg
            20                  25                  30

Glu Thr Arg Pro
        35

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gly Asp Leu Lys Ser Phe Leu Arg Glu Thr Arg Pro Arg Pro Ser Gln
1               5                   10                  15

Pro Ser Ser Leu Ala Met Leu Asp Leu Leu His Val Ala Arg Asp Ile
            20                  25                  30

Ala Cys Gly Cys
        35

<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Leu Leu His Val Ala Arg Asp Ile Ala Cys Gly Cys Gln Tyr Leu Glu
1 5 10 15

Glu Asn His Phe Ile His Arg Asp Ile Ala Ala Arg Asn Cys Leu Leu
20 25 30

Thr Cys Pro Gly
35

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

Ile Ala Ala Arg Asn Cys Leu Leu Thr Cys Pro Gly Pro Gly Arg Val
1 5 10 15

Ala Lys Ile Gly Asp Phe Gly Met Ala Arg Asp Ile Tyr Arg Ala Ser
20 25 30

Tyr Tyr Arg Lys
35

<210> SEQ ID NO 57
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

Ala Arg Asp Ile Tyr Arg Ala Ser Tyr Tyr Arg Lys Gly Gly Cys Ala
1 5 10 15

Met Leu Pro Val Lys Trp Met Pro Pro Glu Ala Phe Met Glu Gly Ile
20 25 30

Phe Thr Ser Lys
35

<210> SEQ ID NO 58
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

Pro Glu Ala Phe Met Glu Gly Ile Phe Thr Ser Lys Thr Asp Thr Trp
1 5 10 15

Ser Phe Gly Val Leu Leu Trp Glu Ile Phe Ser Leu Gly Tyr Met Pro
20 25 30

Tyr Pro Ser Lys
35

<210> SEQ ID NO 59
<211> LENGTH: 36
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 59

Ile Phe Ser Leu Gly Tyr Met Pro Tyr Pro Ser Lys Ser Asn Gln Glu
1 5 10 15

Val Leu Glu Phe Val Thr Ser Gly Gly Arg Met Asp Pro Pro Lys Asn
20 25 30

Cys Pro Gly Pro
35

<210> SEQ ID NO 60
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 60

Gly Arg Met Asp Pro Pro Lys Asn Cys Pro Gly Pro Val Tyr Arg Ile
1 5 10 15

Met Thr Gln Cys Trp Gln His Gln Pro Glu Asp Arg Pro Asn Phe Ala
20 25 30

Ile Ile Leu Glu
35

<210> SEQ ID NO 61
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 61

Pro Glu Asp Arg Pro Asn Phe Ala Ile Ile Leu Glu Arg Ile Glu Tyr
1 5 10 15

Cys Thr Gln Asp Pro Asp Val Ile Asn Thr Ala Leu Pro Ile Glu Tyr
20 25 30

Gly Pro Leu Val
35

<210> SEQ ID NO 62
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Asn Thr Ala Leu Pro Ile Glu Tyr Gly Pro Leu Val Glu Glu Glu Glu
1 5 10 15

Lys Val Pro Val Arg Pro Lys Asp Pro Glu Gly Val Pro Pro Leu Leu
20 25 30

Val Ser Gln Gln
35

<210> SEQ ID NO 63
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

Pro Glu Gly Val Pro Pro Leu Leu Val Ser Gln Gln Ala Lys Arg Glu
1 5 10 15

Glu Glu Arg Ser Pro Ala Ala Pro Pro Pro Leu Pro Thr Thr Ser Ser
20 25 30

Gly Lys Ala Ala
35

<210> SEQ ID NO 64
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Pro Pro Leu Pro Thr Thr Ser Ser Gly Lys Ala Ala Lys Lys Pro Thr
1 5 10 15

Ala Ala Glu Ile Ser Val Arg Val Pro Arg Gly Pro Ala Val Glu Gly
20 25 30

Gly His Val Asn
35

<210> SEQ ID NO 65
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Pro Arg Gly Pro Ala Val Glu Gly Gly His Val Asn Met Ala Phe Ser
1 5 10 15

Gln Ser Asn Pro Pro Ser Glu Leu His Lys Val His Gly Ser Arg Asn
20 25 30

Lys Pro Thr Ser
35

<210> SEQ ID NO 66
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

His Lys Val His Gly Ser Arg Asn Lys Pro Thr Ser Leu Trp Asn Pro
1 5 10 15

Thr Tyr Gly Ser Trp Phe Thr Glu Lys Pro Thr Lys Lys Asn Asn Pro
20 25 30

Ile Ala Lys Lys
35

<210> SEQ ID NO 67
<211> LENGTH: 36
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 67

Lys Pro Thr Lys Lys Asn Asn Pro Ile Ala Lys Lys Glu Pro His Asp
1 5 10 15

Arg Gly Asn Leu Gly Leu Glu Gly Ser Cys Thr Val Pro Pro Asn Val
20 25 30

Ala Thr Gly Arg
35

<210> SEQ ID NO 68
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

Ser Cys Thr Val Pro Pro Asn Val Ala Thr Gly Arg Leu Pro Gly Ala
1 5 10 15

Ser Leu Leu Leu Glu Pro Ser Ser Leu Thr Ala Asn Met Lys Glu Val
20 25 30

Pro Leu Phe Arg
35

<210> SEQ ID NO 69
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 69

Leu Thr Ala Asn Met Lys Glu Val Pro Leu Phe Arg Leu Arg His Phe
1 5 10 15

Pro Cys Gly Asn Val Asn Tyr Gly Tyr Gln Gln Gln Gly Leu Pro Leu
20 25 30

Glu Ala Ala Thr
35

<210> SEQ ID NO 70
<211> LENGTH: 36
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Gly Tyr Gln Gln Gln Gly Leu Pro Leu Glu Ala Ala Thr Ala Pro Gly
1 5 10 15

Ala Gly His Tyr Glu Asp Thr Ile Leu Lys Ser Lys Asn Ser Met Asn
20 25 30

Gln Pro Gly Pro
35

<210> SEQ ID NO 71
<211> LENGTH: 9

<212> TYPE: PRT
<213> ORGANISM: Homo sapiens

<400> SEQUENCE: 71

Pro Gly Pro Gly Arg Val Ala Lys Ile
1 5

<210> SEQ ID NO 72
<211> LENGTH: 19
<212> TYPE: PRT
<213> ORGANISM: Homo sapiens

<400> SEQUENCE: 72

Pro Gly Pro Gly Arg Val Ala Lys Ile Gly Asp Phe Gly Met Ala Arg
1 5 10 15

Asp Ile Tyr

<210> SEQ ID NO 73
<211> LENGTH: 19
<212> TYPE: PRT
<213> ORGANISM: Homo sapiens

<400> SEQUENCE: 73

Cys Gly Asn Val Asn Tyr Gly Tyr Gln Gln Gln Gly Leu Pro Leu Glu
1 5 10 15

Ala Ala Thr

<210> SEQ ID NO 74
<211> LENGTH: 8
<212> TYPE: PRT
<213> ORGANISM: Homo sapiens

<400> SEQUENCE: 74

Pro Arg Lys Asn Ile Thr Leu Ile
1 5

<210> SEQ ID NO 75
<211> LENGTH: 70
<212> TYPE: PRT
<213> ORGANISM: Homo sapiens

<400> SEQUENCE: 75

Trp Val Arg Arg Gly Arg Gln Asp Phe Gly Arg Pro Cys Pro Glu Arg
1 5 10 15

Pro Gln Leu Leu Pro Pro Gly Pro Leu Gln Cys Leu Arg Thr Leu Arg
20 25 30

Ser Arg Gly Ala Gly Glu Ser Lys Asp Ala Ala Asn Leu Arg Ser Ala
35 40 45

Gly Ala Gly Ile His Ala Gln Lys Phe Ser Arg Gln Thr Val Arg Ser
50 55 60

Leu Pro Ala Ala Glu Arg
65 70

<210> SEQ ID NO 76
<211> LENGTH: 45
<212> TYPE: PRT
<213> ORGANISM: Homo sapiens

<400> SEQUENCE: 76

Leu Glu Gly Ala Gln Asp Gly Ser Leu Arg Pro Arg Phe Pro Pro Arg
1 5 10 15

```
Pro Gly Arg Arg Ala Trp Arg Ser Gln Lys Glu Arg Lys Arg Arg Pro
            20                  25                  30

Gly Gln Arg Ala Ala Ala Gly Ser Arg Arg Ser Gln Pro
        35                  40                  45


<210> SEQ ID NO 77
<211> LENGTH: 63
<212> TYPE: PRT
<213> ORGANISM: Homo sapiens

<400> SEQUENCE: 77

Lys Leu Gln Arg Leu Glu Ala Ala Pro Arg Gly Asp Arg Pro Gln Leu
1               5                   10                  15

Arg Leu Arg Gly Ala Gly Glu Asp Gly Thr Gln Leu Pro Pro Pro Phe
            20                  25                  30

Asn His Ser Ser Ser Ser Val Pro Ser Ala Ala Ser Tyr Arg Arg Gly
        35                  40                  45

Arg Gly Thr Arg Arg Gly Glu Arg Glu Ala Gln Gly Pro Ser Gln
    50                  55                  60


<210> SEQ ID NO 78
<211> LENGTH: 4
<212> TYPE: PRT
<213> ORGANISM: Homo sapiens

<400> SEQUENCE: 78

Ala Gln Cys Ala
1


<210> SEQ ID NO 79
<211> LENGTH: 14
<212> TYPE: PRT
<213> ORGANISM: Homo sapiens

<400> SEQUENCE: 79

Val Ser Leu Asp Ser Pro Leu Ser Phe Gln Val Cys Phe Ile
1               5                   10


<210> SEQ ID NO 80
<211> LENGTH: 46
<212> TYPE: PRT
<213> ORGANISM: Homo sapiens

<400> SEQUENCE: 80

Thr Pro Ala Arg Leu Arg Ala Val Gly Gly Lys Gln Glu Thr Cys Ala
1               5                   10                  15

His Ala Gln Ser Ser Gly Asp Gln Val Glu Gly Ala Ala Gly Tyr Gln
            20                  25                  30

Gly Leu Phe Arg Ala Ser Ser His Leu Gly Glu Ser Glu Gly
        35                  40                  45


<210> SEQ ID NO 81
<211> LENGTH: 7
<212> TYPE: PRT
<213> ORGANISM: Homo sapiens

<400> SEQUENCE: 81

Gly Trp Ala Arg Arg Ala Val
1               5


<210> SEQ ID NO 82
<211> LENGTH: 1626
```

<212> TYPE: PRT
<213> ORGANISM: Homo sapiens

<400> SEQUENCE: 82

```
Thr Ala Ser Ser Gly Gly Met Gly Ala Ile Gly Leu Leu Trp Leu Leu
1               5                   10                  15

Pro Leu Leu Leu Ser Thr Ala Ala Val Gly Ser Gly Met Gly Thr Gly
            20                  25                  30

Gln Arg Ala Gly Ser Pro Ala Ala Gly Pro Pro Leu Gln Pro Arg Glu
        35                  40                  45

Pro Leu Ser Tyr Ser Arg Leu Gln Arg Lys Ser Leu Ala Val Asp Phe
    50                  55                  60

Val Val Pro Ser Leu Phe Arg Val Tyr Ala Arg Asp Leu Leu Leu Pro
65                  70                  75                  80

Pro Ser Ser Ser Glu Leu Lys Ala Gly Arg Pro Glu Ala Arg Gly Ser
                85                  90                  95

Leu Ala Leu Asp Cys Ala Pro Leu Leu Arg Leu Leu Gly Pro Ala Pro
            100                 105                 110

Gly Val Ser Trp Thr Ala Gly Ser Pro Ala Pro Ala Glu Ala Arg Thr
        115                 120                 125

Leu Ser Arg Val Leu Lys Gly Gly Ser Val Arg Lys Leu Arg Arg Ala
    130                 135                 140

Lys Gln Leu Val Leu Glu Leu Gly Glu Glu Ala Ile Leu Glu Gly Cys
145                 150                 155                 160

Val Gly Pro Pro Gly Glu Ala Ala Val Gly Leu Leu Gln Phe Asn Leu
                165                 170                 175

Ser Glu Leu Phe Ser Trp Trp Ile Arg Gln Gly Glu Gly Arg Leu Arg
            180                 185                 190

Ile Arg Leu Met Pro Glu Lys Lys Ala Ser Glu Val Gly Arg Glu Gly
        195                 200                 205

Arg Leu Ser Ala Ala Ile Arg Ala Ser Gln Pro Arg Leu Leu Phe Gln
    210                 215                 220

Ile Phe Gly Thr Gly His Ser Ser Leu Glu Ser Pro Thr Asn Met Pro
225                 230                 235                 240

Ser Pro Ser Pro Asp Tyr Phe Thr Trp Asn Leu Thr Trp Ile Met Lys
                245                 250                 255

Asp Ser Phe Pro Phe Leu Ser His Arg Ser Arg Tyr Gly Leu Glu Cys
            260                 265                 270

Ser Phe Asp Phe Pro Cys Glu Leu Glu Tyr Ser Pro Pro Leu His Asp
        275                 280                 285

Leu Arg Asn Gln Ser Trp Ser Trp Arg Arg Ile Pro Ser Glu Glu Ala
    290                 295                 300

Ser Gln Met Asp Leu Leu Asp Gly Pro Gly Ala Glu Arg Ser Lys Glu
305                 310                 315                 320

Met Pro Arg Gly Ser Phe Leu Leu Leu Asn Thr Ser Ala Asp Ser Lys
                325                 330                 335

His Thr Ile Leu Ser Pro Trp Met Arg Ser Ser Ser Glu His Cys Thr
            340                 345                 350

Leu Ala Val Ser Val His Arg His Leu Gln Pro Ser Gly Arg Tyr Ile
        355                 360                 365

Ala Gln Leu Leu Pro His Asn Glu Ala Ala Arg Glu Ile Leu Leu Met
    370                 375                 380

Pro Thr Pro Gly Lys His Gly Trp Thr Val Leu Gln Gly Arg Ile Gly
385                 390                 395                 400
```

```
Arg Pro Asp Asn Pro Phe Arg Val Ala Leu Glu Tyr Ile Ser Ser Gly
                405                 410                 415

Asn Arg Ser Leu Ser Ala Val Asp Phe Phe Ala Leu Lys Asn Cys Ser
            420                 425                 430

Glu Gly Thr Ser Pro Gly Ser Lys Met Ala Leu Gln Ser Ser Phe Thr
        435                 440                 445

Cys Trp Asn Gly Thr Val Leu Gln Leu Gly Gln Ala Cys Asp Phe His
    450                 455                 460

Gln Asp Cys Ala Gln Gly Glu Asp Glu Ser Gln Met Cys Arg Lys Leu
465                 470                 475                 480

Pro Val Gly Phe Tyr Cys Asn Phe Glu Asp Gly Phe Cys Gly Trp Thr
                485                 490                 495

Gln Gly Thr Leu Ser Pro His Thr Pro Gln Trp Gln Val Arg Thr Leu
            500                 505                 510

Lys Asp Ala Arg Phe Gln Asp His Gln Asp His Ala Leu Leu Leu Ser
        515                 520                 525

Thr Thr Asp Val Pro Ala Ser Glu Ser Ala Thr Val Thr Ser Ala Thr
    530                 535                 540

Phe Pro Ala Pro Ile Lys Ser Ser Pro Cys Glu Leu Arg Met Ser Trp
545                 550                 555                 560

Leu Ile Arg Gly Val Leu Arg Gly Asn Val Ser Leu Val Leu Val Glu
                565                 570                 575

Asn Lys Thr Gly Lys Glu Gln Gly Arg Met Val Trp His Val Ala Ala
            580                 585                 590

Tyr Glu Gly Leu Ser Leu Trp Gln Trp Met Val Leu Pro Leu Leu Asp
        595                 600                 605

Val Ser Asp Arg Phe Trp Leu Gln Met Val Ala Trp Trp Gly Gln Gly
    610                 615                 620

Ser Arg Ala Ile Val Ala Phe Asp Asn Ile Ser Ile Ser Leu Asp Cys
625                 630                 635                 640

Tyr Leu Thr Ile Ser Gly Glu Asp Lys Ile Leu Gln Asn Thr Ala Pro
                645                 650                 655

Lys Ser Arg Asn Leu Phe Glu Arg Asn Pro Asn Lys Glu Leu Lys Pro
            660                 665                 670

Gly Glu Asn Ser Pro Arg Gln Thr Pro Ile Phe Asp Pro Thr Val His
        675                 680                 685

Trp Leu Phe Thr Thr Cys Gly Ala Ser Gly Pro His Gly Pro Thr Gln
    690                 695                 700

Ala Gln Cys Asn Asn Ala Tyr Gln Asn Ser Asn Leu Ser Val Glu Val
705                 710                 715                 720

Gly Ser Glu Gly Pro Leu Lys Gly Ile Gln Ile Trp Lys Val Pro Ala
                725                 730                 735

Thr Asp Thr Tyr Ser Ile Ser Gly Tyr Gly Ala Ala Gly Gly Lys Gly
            740                 745                 750

Gly Lys Asn Thr Met Met Arg Ser His Gly Val Ser Val Leu Gly Ile
        755                 760                 765

Phe Asn Leu Glu Lys Asp Asp Met Leu Tyr Ile Leu Val Gly Gln Gln
    770                 775                 780

Gly Glu Asp Ala Cys Pro Ser Thr Asn Gln Leu Ile Gln Lys Val Cys
785                 790                 795                 800

Ile Gly Glu Asn Asn Val Ile Glu Glu Glu Ile Arg Val Asn Arg Ser
                805                 810                 815
```

```
Val His Glu Trp Ala Gly Gly Gly Gly Gly Gly Gly Gly Ala Thr Tyr
            820                 825                 830

Val Phe Lys Met Lys Asp Gly Val Pro Val Pro Leu Ile Ile Ala Ala
        835                 840                 845

Gly Gly Gly Gly Arg Ala Tyr Gly Ala Lys Thr Asp Thr Phe His Pro
    850                 855                 860

Glu Arg Leu Glu Asn Asn Ser Ser Val Leu Gly Leu Asn Gly Asn Ser
865                 870                 875                 880

Gly Ala Ala Gly Gly Gly Gly Gly Trp Asn Asp Asn Thr Ser Leu Leu
                885                 890                 895

Trp Ala Gly Lys Ser Leu Gln Glu Gly Ala Thr Gly Gly His Ser Cys
            900                 905                 910

Pro Gln Ala Met Lys Lys Trp Gly Trp Glu Thr Arg Gly Gly Phe Gly
        915                 920                 925

Gly Gly Gly Gly Gly Cys Ser Ser Gly Gly Gly Gly Gly Gly Tyr Ile
    930                 935                 940

Gly Gly Asn Ala Ala Ser Asn Asn Asp Pro Glu Met Asp Gly Glu Asp
945                 950                 955                 960

Gly Val Ser Phe Ile Ser Pro Leu Gly Ile Leu Tyr Thr Pro Ala Leu
                965                 970                 975

Lys Val Met Glu Gly His Gly Glu Val Asn Ile Lys His Tyr Leu Asn
            980                 985                 990

Cys Ser His Cys Glu Val Asp Glu  Cys His Met Asp Pro  Glu Ser His
        995                 1000                1005

Lys Val  Ile Cys Phe Cys Asp  His Gly Thr Val Leu  Ala Glu Asp
    1010                1015                1020

Gly Val  Ser Cys Ile Val Ser  Pro Thr Pro Glu Pro  His Leu Pro
    1025                1030                1035

Leu Ser  Leu Ile Leu Ser Val  Val Thr Ser Ala Leu  Val Ala Ala
    1040                1045                1050

Leu Val  Leu Ala Phe Ser Gly  Ile Met Ile Val Tyr  Arg Arg Lys
    1055                1060                1065

His Gln  Glu Leu Gln Ala Met  Gln Met Glu Leu Gln  Ser Pro Glu
    1070                1075                1080

Tyr Lys  Leu Ser Lys Leu Arg  Thr Ser Thr Ile Met  Thr Asp Tyr
    1085                1090                1095

Asn Pro  Asn Tyr Cys Phe Ala  Gly Lys Thr Ser Ser  Ile Ser Asp
    1100                1105                1110

Leu Lys  Glu Val Pro Arg Lys  Asn Ile Thr Leu Ile  Arg Gly Leu
    1115                1120                1125

Gly His  Gly Ala Phe Gly Glu  Val Tyr Glu Gly Gln  Val Ser Gly
    1130                1135                1140

Met Pro  Asn Asp Pro Ser Pro  Leu Gln Val Ala Val  Lys Thr Leu
    1145                1150                1155

Pro Glu  Val Cys Ser Glu Gln  Asp Glu Leu Asp Phe  Leu Met Glu
    1160                1165                1170

Ala Leu  Ile Ile Ser Lys Phe  Asn His Gln Asn Ile  Val Arg Cys
    1175                1180                1185

Ile Gly  Val Ser Leu Gln Ser  Leu Pro Arg Phe Ile  Leu Leu Glu
    1190                1195                1200

Leu Met  Ala Gly Gly Asp Leu  Lys Ser Phe Leu Arg  Glu Thr Arg
    1205                1210                1215

Pro Arg  Pro Ser Gln Pro Ser  Ser Leu Ala Met Leu  Asp Leu Leu
```

```
    1220                1225                1230

His Val  Ala Arg Asp Ile Ala  Cys Gly Cys Gln Tyr  Leu Glu Glu
    1235                1240                1245

Asn His  Phe Ile His Arg Asp  Ile Ala Ala Arg Asn  Cys Leu Leu
    1250                1255                1260

Thr Cys  Pro Gly Pro Gly Arg  Val Ala Lys Ile Gly  Asp Phe Gly
    1265                1270                1275

Met Ala  Arg Asp Ile Tyr Arg  Ala Ser Tyr Tyr Arg  Lys Gly Gly
    1280                1285                1290

Cys Ala  Met Leu Pro Val Lys  Trp Met Pro Pro Glu  Ala Phe Met
    1295                1300                1305

Glu Gly  Ile Phe Thr Ser Lys  Thr Asp Thr Trp Ser  Phe Gly Val
    1310                1315                1320

Leu Leu  Trp Glu Ile Phe Ser  Leu Gly Tyr Met Pro  Tyr Pro Ser
    1325                1330                1335

Lys Ser  Asn Gln Glu Val Leu  Glu Phe Val Thr Ser  Gly Gly Arg
    1340                1345                1350

Met Asp  Pro Pro Lys Asn Cys  Pro Gly Pro Val Tyr  Arg Ile Met
    1355                1360                1365

Thr Gln  Cys Trp Gln His Gln  Pro Glu Asp Arg Pro  Asn Phe Ala
    1370                1375                1380

Ile Ile  Leu Glu Arg Ile Glu  Tyr Cys Thr Gln Asp  Pro Asp Val
    1385                1390                1395

Ile Asn  Thr Ala Leu Pro Ile  Glu Tyr Gly Pro Leu  Val Glu Glu
    1400                1405                1410

Glu Glu  Lys Val Pro Val Arg  Pro Lys Asp Pro Glu  Gly Val Pro
    1415                1420                1425

Pro Leu  Leu Val Ser Gln Gln  Ala Lys Arg Glu Glu  Glu Arg Ser
    1430                1435                1440

Pro Ala  Ala Pro Pro Pro Leu  Pro Thr Thr Ser Ser  Gly Lys Ala
    1445                1450                1455

Ala Lys  Lys Pro Thr Ala Ala  Glu Ile Ser Val Arg  Val Pro Arg
    1460                1465                1470

Gly Pro  Ala Val Glu Gly Gly  His Val Asn Met Ala  Phe Ser Gln
    1475                1480                1485

Ser Asn  Pro Pro Ser Glu Leu  His Lys Val His Gly  Ser Arg Asn
    1490                1495                1500

Lys Pro  Thr Ser Leu Trp Asn  Pro Thr Tyr Gly Ser  Trp Phe Thr
    1505                1510                1515

Glu Lys  Pro Thr Lys Lys Asn  Asn Pro Ile Ala Lys  Lys Glu Pro
    1520                1525                1530

His Asp  Arg Gly Asn Leu Gly  Leu Glu Gly Ser Cys  Thr Val Pro
    1535                1540                1545

Pro Asn  Val Ala Thr Gly Arg  Leu Pro Gly Ala Ser  Leu Leu Leu
    1550                1555                1560

Glu Pro  Ser Ser Leu Thr Ala  Asn Met Lys Glu Val  Pro Leu Phe
    1565                1570                1575

Arg Leu  Arg His Phe Pro Cys  Gly Asn Val Asn Tyr  Gly Tyr Gln
    1580                1585                1590

Gln Gln  Gly Leu Pro Leu Glu  Ala Ala Thr Ala Pro  Gly Ala Gly
    1595                1600                1605

His Tyr  Glu Asp Thr Ile Leu  Lys Ser Lys Asn Ser  Met Asn Gln
    1610                1615                1620
```

```
Pro Gly  Pro
    1625


<210> SEQ ID NO 83
<211> LENGTH: 40
<212> TYPE: PRT
<213> ORGANISM: Homo sapiens

<400> SEQUENCE: 83

Ala Arg Ser His Thr His Phe Ser Ser Leu Gly Ser Leu Arg Pro Trp
1               5                   10                  15

Arg Arg Glu Arg Gln Trp Leu Leu His Lys Pro Glu Thr Lys Cys His
            20                  25                  30

Val Leu Phe Cys Ala Asn Leu Phe
        35                  40


<210> SEQ ID NO 84
<211> LENGTH: 8
<212> TYPE: PRT
<213> ORGANISM: Homo sapiens

<400> SEQUENCE: 84

Ser Thr Thr Lys Lys Ala Val Phe
1               5


<210> SEQ ID NO 85
<211> LENGTH: 24
<212> TYPE: PRT
<213> ORGANISM: Homo sapiens

<400> SEQUENCE: 85

Lys Cys Phe Arg Lys Val Leu Ser Met Gly Ser Ser Tyr Ser Phe Glu
1               5                   10                  15

Arg Arg Lys Tyr His Lys Asn Glu
            20


<210> SEQ ID NO 86
<211> LENGTH: 8
<212> TYPE: PRT
<213> ORGANISM: Homo sapiens

<400> SEQUENCE: 86

Ile Gln Gly Pro Asp Val Val Ala
1               5


<210> SEQ ID NO 87
<211> LENGTH: 26
<212> TYPE: PRT
<213> ORGANISM: Homo sapiens

<400> SEQUENCE: 87

Gly Phe Tyr Ala Cys Leu Leu Tyr Thr Ser Leu Cys Phe Phe Gln Ile
1               5                   10                  15

Val Cys Ala Leu Leu Gln Cys Ser Gln Asn
            20                  25


<210> SEQ ID NO 88
<211> LENGTH: 16
<212> TYPE: PRT
<213> ORGANISM: Homo sapiens

<400> SEQUENCE: 88
```

-continued

```
Leu Leu Leu Cys Phe Ile Val Gly Val Ile Asp Val Ser Leu Pro Cys
1               5                   10                  15


<210> SEQ ID NO 89
<211> LENGTH: 20
<212> TYPE: PRT
<213> ORGANISM: Homo sapiens

<400> SEQUENCE: 89

Cys Gly His Glu Pro Phe Glu Gly Arg Gly Asn Gly Asn Lys Gly Val
1               5                   10                  15

Ile Cys Asn Asp
            20
```

ANAPLASTIC LYMPHOMA KINASE (ALK) CANCER VACCINE AND METHODS OF USE

CROSS REFERENCE TO RELATED APPLICATIONS

This application is the U.S. National Stage Application, pursuant to 35 U.S.C. § 371 of PCT International Application No. PCT/US2020/051237, filed Sep. 17, 2020 designating the United States and published in English, which claims priority to and the benefit of U.S. Provisional Application No. 62/902,096, filed Sep. 18, 2019, the contents of each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Nov. 23, 2020, is named 167705-011601_PCT_SL.txt and is 116,614 bytes in size.

BACKGROUND OF THE INVENTION

Anaplastic lymphoma kinase (ALK) is a receptor tyrosine kinase in the insulin receptor superfamily, which plays an important role in the development of the brain and nervous system. ALK is processed into peptides by the proteasome, transported to the endoplasmic reticulum by transporters associated with antigen processing-1 and -2 (TAP1 and TAP2), and binds to the HLA class I molecules. ALK is minimally expressed by normal tissues during adulthood. However, ALK is aberrantly expressed by tumors, such as non-small cell lung cancer (NSCLC), anaplastic large cell lymphoma (ALCL) and neuroblastoma. More rarely, ALK is expressed by B-cell lymphoma, thyroid cancer, colon cancer, breast cancer, inflammatory myofibroblastic tumors (IMT), renal carcinoma, esophageal cancer, and melanoma. Thus, ALK is an ideal shared antigen across different type of cancers. ALK may become oncogenic by forming a fusion gene with other genes, by gaining additional gene copies, or by genetic mutations. For example, a 2; 5 chromosomal translocation creates a fusion gene consisting of the ALK gene and the nucleophosmin (NPM) gene. The NPM-ALK translocation is associated with approximately 60% anaplastic large-cell lymphomas (ALCLs).

Lung cancer is the most common cause of cancer-related death worldwide, and the annual incidence of ALK-positive non-small cell lung cancers (NSCLCs) in the U.S. is about 8,000 cases. EML4-ALK positive lung cancer is a primary malignant lung tumor where the echinoderm microtubule-associate protein-like 4 (EML4) gene is fused to the ALK gene. About 3-7% of NSCLCs harbor an EML4-ALK-rearrangement in the ALK gene.

Several ALK tyrosine kinase inhibitors (TKIs) are available for the treatment of ALK-rearranged NSCLC, including crizotinib, ceritinib, alectinib, brigatinib, and lorlatinib. Unfortunately, resistance to these drugs occurs within 1-2 years through a variety of mechanisms. Once patients develop resistance to available ALK inhibitors, they are typically treated with cytotoxic chemotherapy rather than immunotherapy since response rates to PD-1 pathway inhibitors in this population are very low. Although PD-1 inhibitors such as pembrolizumab (KEYTRUDA®) and nivolumab (OPDIVO®) have revolutionized the treatment of lung cancer in general, particularly in smoking-associated cancers, most patients with ALK-positive lung cancer do not respond to these immunotherapies. Thus, the development of additional ALK-targeted therapy in ALK-positive NSCLCs and other tumors is clearly a need.

INCORPORATION BY REFERENCE

All publications, patents, and patent applications mentioned in this specification are herein incorporated by reference to the same extent as if each individual publication, patent, or patent application was specifically and individually indicated to be incorporated by reference. Absent any indication otherwise, publications, patents, and patent applications mentioned in this specification are incorporated herein by reference in their entireties

SUMMARY OF THE INVENTION

As described below, the present invention features isolated anaplastic lymphoma kinase (ALK) peptides that are fragments of the cytoplasmic portion of an ALK protein shared by cancers having an ALK rearrangement and cancers expressing the ALK protein, that bind a human leukocyte antigen (HLA), and elicit an immune response against one or more ALK-positive cancers. The isolated ALK peptides may be modified with an amphiphilic conjugate to increase T-cell expansion and greatly enhance anti-tumor efficacy. Also provided are polynucleotides encoding isolated ALK peptides, vaccines comprising an isolated ALK peptide or polynucleotide, immunogenic compositions thereof, and kits for administering the same. Methods of treatment and methods of generating an immune response in a subject by administering the ALK-specific peptide antigens, immunogens, vaccines, or immunogenic compositions thereof are provided.

In one aspect, the invention provides an isolated anaplastic lymphoma kinase (ALK) peptide wherein the peptide: i) is a fragment of the cytoplasmic portion of an ALK protein shared by cancers having an ALK rearrangement and cancers expressing the ALK protein; ii) is capable of binding a human leukocyte antigen (HLA); and iii) is capable of generating an immune response against one or more ALK-positive cancers, wherein the peptide does not include the amino acid sequence AMLDLLHVA (SEQ ID NO: 1). In some embodiments, the ALK peptide is capable of generating an immune response against one or more ALK-positive cancers, wherein the ALK peptide comprises the amino acid sequence RPRPSQPSSL (SEQ ID NO: 2). In some embodiments, the ALK peptide is capable of generating an immune response against one or more ALK-positive cancers, wherein the ALK peptide comprises the amino acid sequence IVRCIGVSL (SEQ ID NO: 3). In some embodiments, the ALK peptide is capable of generating an immune response against one or more ALK-positive cancers, wherein the ALK peptide comprises the amino acid sequence VPRKNITLI (SEQ ID NO: 4). In some embodiments, the ALK peptide is capable of generating an immune response against one or more ALK-positive cancers, wherein the ALK peptide comprises the amino acid sequence TAAEVSVRV (SEQ ID NO: 5).

In some embodiments, the peptide comprises an amino acid sequence that has at least about 95% identity to a sequence listed in Table 3, Table 4, or Table 5. In some embodiments, the peptide comprises or consists of an amino acid sequence selected from those listed in Table 3, Table 4, or Table 5. In some embodiments, the peptide comprises an amino acid sequence that has at least about 95% identity to an amino acid sequence selected from the following: RPRPSQPSSL (SEQ ID NO: 2); IVRCIGVSL (SEQ ID NO: 3); VPRKNITLI (SEQ ID NO: 4); or TAAEVSVRV (SEQ ID NO: 5).

In some embodiments, the ALK antigen is conjugated to an amphiphile. In some embodiments, the amphiphile is N-hydroxy succinimidyl ester-end-functionalized poly(ethylene glycol)-lipid (NHS-PEG2KDa-DSPE). In some embodiments, the one or more ALK-positive cancers is selected from the group consisting of non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, and melanoma. In some embodiments, the one or more ALK-positive cancers is non-small cell lung cancer (NSCLC). In some embodiments, the one or more ALK-positive cancers is anaplastic large cell lymphoma (ALCL).

In some embodiments, the HLA is encoded by a HLA class I allele. In some embodiments, the HLA class I allele is selected from those listed in Table 1, Table 2, or Table 3. In some embodiments, the HLA class I allele is HLA A*02:01, HLA A*68:02, HLA B*07:02, or HLA C*07:02. In some embodiments, the ALK protein is a full-length human ALK protein. In some embodiments, the ALK rearrangement is a nucleophosmin-ALK rearrangement (NPM-ALK) or an echinoderm microtubule-associate protein-like 4-ALK rearrangement (EML4-ALK).

In one aspect, the invention provides a polynucleotide encoding for an ALK peptide. In another aspect, the invention provides a vaccine comprising a polynucleotide encoding for an ALK peptide. In yet another aspect, the invention provides a vaccine comprising an ALK peptide.

In one aspect, the invention provides a vaccine comprising two or more isolated synthetic anaplastic lymphoma kinase (ALK) peptides capable of generating an immune response against one or more ALK-positive cancers, wherein the two or more isolated ALK peptides are selected from those listed in Table 3, Table 4, or Table 5. In one embodiment, the two or more ALK peptides comprise two or more amino acid sequences selected from the following: AMLDLLHVA (SEQ ID NO: 1); RPRPSQPSSL (SEQ ID NO: 2); IVRCIGVSL (SEQ ID NO: 3); VPRKNITLI (SEQ ID NO: 4); and/or TAAEVSVRV (SEQ ID NO: 5). In some embodiments, the two or more ALK peptides comprise at least one of the following combinations: AMLDLLHVA (SEQ ID NO: 1) and RPRPSQPSSL (SEQ ID NO: 2); AMLDLLHVA (SEQ ID NO: 1) and IVRCIGVSL (SEQ ID NO: 3); AMLDLLHVA (SEQ ID NO: 1) and VPRKNITLI (SEQ ID NO: 4); AMLDLLHVA (SEQ ID NO: 1) and TAAEVSVRV (SEQ ID NO: 5); RPRPSQPSSL (SEQ ID NO: 2) and IVRCIGVSL (SEQ ID NO: 3); RPRPSQPSSL (SEQ ID NO: 2) and VPRKNITLI (SEQ ID NO: 4); RPRPSQPSSL (SEQ ID NO: 2) and TAAEVSVRV (SEQ ID NO: 5); IVRCIGVSL (SEQ ID NO: 3) and VPRKNITLI (SEQ ID NO: 4); IVRCIGVSL (SEQ ID NO: 3) and TAAEVSVRV (SEQ ID NO: 5); VPRKNITLI (SEQ ID NO: 4) and TAAEVSVRV (SEQ ID NO: 5); AMLDLLHVA (SEQ ID NO: 1) and RPRPSQPSSL (SEQ ID NO: 2) and IVRCIGVSL (SEQ ID NO: 3); AMLDLLHVA (SEQ ID NO: 1) and RPRPSQPSSL (SEQ ID NO: 2) and VPRKNITLI (SEQ ID NO: 4); AMLDLLHVA (SEQ ID NO: 1) and RPRPSQPSSL (SEQ ID NO: 2) and TAAEVSVRV (SEQ ID NO: 5); AMLDLLHVA (SEQ ID NO: 1) and IVRCIGVSL (SEQ ID NO: 3) and VPRKNITLI (SEQ ID NO: 4); AMLDLLHVA (SEQ ID NO: 1) and IVRCIGVSL (SEQ ID NO: 3) and TAAEVSVRV (SEQ ID NO: 5); AMLDLLHVA (SEQ ID NO: 1) and VPRKNITLI (SEQ ID NO: 4) and TAAEVSVRV (SEQ ID NO: 5); RPRPSQPSSL (SEQ ID NO: 2) and IVRCIGVSL (SEQ ID NO: 3) and VPRKNITLI (SEQ ID NO: 4); RPRPSQPSSL (SEQ ID NO: 2); IVRCIGVSL (SEQ ID NO: 3) and TAAEVSVRV (SEQ ID NO: 5); RPRPSQPSSL (SEQ ID NO: 2) and VPRKNITLI (SEQ ID NO: 4) and TAAEVSVRV (SEQ ID NO: 5); IVRCIGVSL (SEQ ID NO: 3) and VPRKNITLI (SEQ ID NO: 4) and TAAEVSVRV (SEQ ID NO: 5); AMLDLLHVA (SEQ ID NO: 1) and RPRPSQPSSL (SEQ ID NO: 2) and IVRCIGVSL (SEQ ID NO: 3) and VPRKNITLI (SEQ ID NO: 4); AMLDLLHVA (SEQ ID NO: 1) and RPRPSQPSSL (SEQ ID NO: 2) and IVRCIGVSL (SEQ ID NO: 3) and TAAEVSVRV (SEQ ID NO: 5); AMLDLLHVA (SEQ ID NO: 1) and IVRCIGVSL (SEQ ID NO: 3) and VPRKNITLI (SEQ ID NO: 4) and TAAEVSVRV (SEQ ID NO: 5); AMLDLLHVA (SEQ ID NO: 1) and RPRPSQPSSL (SEQ ID NO: 2) and VPRKNITLI (SEQ ID NO: 4) and TAAEVSVRV (SEQ ID NO: 5); RPRPSQPSSL (SEQ ID NO: 2) and IVRCIGVSL (SEQ ID NO: 3) and VPRKNITLI (SEQ ID NO: 4) and TAAEVSVRV (SEQ ID NO: 5); and/or AMLDLLHVA (SEQ ID NO: 1) and RPRPSQPSSL (SEQ ID NO: 2) and IVRCIGVSL (SEQ ID NO: 3) and VPRKNITLI (SEQ ID NO: 4) and TAAEVSVRV (SEQ ID NO: 5).

In another embodiment, at least one of the two or more ALK peptides is conjugated to an amphiphile. In another embodiment, the amphiphile is N-hydroxy succinimidyl ester-end-functionalized poly(ethylene glycol)-lipid (NHS-PEG2KDa-DSPE).

In one aspect, the invention provides an immunogenic composition comprising a vaccine and a pharmaceutically acceptable carrier, diluent, or excipient. In one embodiment, the immunogenic composition further comprises an adjuvant. In some embodiments, the adjuvant is a synthetic complex of carboxymethvlcellulose, polyinosinic-polycytidylic acid, and poly-L-lysine double-stranded RNA (poly ICLC) or CpG oligonucleotides. In some embodiments, the adjuvant is conjugated to an amphiphile. In some embodiments, the amphiphile is N-hydroxy succinimidyl ester-end-functionalized poly(ethylene glycol)-lipid (NHS-PEG2KDa-DSPE).

In one aspect, the invention provides a method of treating an ALK-positive cancer in a subject by administering to the subject an effective amount of an ALK peptide, vaccine, or immunogenic composition. In another aspect, the invention provides a method of treating a subject with one or more an ALK-positive cancers by administering to the subject an effective amount of an ALK peptide, vaccine, or immunogenic composition. In some embodiments, the methods of treating further comprise administering, simultaneously or sequentially, to the subject an effective amount of one or more of an ALK inhibitor, immune checkpoint inhibitor, and/or tyrosine kinase inhibitor (TKI). In some embodiments, the immune checkpoint inhibitor is selected from one or more of a programmed cell death protein 1 (PD-1) inhibitor, programmed death-ligand 1 (PD-L1) inhibitor, or cytotoxic T-lymphocyte-associated antigen-4 (CTLA-4) inhibitor. In some embodiments, the PD-1 inhibitor is an anti-PD1 antibody. In some embodiments, the ALK inhibitor is lorlatinib. In some embodiments, an anti-PD1 antibody is administered in combination with lorlatinib. In some embodiments, an adjuvant is concomitantly administered to the subject.

In some embodiments, the ALK-positive cancer is selected from the group consisting of non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, and melanoma. In some embodiments, the ALK-positive cancer is non-small cell lung cancer (NSCLC). In some embodiments, the ALK-positive cancer is anaplastic large cell lymphoma (ALCL).

In some embodiments, the subject had at least one prior treatment with at least one tyrosine kinase inhibitor (TKI). In some embodiments, the step of administering comprises one or more doses of the ALK peptide, the vaccine, or the immunogenic composition. In some embodiments, the step of administering comprises at least six (6) prime doses and at least two (2) booster doses of the ALK peptide, the vaccine, or the immunogenic composition.

In one aspect, the invention provides a method of generating an immune response in a subject by administering to the subject an effective amount of an ALK peptide, vaccine, or immunogenic composition. In some embodiments, the immune response produces T-lymphocytes.

In another aspect, the invention provides a kit comprising an agent for administration to a subject with one or more ALK-positive cancers, wherein the agent comprises an ALK peptide, vaccine, or immunogenic composition.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention pertains or relates. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); Benjamin Lewin, Genes V, published by Oxford University Press, 1994 (ISBN 0-19-854287-9); Kendrew et al. (eds.); *The Encyclopedia of Molecular Biology*, published by Blackwell Science Ltd., 1994 (ISBN 0-632-02182-9); *Molecular Biology and Biotechnology: a Comprehensive Desk Reference*, Robert A. Meyers (ed.), published by VCH Publishers, Inc., 1995 (ISBN 1-56081-569-8); and Hale & Marham, *The Harper Collins Dictionary of Biology* (1991). As used herein, the following terms have the meanings ascribed to them below, unless specified otherwise.

By "adjuvant" is meant a substance or vehicle that non-specifically enhances the immune response to an antigen. Adjuvants may include a suspension of minerals (e.g., alum, aluminum hydroxide, or phosphate) on which antigen is adsorbed; or water-in-oil emulsion in which antigen solution is emulsified in mineral oil (e.g., Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (see, e.g., U.S. Pat. Nos. 6,194,388; 6,207,646; 6,214,806; 6,218,371; 6,239,116; 6,339,068; 6,406,705; and 6,429,199). Adjuvants also include biological molecules, such as costimulatory molecules. Exemplary biological adjuvants include, without limitation, interleukin-1 (IL-2), the protein memory T-cell attractant "Regulated on Activation, Normal T Expressed and Secreted" (RANTES), granulocyte-macrophage-colony stimulating factor (GM-CSF), tumor necrosis factor-alpha (TNF-α), interferon-gamma (IFN-γ), granulocyte-colony stimulation factor (G-CSF), lymphocyte function-associated antigen 3 (LFA-3, also called CD58), cluster of differentiation antigen 72 (CD72), (a negative regulator of B-cell responsiveness), peripheral membrane protein, B7-1 (B7-1, also called CD80), peripheral membrane protein, B7-2 (B7-2, also called CD86), the TNF ligand superfamily member 4 ligand (OX40L) or the type 2 transmembrane glycoprotein receptor belonging to the TNF superfamily (4-1BBL). In some embodiments, the adjuvant may be conjugated to an amphiphile as described in H. Liu et al., Structure-based programming of lymph-node targeting in molecular vaccines. Nature 507, 5199522 (2014). In some embodiments, the amphiphile conjugated to the adjuvant is N-hydroxy succinimidyl ester-end-functionalized poly(ethylene glycol)-lipid (NHS-PEG2KDa-DSPE).

By "administer" is meant giving, supplying, or dispensing a composition, agent, therapeutic and the like to a subject, or applying or bringing the composition and the like into contact with the subject. Administering or administration may be accomplished by any of a number of routes, such as, for example, without limitation, topical, oral, subcutaneous, intramuscular, intraperitoneal, intravenous (IV), injection, intrathecal, intramuscular, dermal, intradermal, intracranial, inhalation, rectal, intravaginal, or intraocular.

By "agent" is meant any small molecule chemical compound, antibody, nucleic acid molecule, peptide, polypeptide, or fragments thereof.

By "ALK polypeptide" or "ALK peptide" is meant a protein or fragment thereof having an amino acid sequence that is at least 85%, at least 90%, at least 95%, at least 98%, at least 99%, or 100% identical to an anaplastic lymphoma kinase (ALK) amino acid sequence associated with GenBank Accession No.: BAD92714.1, ACY79563, or ACI47591, which is capable of inducing an ALK-specific immune response in an immunized subject. In some embodiments, the ALK polypeptide is at least 85%, at least 90%, at least 95%, at least 98%, at least 99%, or 100% identical to the ALK protein in *Homo Sapiens*. An exemplary ALK full-length amino acid sequence from *Homo Sapiens* is provided below (ALK cytoplasmic portion in bold font):

```
                                       (SEQ ID NO: 6)
TASSGGMGAIGLLWLLPLLLSTAAVGSGMGTGQRAGSPAAGPPLQPREPL

SYSRLQRKSLAVDEVVPSLFRVYARDLLLPPSSSELKAGRPEARGSLALD

CAPLLRLLGPAPGVSWTAGSPAPAEARTLSRVLKGGSVRKLRRAKQLVLE

LGEEAILEGCVGPPGEAAVGLLQFNLSELFSWWIRQGEGRLRIRLMPEKK

ASEVGREGRLSAAIRASQPRLLFQIFGTGHSSLESPTNMPSPSPDYFTWN

LTWIMKDSFPFLSHRSRYGLECSFDFPCELEYSPPLHDLRNQSWSWRRIP

SEEASQMDLLDGPGAERSKEMPRGSFLLLNTSADSKHTILSPWMRSSSEH

CTLAVSVHRHLQPSGRYIAQLLPHNEAAREILLMPTPGKHGWTVLQGRIG

RPDNPFRVALEYISSGNRSLSAVDFFALKNCSEGTSPGSKMALQSSFTCW

NGTVLQLGQACDFHQDCAQGEDESQMCRKLPVGFYCNFEDGFCGWTQGTL

SPHTPQWQVRTLKDARFQDHQDHALLLSTTDVPASESATVTSATFPAPIK

SSPCELRMSWLIRGVLRGNVSLVLVENKTGKEQGRWWHVAAYEGLSLWQW

MVLPLLDVSDRFWLQMVAWWGQGSRAIVAFDNISISLDCYLTISGEDKIL
```

-continued

QNTAPKSRNLFERNPNKELKPGENSPRQTPIFDPTVHWLFTTCGASGPHG

PTQAQCNNAYQNSNLSVEVGSEGPLKGIQIWKVPATDTYSISGYGAAGGK

GGKNTMMRSHGVSVLGIFNLEKDDMLYILVGQQGEDACPSTNQLIQKVCI

GENNVIEEEIRVNRSVHEWAGGGGGGGGATYVFKMKDGVPVPLIIAAGGG

GRAYGAKTDTFHPERLENNSSVLGLNGNSGAAGGGGGWNDNTSLLWAGKS

LQEGATGGHSCPQAMKKWGWETRGGFGGGGGGCSSGGGGGGYIGGNAASN

NDPEMDGEDGVSFISPLGILYTPALKVMEGHGEVNIKHYLNCSHCEVDEC

HMDPESHKVICFCDHGTVLAEDGVSCIVSPTPEPHLPLSLILSVVTSALV

AALVLAFSGIMIVYRRKHQELQAMQMELQSPEYKLSKLRTSTIMTDYNPN

YCFAGKTSSISDLKEVPRKNITLIRGLGHGAFGEVYEGQVSGMPNDPSPL

-continued

QVAVKTLPEVCSEQDELDFLMEALIISKFNHQNIVRCIGVSLQSLPRFIL

LELMAGGDLKSFLRETRPRPSQPSSLAMLDLLHVARDIACGCQYLEENHF

IHRDIAARNCLLTCPGPGRVAKIGDFGMARDIYRASYYRKGGCAMLPVKW

MPPEAFMEGIFTSKTDTWSFGVLLWEIFSLGYMPYPSKSNQEVLEFVTSG

GRMDPPKNCPGPVYRIMTQCWQHQPEDRPNFAIILERIEYCTQDPDVINT

ALPIEYGPLVEEEEKVPVRPKDPEGVPPLLVSQQAKREEERSPAAPPPLP

TTSSGKAAKKPTAAEISVRVPRGPAVEGGHVNMAFSQSNPPSELHKVHGS

RNKPTSLWNPTYGSWFTEKPTKKNNPIAKKEPHDRGNLGLEGSCTVPPNV

ATGRLPGASLLLEPSSLTANMKEVPLFRLRHFPCGNVNYGYQQQGLPLEA

ATAPGAGHYEDTILKSKNSMNQPGP

An exemplary full-length ALK amino acid sequence from *Homo Sapiens* is provided below:

(SEQ ID NOS 7 and 75-89, respectively, in order of appearance)

G A A A V V A A G T S R R L C S E G R G

A P R C F P A A L W S A T Q S R G R * *

W V R R G R Q D F G R P C P E R P Q L L

P P G P L Q C L R T L R S R G A G E S K

D A A N L R S A G A G I H A Q K F S R Q

T V R S L P A A E R * L E G A Q D G S L

R P R F P P R P G R R A W R S Q K E R K

R R P G Q R A A A G S R R S Q P * K L Q

R L E A A P R G D R P Q L R L R G A G E

D G T Q L P P P F N H S S S S V P S A A

S Y R R G R G T R R G E R E A Q G P S Q

* A Q C A * V S L D S P L S F Q V C F I

* T P A R L R A V G G K Q E T C A H A Q

S S G D Q V E G A A G Y Q G L F R A S S

H L G E S E G * G W A R R A V * T A S S

G G M G A I G L L W L L P L L L S T A A

V G S G M G T G Q R A G S P A A G P P L

Q P R E P L S Y S R L Q R K S L A V D F

V V P S L F R V Y A R D L L L P P S S S

E L K A G R P E A R G S L A L D C A P L

L R L L G P A P G V S W T A G S P A P A

E A R T L S R V L K G G S V R K L R R A

K Q L V L E L G E E A I L E G C V G P P

G E A A V G L L Q F N L S E L F S W W I

R Q G E G R L R I R L M P E K K A S E V

G R E G R L S A A I R A S Q P R L L F Q

I F G T G H S S L E S P T N M P S P S P

D Y F T W N L T W I M K D S F P F L S H

-continued

R S R Y G L E C S F D F P C E L E Y S P

P L H D L R N Q S W S W R R I P S E E A

S Q M D L L D G P G A E R S K E M P R G

S F L L L N T S A D S K H T I L S P W M

R S S S E H C T L A V S V H R H L Q P S

G R Y I A Q L L P H N E A A R E I L L M

P T P G K H G W T V L Q G R I G R P D N

P F R V A L E Y I S S G N R S L S A V D

F F A L K N C S E G T S P G S K M A L Q

S S F T C W N G T V L Q L G Q A C D F H

Q D C A Q G E D E S Q M C R K L P V G F

Y C N F E D G F C G W T Q G T L S P H T

P Q W Q V R T L K D A R F Q D H Q D H A

L L L S T T D V P A S E S A T V T S A T

F P A P I K S S P C E L R M S W L I R G

V L R G N V S L V L V E N K T G K E Q G

R M V W H V A A Y E G L S L W Q W M V L

P L L D V S D R F W L Q M V A W W G Q G

S R A I V A F D N I S I S L D C Y L T I

S G E D K I L Q N T A P K S R N L F E R

N P N K E L K P G E N S P R Q T P I F D

P T V H W L F T T C G A S G P H G P T Q

A Q C N N A Y Q N S N L S V E V G S E G

P L K G I Q I W K V P A T D T Y S I S G

Y G A A G G K G G K N T M M R S H G V S

V L G I F N L E K D D M L Y I L V G Q Q

G E D A C P S T N Q L I Q K V C I G E N

N V I E E E I R V N R S V H E W A G G G

G G G G G A T Y V F K M K D G V P V P L

I I A A G G G R A Y G A K T D T F H P

E R L E N N S S V L G L N G N S G A A G

G G G G W N D N T S L L W A G K S L Q E

G A T G G H S C P Q A M K K W G W E T R

G G F G G G G G G C S S G G G G G G Y I

G G N A A S N N D P E M D G E D G V S F

I S P L G I L Y T P A L K V M E G H G E

V N I K H Y L N C S H C E V D E C H M D

P E S H K V I C F C D H G T V L A E D G

V S C I V S P T P E P H L P L S L I L S

V V T S A L V A A L V L A F S G I M I V

-continued

Y R R K H Q E L Q A M Q M E L Q S P E Y

K L S K L R T S T I M T D Y N P N Y C F

A G K T S S I S D L K E V P R K N I T L

I R G L G H G A F G E V Y E G Q V S G M

P N D P S P L Q V A V K T L P E V C S E

Q D E L D F L M E A L I I S K F N H Q N

I V R C I G V S L Q S L P R F I L L E L

M A G G D L K S F L R E T R P R P S Q P

S S L A M L D L L H V A R D I A C G C Q

Y L E E N H F I H R D I A A R N C L L T

C P G P G R V A K I G D F G M A R D I Y

R A S Y Y R K G G C A M L P V K W M P P

E A F M E G I F T S K T D T W S F G V L

L W E I F S L G Y M P Y P S K S N Q E V

L E F V T S G G R M D P P K N C P G P V

Y R I M T Q C W Q H Q P E D R P N F A I

I L E R I E Y C T Q D P D V I N T A L P

I E Y G P L V E E E E K V P V R P K D P

E G V P P L L V S Q Q A K R E E E R S P

A A P P P L P T T S S G K A A K K P T A

A E I S V R V P R G P A V E G G H V N M

A F S Q S N P P S E L H K V H G S R N K

P T S L W N P T Y G S W F T E K P T K K

N N P I A K K E P H D R G N L G L E G S

C T V P P N V A T G R L P G A S L L L E

P S S L T A N M K E V P L F R L R H F P

C G N V N Y G Y Q Q Q G L P L E A A T A

P G A G H Y E D T I L K S K N S M N Q P

G P * A R S H T H F S S L G S L R P W R

R E R Q W L L H K P E T K C H V L F C A

N L F * S T T K K A V F * K C F R K V L

S M G S S Y S F E R R K Y H K N E * * I

Q G P D V V A * G F Y A C L L Y T S L C

F F Q I V C A L L Q C S Q N * L L L C F

I V G V I D V S L P C * C G H E P F E G

R G N G N K G V I C N D *

An exemplary ALK polypeptide sequence is provided at UniProt Accession No. >sp|Q9UM73|ALK HUMAN ALK tyrosine kinase receptor OS=*Homo sapiens* OX=9606 GN=ALK PE=1 SV=3

```
                                        (SEQ ID NO: 8)
MGAIGLLWLLPLLLSTAAVGSGMGTGQRAGSPAAGPPLQPREPLSYSRL

QRKSLAVDEVVPSLFRVYARDLLLPPSSSELKAGRPEARGSLALDCAPL

LRLLGPAPGVSWTAGSPAPAEARTLSRVLKGGSVRKLRRAKQLVLELGE

EAILEGCVGPPGEAAVGLLQENLSELFSWWIRQGEGRLRIRLMPEKKAS

EVGREGRLSAAIRASQPRLLFQIFGTGHSSLESPTNMPSPSPDYFTWNL

TWIMKDSFPFLSHRSRYGLECSFDFPCELEYSPPLHDLRNQSWSWRRIP

SEEASQMDLLDGPGAERSKEMPRGSFLLLNTSADSKHTILSPWMRSSSE

HCTLAVSVHRHLQPSGRYIAQLLPHNEAAREILLMPTPGKHGWTVLQGR

IGRPDNPFRVALEYISSGNRSLSAVDFEALKNCSEGTSPGSKMALQSSF

TCWNGTVLQLGQACDFHQDCAQGEDESQMCRKLPVGFYCNFEDGFCGWT

QGTLSPHTPQWQVRTLKDARFQDHQDHALLLSTTDVPASESATVTSATF

PAPIKSSPCELRMSWLIRGVLRGNVSLVLVENKTGKEQGRMVWHVAAYE

GLSLWQWMVLPLLDVSDRFWLQMVAWWGQGSRAIVAFDNISISLDCYLT

ISGEDKILQNTAPKSRNLFERNPNKELKPGENSPRQTPIFDPTVHWLFT

TCGASGPHGPTQAQCNNAYQNSNLSVEVGSEGPLKGIQIWKVPATDTYS

ISGYGAAGGKGGKNTMMRSHGVSVLGIFNLEKDDMLYILVGQQGEDACP

STNQLIQKVCIGENNVIEEEIRVNRSVHEWAGGGGGGGGATYVFKMKDG

VPVPLIIAAGGGGRAYGAKTDTFHPERLENNSSVLGLNGNSGAAGGGGG

WNDNTSLLWAGKSLQEGATGGHSCPQAMKKWGWETRGGFGGGGGGCSSG

GGGGGYIGGNAASNNDPEMDGEDGVSFISPLGILYTPALKVMEGHGEVN
```

-continued

```
IKHYLNCSHCEVDECHMDPESHKVICFCDHGTVLAEDGVSCIVSPTPEP

HLPLSLILSVVTSALVAALVLAFSGIMIVYRRKHQELQAMQMELQSPEY

KLSKLRTSTIMTDYNPNYCFAGKTSSISDLKEVPRKNITLIRGLGHGAF

GEVYEGQVSGMPNDPSPLQVAVKTLPEVCSEQDELDFLMEALIISKFNH

QNIVRCIGVSLQSLPRFILLELMAGGDLKSFLRETRPRPSQPSSLAMLD

LLHVARDIACGCQYLEENHFIHRDIAARNCLLTCPGPGRVAKIGDFGMA

RDIYRASYYRKGGCAMLPVKWMPPEAFMEGIFTSKTDTWSFGVLLWEIF

SLGYMPYPSKSNQEVLEFVTSGGRMDPPKNCPGPVYRIMTQCWQHQPED

RPNFAIILERIEYCTQDPDVINTALPIEYGPLVEEEEKVPVRPKDPEGV

PPLLVSQQAKREEERSPAAPPPLPTTSSGKAAKKPTAAEISVRVPRGPA

VEGGHVNMAFSQSNPPSELHKVHGSRNKPTSLWNPTYGSWFTEKPTKKN

NPIAKKEPHDRGNLGLEGSCTVPPNVATGRLPGASLLLEPSSLTANMKE

VPLFRLRHFPCGNVNYGYQQQGLPLEAATAPGAGHYEDTILKSKNSMNQ

PGP
```

Exemplary ALK peptide amino acid sequences are provided in Table 3, Table 4, and Table 5.

An exemplary ALK peptide amino sequence is as follows: RPRPSQPSSL (SEQ ID NO: 2).

An exemplary ALK peptide amino sequence is as follows: IVRCIGVSL (SEQ ID NO: 3).

An exemplary ALK peptide amino sequence is as follows: VPRKNITLI (SEQ ID NO: 4).

An exemplary ALK peptide amino sequence is as follows: TAAEVSVRV (SEQ ID NO: 5).

An exemplary ALK peptide amino sequence is as follows: AMLDLLHVA (SEQ ID NO: 1).

By "ALK polynucleotide" is meant any nucleic acid molecule encoding an ALK polypeptide or fragment thereof (antigen or antigen protein). An exemplary full-length ALK nucleic acid sequence from *Homo Sapiens* is provided below:

```
                                                          (SEQ ID NO: 9)
  2 ggggcggcagcggtggtagcagctggtacctcccgccgcctctgttcggagggtcgcggg   61

 62 gcaccgaggtgctttccggccgccctctggtcggccacccaaagccgcgggcgctgatga   121

122 tgggtgaggagggggcggcaagatttcgggcgcccctgccctgaacgccctcagctgctg   181

182 ccgccggggccgctccagtgcctgcgaactctgaggagccgaggcgccggtgagagcaag   241

242 gacgctgcaaacttgcgcagcgcgggggctgggattcacgcccagaagttcagcaggcag   301

302 acagtccgaagccttcccgcagcggagagatagcttgagggtgcgcaagacggcagcctc   361

362 cgccctcggttcccgcccagaccgggcagaagagcttggaggagccaaaaggaacgcaaa   421

422 aggcggccaggacagcgtgcagcagctgggagccgccgttctcagccttaaaagttgcag   481

482 agattggaggctgccccgagaggggacagaccccagctccgactgcgggggcaggagag   541

542 gacggtacccaactgccacctcccttcaaccatagtagttcctctgtaccgagcgcagcg   601

602 agctacagacgggggcgcggcactcggcgcggagagcgggaggctcaaggtcccagccag   661

662 tgagcccagtgtgcttgagtgtctctggactcgcccctgagcttccaggtctgtttcatt   721

722 tagactcctgctcgcctccgtgcagttgggggaaagcaagagacttgcgcgcacgcacag   781

782 tcctctggagatcaggtggaaggagccgctgggtaccaaggactgttcagagcctcttcc   841

842 catctcggggagagcgaagggtgaggctgggcccggagagcagtgtaaacggcctcctcc   901
```

-continued

```
 902 ggcgggatgggagccatcgggctcctgtggctcctgccgctgctgctttccacggcagct   961
 962 gtgggctccgggatggggaccggccagcgcgcgggctccccagctgcggggccgccgctg  1021
1022 cagccccgggagccactcagctactcgcgcctgcagaggaagagtctggcagttgacttc  1081
1082 gtggtgccctcgctcttccgtgtctacgcccgggacctactgctgccaccatcctcctcg  1141
1142 gagctgaaggctggcaggcccgaggcccgcggctcgctagctctggactgcgccccgctg  1201
1202 ctcaggttgctggggccggcgccgggggtctcctggaccgccggttcaccagccccggca  1261
1262 gaggcccggacgctgtccagggtgctgaagggcggctccgtgcgcaagctccggcgtgcc  1321
1322 aagcagttggtgctggagctgggcgaggaggcgatcttggagggttgcgtcgggcccccc  1381
1382 ggggaggcggctgtggggctgctccagttcaatctcagcgagctgttcagttggtggatt  1441
1442 cgccaaggcgaagggcgactgaggatccgcctgatgcccgagaagaaggcgtcggaagtg  1501
1502 ggcagagagggaaggctgtccgcggcaattcgcgcctcccagccccgccttctcttccag  1561
1562 atcttcgggactggtcatagctccttggaatcaccaacaaacatgccttctccttctcct  1621
1622 gattattttacatggaatctcacctggataatgaaagactccttccctttcctgtctcat  1681
1682 cgcagccgatatggtctggagtgcagctttgacttcccctgtgagctggagtattcccct  1741
1742 ccactgcatgacctcaggaaccagagctggtcctggcgccgcatcccctccgaggaggcc  1801
1802 tcccagatggacttgctggatgggcctggggcagagcgttctaaggagatgcccagaggc  1861
1862 tcctttctccttctcaacacctcagctgactccaagcacaccatcctgagtccgtggatg  1921
1922 aggagcagcagtgagcactgcacactggccgtctcggtgcacaggcacctgcagccctct  1981
1982 ggaaggtacattgcccagctgctgccccacaacgaggctgcaagagagatcctcctgatg  2041
2042 cccactccagggaagcatggttggacagtgctccagggaagaatcgggcgtccagacaac  2101
2102 ccatttcgagtggccctggaatacatctccagtggaaaccgcagcttgtctgcagtggac  2161
2162 ttctttgccctgaagaactgcagtgaaggaacatccccaggctccaagatggccctgcag  2221
2222 agctccttcacttgttggaatgggacagtcctccagcttgggcaggcctgtgacttccac  2281
2282 caggactgtgcccagggagaagatgagagccagatgtgccggaaactgcctgtgggtttt  2341
2342 tactgcaactttgaagatggcttctgtggctggacccaaggcacactgtcaccccacact  2401
2402 cctcaatggcaggtcaggaccctaaaggatgcccggttccaggaccaccaagaccatgct  2461
2462 ctattgctcagtaccactgatgtccccgcttctgaaagtgctacagtgaccagtgctacg  2521
2522 tttcctgcaccgatcaagagctctccatgtgagctccgaatgtcctggctcattcgtgga  2581
2582 gtcttgaggggaaacgtgtccttggtgctagtggagaacaaaaccgggaaggagcaaggc  2641
2642 aggatggtctggcatgtcgccgcctatgaaggcttgagcctgtggcagtggatggtgttg  2701
2702 cctctcctcgatgtgtctgacaggttctggctgcagatggtcgcatggtggggacaagga  2761
2762 tccagagccatcgtggcttttgacaatatctccatcagcctggactgctacctcaccatt  2821
2822 agcggagaggacaagatcctgcagaatacagcacccaaatcaagaaacctgtttgagaga  2881
2882 aacccaaacaaggagctgaaacccggggaaaattcaccaagacagacccccatctttgac  2941
2942 cctacagttcattggctgttcaccacatgtggggccagcgggccccatggccccacccag  3001
3002 gcacagtgcaacaacgcctaccagaactccaacctgagcgtggaggtggggagcgagggc  3061
3062 cccctgaaaggcatccagatctggaaggtgccagccaccgacacctacagcatctcgggc  3121
3122 tacggagctgctggcgggaaaggcgggaagaacaccatgatgcggtcccacggcgtgtct  3181
3182 gtgctgggcatcttcaacctggagaaggatgacatgctgtacatcctggttgggcagcag  3241
3242 ggagaggacgcctgccccagtacaaaccagttaatccagaaagtctgcattggagagaac  3301
```

-continued 3302 aatgtgatagaagaagaaatccgtgtgaacagaagcgtgcatgagtgggcaggaggcgga 3361

3362 ggaggagggggtggagccacctacgtatttaagatgaaggatggagtgccggtgcccctg 3421

3422 atcattgcagccggaggtggtggcagggcctacggggccaagacagacacgttccaccca 3481

3482 gagagactggagaataactcctcggttctagggctaaacggcaattccggagccgcaggt 3541

3542 ggtggaggtggctggaatgataacacttccttgctctgggccggaaaatctttgcaggag 3601

3602 ggtgccaccggaggacattcctgcccccaggccatgaagaagtgggggtgggagacaaga 3661

3662 gggggtttcggagggggtggagggggggtgctcctcaggtggaggaggcggaggatatata 3721

3722 ggcggcaatgcagcctcaaacaatgaccccgaaatggatggggaagatggggtttccttc 3781

3782 atcagtccactgggcatcctgtacaccccagctttaaaagtgatggaaggccacggggaa 3841

3842 gtgaatattaagcattatctaaactgcagtcactgtgaggtagacgaatgtcacatggac 3901

3902 cctgaaagccacaaggtcatctgcttctgtgaccacgggacggtgctggctgaggatggc 3961

3962 gtctcctgcattgtgtcacccaccccggagccacacctgccactctcgctgatcctctct 4021

4022 gtggtgacctctgccctcgtggccgccctggtcctggctttctccggcatcatgattgtg 4081

4082 taccgccggaagcaccaggagctgcaagccatgcagatggagctgcagagccctgagtac 4141

4142 aagctgagcaagctccgcacctcgaccatcatgaccgactacaaccccaactactgcttt 4201

4202 gctggcaagacctcctccatcagtgacctgaaggaggtgccgcggaaaaacatcaccctc 4261

4262 attcggggtctgggccatggcgcctttggggaggtgtatgaaggccaggtgtccggaatg 4321

4322 cccaacgacccaagcccccctgcaagtggctgtgaagacgctgcctgaagtgtgctctgaa 4381

4382 caggacgaactggatttcctcatggaagccctgatcatcagcaaattcaaccaccagaac 4441

4442 attgttcgctgcattggggtgagcctgcaatccctgccccggttcatcctgctggagctc 4501

4502 atggcggggggagacctcaagtccttcctccgagagacccgccctcgcccgagccagccc 4561

4562 tcctccctggccatgctggaccttctgcacgtggctcgggacattgcctgtggctgtcag 4621

4622 tatttggaggaaaaccacttcatccaccgagacattgctgccagaaactgcctcttgacc 4681

4682 tgtccaggccctggaagagtggccaagattggagacttcgggatggcccgagacatctac 4742 agggcgagctactatagaaagggaggctgtgccatgctgccagttaagtggatgccccca 4801

4802 gaggccttcatggaaggaatattcacttctaaaacagacacatggtcctttggagtgctg 4861

4862 ctatgggaaatctttttctcttggatatatgccataccccagcaaaagcaaccaggaagtt 4921

4922 ctggagtttgtcaccagtggaggccggatggacccacccaagaactgccctgggcctgta 4981

4982 taccggataatgactcagtgctggcaacatcagcctgaagacaggcccaactttgccatc 5041

5042 attttggagaggattgaatactgcacccaggacccggatgtaatcaacaccgctttgccg 5101

5102 atagaatatggtccacttgtggaagaggaagagaaagtgcctgtgaggcccaaggaccct 5161

5162 gagggggttcctcctctcctggtctctcaacaggcaaaacgggaggaggagcgcagccca 5221

5222 gctgccccaccacctctgcctaccacctcctctggcaaggctgcaaagaaacccacagct 5281

5282 gcagagatctctgttcgagtccctagagggccggccgtggaaggggggacacgtgaatatg 5341

5342 gcattctctcagtccaaccctccttcggagttgcacaaggtccacggatccagaaacaag 5401

5402 cccaccagcttgtggaacccaacgtacggctcctggtttacagagaaacccaccaaaaag 5461

5462 aataatcctatagcaaagaaggagccacacgacaggggtaacctggggctggagggaagc 5521

5522 tgtactgtcccacctaacgttgcaactgggagacttccgggggcctcactgctcctagag 5581

5582 ccctcttcgctgactgccaatatgaaggaggtacctctgttcaggctacgtcacttccct 5641

5642 tgtgggaatgtcaattacggctaccagcaacagggcttgcccttagaagccgctactgcc 5701

5702 cctggagctggtcattacgaggataccattctgaaaagcaagaatagcatgaaccagcct 5761

-continued

```
5762 gggccctgagctcggtcgcacactcacttctcttccttgggatccctaagaccgtggagg 5821

5822 agagagaggcaatggctccttcacaaaccagagaccaaatgtcacgttttgttttgtgcc 5881

5882 aacctattttgaagtaccaccaaaaaagctgtattttgaaaatgctttagaaaggttttg 5941

5942 agcatgggttcatcctattctttcgaaagaagaaaatatcataaaaatgagtgataaata 6001

6002 caaggcccagatgtggttgcataaggtttttatgcatgtttgttgtatacttccttatgc 6061

6062 ttctttcaaattgtgtgtgctctgcttcaatgtagtcagaattagctgcttctatgtttc 6121

6122 atagttggggtcatagatgtttccttgccttgttgatgtggacatgagccatttgagggg 6181

6182 agagggaacggaaataaaggagttatttgtaatgactaaaa                    6222
```

By "alteration" is meant a change (increase or decrease) in the expression levels or activity of a gene or polypeptide as detected by standard art known methods such as those described herein. As used herein, an alteration includes a 5% change in expression levels, a 10% change in expression levels, preferably a 25% change, more preferably a 40% change, and most preferably a 50% or greater change in expression levels.

By "ameliorate" is meant decrease, reduce, delay diminish, suppress, attenuate, arrest, or stabilize the development or progression of a disease or pathological condition.

By "antibody" is meant an immunoglobulin (Ig) molecule produced by B lymphoid cells and having a specific amino acid sequence. Antibodies are evoked or elicited in subjects (humans or other animals or mammals) following exposure to a specific antigen (immunogen). A subject capable of generating antibodies/immunoglobulins (i.e., an immune response) directed against a specific antigen/immunogen is said to be immunocompetent. Antibodies are characterized by reacting specifically with (e.g., binding to) an antigen or immunogen in some demonstrable way, antibody and antigen/immunogen each being defined in terms of the other. "Eliciting an antibody response" refers to the ability of an antigen, immunogen or other molecule to induce the production of antibodies. Antibodies are of different classes, e.g., IgM, IgG, IgA, IgE, IgD and subtypes or subclasses, e.g., IgG1, IgG2, IgG2a, IgG2b, IgG3, IgG4. An antibody/immunoglobulin response elicited in a subject can neutralize a pathogenic (e.g., disease-causing) agent by binding to epitopes (antigenic determinants) on the agent and blocking or inhibiting the activity of the agent, and/or by forming a binding complex with the agent that is cleared from the system of the subject, e.g., via the liver.

By "amphiphile" is meant a chemical compound possessing both hydrophilic and lipophilic properties. Such a compound is called amphiphilic or amphipathic. The amphiphile may be conjugated or linked to an antigen or adjuvant cargo by a solubility-promoting polar polymer chain. In some embodiments, the amphiphile is conjugated or linked to an adjuvant. In some embodiments, the adjuvant is Freund's adjuvant. In some embodiments, the amphiphile is conjugated or linked to an ALK antigen or immunogen. In some embodiments, the amphiphile is a lipophilic albumin-binding tail. In some embodiments, the amphiphile is N-hydroxy succinimidyl ester-end-functionalized poly(ethylene glycol)-lipid (NHS-PEG2KDa-DSPE).

By "antigen" is meant an agent (e.g., polypeptide, peptide) that can stimulate an immune response in an animal, including compositions that are injected or absorbed into an animal. An antigen reacts with the products of specific humoral or cellular immunity, including those induced by heterologous immunogens. In some embodiments of the disclosed compositions and methods, the antigen is an ALK protein or an antibody-binding portion thereof. An antigen that elicits or stimulates an immune response in a subject is termed an "immunogen." A "codon-optimized" nucleic acid (polynucleotide) refers to a nucleic acid sequence that has been altered such that the codons are optimal for expression in a particular system (such as a particular species of group of species). For example, a nucleic acid sequence can be optimized for expression in mammalian cells. Codon optimization does not alter the amino acid sequence of the encoded protein.

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

"Detect" refers to identifying the presence, absence or amount of an analyte, compound, agent, or substance to be detected.

By "detectable label" is meant a composition that, when linked to a molecule of interest, renders the latter detectable, e.g., via spectroscopic, photochemical, biochemical, immunochemical, or chemical means. Nonlimiting examples of useful detectable labels include radioactive isotopes, magnetic beads, metallic beads, colloidal particles, fluorescent dyes, electron-dense reagents, enzymes (for example, as commonly used in an ELISA), biotin, digoxigenin, or haptens.

By "disease" is meant any condition, disorder, or pathology that damages or interferes with the normal function of a cell, tissue, or organ. Examples of diseases include those caused by oncogenic ALK gene fusions, rearrangements, duplications or mutations (e.g., ALK-positive cancers). In some embodiments, the cancer is an ALK-positive cancer. By "ALK-positive cancer" is meant a cancer or tumor that expresses the ALK protein. Nonlimiting examples of ALK-positive cancers include non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, and melanoma. The ALK-positive cancer may be caused by an oncogenic ALK gene that either forms a fusion gene with other genes, gains additional gene copies, or is genetically mutated. In some embodiments, the ALK-positive cancer is caused by an ALK fusion gene encoding an ALK fusion protein. In some embodiments, the ALK-positive cancer is caused by a fusion between the ALK gene and the nucleophosmin (NPM) gene encoding a NPM-ALK fusion protein. In some embodiments, the ALK-positive cancer is caused by a fusion between the ALK gene and the echinoderm microtubule-associated protein-like 4 (EML4) gene encoding an ELM4-ALK fusion protein.

By "effective amount" is meant the amount of an active therapeutic agent, composition, compound, biologic (e.g., a vaccine or therapeutic peptide, polypeptide, or polynucleotide) required to ameliorate, reduce, delay, improve, abrogate, diminish, or eliminate the symptoms and/or effects of a disease, condition, or pathology relative to an untreated patient. In some embodiments, an effective amount of an ALK peptide is the amount required to induce an ALK-specific immune response in a subject immunized with the peptide. The effective amount of an immunogen or a composition comprising an immunogen, as used to practice the methods of therapeutic treatment of a disease, condition, or pathology, varies depending upon the manner of administration, the age, body weight, and general health of the subject. Ultimately, the attending physician or veterinarian will decide the appropriate amount and dosage regimen. Such amount is referred to as an "effective" amount.

The inventions herein provide a number of targets that are useful for the development of highly specific drugs to treat a disease or disorder characterized by the methods delineated herein. In addition, the methods of the invention provide a facile means to identify therapies that are safe for use in subjects. In addition, the methods of the invention provide a route for analyzing virtually any number of compounds for effects on a disease described herein with high-volume throughput, high sensitivity, and low complexity.

A "therapeutically effective amount" refers to a quantity of a specified agent sufficient to achieve a desired effect in a subject being treated with that agent. For example, this may be the amount of an ALK-specific antigen, immunogen, immunogenic composition or vaccine useful for eliciting an immune response in a subject, treating and/or for preventing a disease caused by oncogenic ALK gene fusions, rearrangements, duplications or mutations (e.g., ALK-positive cancers). Ideally, in the context of the present disclosure, a therapeutically effective amount of an ALK-specific vaccine or immunogenic composition is an amount sufficient to prevent, ameliorate, reduce, delay and/or treat a disease caused by oncogenic ALK gene fusions, rearrangements, duplications or mutations (e.g., ALK-positive cancers) in a subject without causing a substantial cytotoxic effect in the subject. The effective amount of an ALK-specific vaccine or immunogenic composition useful for preventing, delaying, ameliorating, reducing, and/or treating a disease caused by oncogenic ALK gene fusions, rearrangements, duplications or mutations (e.g., ALK-positive cancers) in a subject depends on, for example, the subject being treated, the manner of administration of the therapeutic composition and other factors, as noted supra.

By "fragment" is meant a portion of a polypeptide or nucleic acid molecule. This portion contains, preferably, at least 10%, 20%, 30%, 40%, 50%, 60%, 70%, 80%, or 90% of the entire length of the reference nucleic acid molecule or polypeptide. A fragment may contain 3, 4, 5, 6, 7, 8, 9, 10, 20, 30, 40, 50, 60, 70, 80, 90, or 100, 200, 300, 400, 500, 600, 700, 800, 900, or 1000 nucleotides or amino acids. A portion or fragment of a polypeptide may be a peptide. In the case of an antibody or immunoglobulin fragment, the fragment typically binds to the target antigen.

By "fusion protein" is meant a protein generated by expression of a nucleic acid (polynucleotide) sequence engineered from nucleic acid sequences encoding at least a portion of two different (heterologous) proteins or peptides. To create a fusion protein, the nucleic acid sequences must be in the same open reading frame and contain no internal stop codons. One protein can be located at the amino-terminal (N-terminal) portion of the fusion protein or at the carboxy-terminal (C-terminal) protein thus forming an amino-terminal fusion protein or a carboxy-terminal fusion protein, respectively.

For example, a fusion protein includes an ALK protein fused to a heterologous protein. In some embodiments, the fusion protein is an ALK protein fused to a nucleophosmin (NPM) protein. In some embodiments, the NPM-ALK fusion protein is at least 85%, at least 90%, at least 95%, at least 98%, at least 99%, or 100% identical to a NPM-ALK fusion protein in *Homo Sapiens*. In some embodiments, the NPM-ALK fusion protein is at least 85%, at least 90%, at least 95%, at least 98%, at least 99%, or 100% identical to an exemplary NPM-ALK fusion protein amino acid sequence from *Homo Sapiens* as provided below (ALK cytoplasmic portion in bold font):

(SEQ ID NO: 10)

MEDSMDMDMSPLRPQNYLFGCELKADKDYHFKVDNDENEHQLSLRTVSLG

AGAKDELHIVEAEAMNYEGSPIKVTLATLKMSVQPTVSLGGFEITPPVVL

RLKCGSGPVHISGQHLVVYRRKHQELQAMQMELQSPEYKLSKLRTSTIMT

DYNPNYCFAGKTSSISDLKEVPRKNNTLIRGLGHGAFGEVYEGQVSGMPN

DPSPLQVAVKTLPEVCSEQDELDFLMEALIISKFNHQNIVRCIGVSLQSL

PRFILLELMAGGDLKSFLRETRPRPSQPSSLAMLDLLHVARDIACGCQYL

EENHFIHRDIAARNCLLTCPGPGRVAKIGDFGMARDIYRASYYRKGGCAM

LPVKWMPPEAFMEGIFTSKTDTWSFGVLLWEIFSLGYMPYPSKSNQEVLE

FVTSGGRMDPPKNCPGPVYRIMTQCWQHQPEDRPNFAIILERIEYCTQDP

DVINTALPIEYGPLVEEEEKVPVRPKDPEGVPPLLVSQQAKREEERSPAA

PPPLPTTSSGKAAKKPTAAEVSVRVPRGPAVEGGHVNMAFSQSNPPSELH

RVHGSRNKPTSLWNPTYGSWFTEKPTKKNNPIAKKEPHERGNLGLEGSCT

VPPNVATGRLPGASLLLEPSSLTANMKEVPLFRLRHFPCGNVNYGYQOQG

LPLEAATAPGAGHYEDTILKSKNSMNQPGP

In some embodiments, the NPM-ALK fusion protein is at least 85%, at least 90%, at least 95%, at least 98%, at least 99%, or 100% identical to an exemplary NPM-ALK fusion protein amino acid sequence from *Homo Sapiens* (GenBank: AAA58698.1) as provided below:

(SEQ ID NO: 11)

1 medsmdmdms plrpqnylfg celkadkdyh fkvdndeneh qlslrtvslg agakdelhiv 61 eaeamnyegs pikvtlatlk msvqptvslg gfeitppvvl rlkcgsgpvh isgqhlvvyr -continued

```
121 rkhqelqamq melqspeykl skirtstimt dynpnycfag ktssisdlke vprknitlir

181 glghgafgev yegqvsgmpn dpsplqvavk tlpevcseqd eldfimeali iskfnhqniv

241 rcigvslqsl prfillelma ggdlksfire trprpsqpss lamldllhva rdiacgcqyl

301 eenhfihrdi aarnclltcp gpgrvakigd fgmardiyra syyrkggcam lpvkwmppea

361 fmegiftskt dtwsfgvllw eifsigympy psksnqevle fvtsggrmdp pkncpgpvyr

421 imtqcwqhqp edrpnfaiil erieyctqdp dvintalpie ygplveeeek vpvrpkdpeg

481 vppllvsqqa kreeerspaa ppplpttssg kaakkptaae vsvrvprgpa vegghvnmaf

541 sqsnppselh kvhgsrnkpt slwnptygsw ftekptkknn piakkephdr gniglegsct

601 vppnvatgrl pgaslllleps sltanmkevp ifrlrhfpcg nvnygyqqqg ipleaatapg

661 aghyedtilk sknsmnqpgp
```

In some embodiments, the NPM-ALK fusion protein is at least 85%, at least 90%, at least 95%, at least 98%, at least 99%, or 100% identical to an exemplary NPM-ALK fusion protein amino acid sequence from *Homo Sapiens* as provided below:

```
                                    (SEQ ID NO: 11)
M E D S M D M D M S P L R P Q N Y L F G

C E L K A D K D Y H F K V D N D E N E H

Q L S L R T V S L G A G A K D E L H I V

E A E A M N Y E G S P I K V T L A T L K

M S V Q P T V S L G G F E I T P P V V L

R L K C G S G P V H I S G Q H L V V Y R

R K H Q E L Q A M Q M E L Q S P E Y K L

S K L R T S T I M T D Y N P N Y C F A G

K T S S I S D L K E V P R K N I T L I R

G L G H G A F G E V Y E G Q V S G M P N

D P S P L Q V A V K T L P E V C S E Q D

E L D F L M E A L I I S K F N H Q N I V

R C I G V S L Q S L P R F I L L E L M A

G G D L K S F L R E T R P R P S Q P S S

L A M L D L L H V A R D I A C G C Q Y L

E E N H F I H R D I A A R N C L L T C P

G P G R V A K I G D F G M A R D I Y R A
```

-continued

```
S Y Y R K G G C A M L P V K W M P P E A

F M E G I F T S K T D T W S F G V L L W

E I F S L G Y M P Y P S K S N Q E V L E

F V T S G G R M D P P K N C P G P V Y R

I M T Q C W Q H Q P E D R P N F A I I L

E R I E Y C T Q D P D V I N T A L P I E

Y G P L V E E E E K V P V R P K D P E G

V P P L L V S Q Q A K R E E E R S P A A

P P P L P T T S S G K A A K K P T A A E

V S V R V P R G P A V E G G H V N M A F

S Q S N P P S E L H K V H G S R N K P T

S L W N P T Y G S W F T E K P T K K N N

P I A K K E P H D R G N L G L E G S C T

V P P N V A T G R L P G A S L L L E P S

S L T A N M K E V P L F R L R H F P C G

N V N Y G Y Q Q Q G L P L E A A T A P G

A G H Y E D T I L K S K N S M N Q P G P

*
```

In some embodiments, the NPM-ALK fusion protein is encoded by a nucleic acid sequence that is at least 85%, at least 90%, at least 95%, at least 98%, at least 99%, or 100% identical to the exemplary nucleic acid sequence from *Homo Sapiens* as provided below:

```
                                                        (SEQ ID NO: 12)
  1 atggaagattcgatggacatggacatgagcccccctgaggccccagaactatcttttcggt   60

 61 tgtgaactaaaggccgacaaagattatcactttaaggtggataatgatgaaaatgagcac  120

121 cagttatctttaagaacggtcagtttaggggctggtgcaaaggatgagttgcacattgtt  180

181 gaagcagaggcaatgaattacgaaggcagtccaattaaagtaacactggcaactttgaaa  240

241 atgtctgtacagccaacggtttcccttgggggctttgaaataacaccaccagtggtctta  300

301 aggttgaagtgtggttcagggccagtgcatattagtggacagcacttagtagtgtaccgc  360

361 cggaagcaccaggagctgcaagccatgcagatggagctgcagagccctgagtacaagctg  420
```

-continued

```
421 agcaagctccgcacctcgaccatcatgaccgactacaaccccaactactgctttgctggc   480
481 aagacctcctccatcagtgacctgaaggaggtgccgcggaaaaacatcaccctcattcgg   540
541 ggtctgggccatggcgcctttggggaggtgtatgaaggccaggtgtccggaatgcccaac   600
601 gacccaagcccctgcaagtggctgtgaagacgctgcctgaagtgtgctctgaacaggac   660
661 gaactggatttcctcatggaagccctgatcatcagcaaattcaaccaccagaacattgtt   720
721 cgctgcattggggtgagcctgcaatccctgccccggttcatcctgctggagctcatggcg   780
781 gggggagacctcaagtccttcctccgagagacccgccctcgcccgagccagccctcctcc   840
841 ctggccatgctggaccttctgcacgtggctcgggacattgcctgtggctgtcagtatttg   900
901 gaggaaaaccacttcatccaccgagacattgctgccagaaactgcctcttgacctgtcca   960
961 ggccctggaagagtggccaagattggagacttcgggatggcccgagacatctacagggcg  1020
1021 agctactatagaaagggaggctgtgccatgctgccagttaagtggatgcccccagaggcc  1080
1081 ttcatggaaggaatattcacttctaaaacagacacatggtcctttggagtgctgctatgg  1140
1141 gaaatcttttctcttggatatatgccataccccagcaaaagcaaccaggaagttctggag  1200
1201 tttgtcaccagtggaggccggatggacccacccaagaactgccctgggcctgtataccgg  1260
1261 ataatgactcagtgctggcaacatcagcctgaagacaggcccaactttgccatcattttg  1320
1321 gagaggattgaatactgcacccaggacccggatgtaatcaacaccgctttgccgatagaa  1380
1381 tatggtccacttgtggaagaggaagagaaagtgcctgtgaggcccaaggaccctgagggg  1440
1441 gttcctcctctcctggtctctcaacaggcaaaacgggaggaggagcgcagcccagctgcc  1500
1501 ccaccacctctgcctaccacctcctctggcaaggctgcaaagaaacccacagctgcagag  1560
1561 gtctctgttcgagtccctagagggccggccgtggaagggggacacgtgaatatggcattc  1620
1621 tctcagtccaaccctccttcggagttgcacaaggtccacggatccagaaacaagcccacc  1680
1681 agcttgtggaacccaacgtacggctcctggtttacagagaaacccaccaaaaagaataat  1740
1741 cctatagcaaagaaggagccacacgacaggggtaacctggggctggagggaagctgtact  1800
1801 gtcccacctaacgttgcaactgggagacttccgggggcctcactgctcctagagccctct  1860
1861 tcgctgactgccaatatgaaggaggtacctctgttcaggctacgtcacttcccttgtggg  1920
1921 aatgtcaattacggctaccagcaacagggcttgcccttagaagccgctactgcccctgga  1980
1981 gctggtcattacgaggataccattctgaaaagcaagaatagcatgaaccagcctgggccc  2040
2041 tga                                                            2043
```

In some embodiments, the fusion protein is an ALK protein fused to an echinoderm microtubule-associated protein-like 4 (EML4) protein. In some embodiments, the ELM4-ALK fusion protein is at least 85%, at least 90%, at least 95%, at least 98%, at least 99%, or 100% identical to a ELM4-ALK fusion protein in *Homo Sapiens* or a variant thereof. In some embodiments, the ELM4-ALK fusion protein is at least 85%, at least 90%, at least 95%, at least 98%, at least 99%, or 100% identical to an exemplary ELM4-ALK fusion protein amino acid sequence from *Homo Sapiens* (GenBank: BAM37627.1) as provided below:

```
                                                        (SEQ ID NO: 13)
  1 mdgfagsldd sisaastsdv qdrlsalesr vqqqedeitv ikaaladvlr rlaisedhva
 61 svkksvsskg qpspravipm scitngsgan rkpshtsavs iagketlssa aksgtekkke
121 kpqgqrekke eshsndqspq iraspspqps sqplqihrqt pesknatptk sikrpspaek
181 shnswensdd srnklskips tpklipkvtk tadkhkdvii nqegeyikmf mrgrpitmfi
241 psdvdnyddi rtelppeklk lewaygyrgk dcranvyllp tgeivyfias vvvlfnyeer
301 tqrhylghtd cvkclaihpd kiriatgqia gvdkdgrplq phvrvwdsvt lstlqiiglg
```

-continued 361 tfergvgcld fskadsgvhl cviddsnehm ltvwdwqrka kgaeikttne vvlavefhpt 421 dantiitcgk shiffwtwsg nsltrkqgif gkyekpkfvq clafigngdv ltgdsggvml 481 iwskttvept pgkgpkgvyq iskqikahdg svftlcqmrn gmlltgggkd rkiilwdhdl 541 npereiefsa srarlpghva adhppavyrr khqelqamqm elqspeykls klrtstimtd 601 ynpnycfagk tssisdlkev prknitlirg lghgafgevy egqvsgmpnd psplqvavkt 661 lpevcseqde ldflmealii skfnhqnivr cigvslqslp rfillelmag gdlksflret 721 rprpsqpssl amldllhvar diacgcqyle enhfihrdia arnclltcpg pgrvakigdf 781 gmardiyras yyrkggcaml pvkwmppeaf megiftsktd twsfgvllwe ifslgympyp 841 sksnqevlef vtsggrmdpp kncpgpvyri mtqcwqhqpe drpnfaiile rieyctqdpd 901 vintalpiey gplveeeekv pvrpkdpegv ppllvsqqak reeerspaap pplpttssgk 961 aakkptaaei svrvprgpav egghvnmafs qsnppselhk vhgsrnkpts lwnptygswf 1021 tekptkknnp iakkephdrg nlglegsctv ppnvatgrlp gaslllepss ltanmkevpl 1081 frlrhfpcgn vnygyqqqgl pleaatapga ghyedtilks knsmnqpgp In some embodiments, the ELM4-ALK fusion protein is encoded by a nucleic acid sequence that is at least 85%, at least 90%, at least 95%, at least 98%, at least 99%, or 100% identical to an exemplary nucleic acid sequence from *Homo Sapiens* (GenBank: AB274722.1) as provided below:

(SEQ ID NO: 14)

1 ggcggcgcgg cgcggcgctc gcggctgctg cctgggaggg aggccgggca ggcggctgag 61 cggcgcggct ctcaacgtga cggggaagtg gttcgggcgg ccgcggctta ctaccccagg 121 gcgaacggac ggacgacgga ggcgggagcc ggtagccgag ccgggcgacc tagagaacga 181 gcgggtcagg ctcagcgtcg gccactctgt cggtccgctg aatgaagtgc ccgcccctct 241 gagcccggag cccggcgctt tccccgcaag atggacggtt tcgccggcag tctcgatgat 301 agtatttctg ctgcaagtac ttctgatgtt caagatcgcc tgtcagctct tgagtcacga 361 gttcagcaac aagaagatga aatcactgtg ctaaaggcgg ctttggctga tgttttgagg 421 cgtcttgcaa tctctgaaga tcatgtggcc tcagtgaaaa aatcagtctc aagtaaaggc 481 caaccaagcc ctcgagcagt tattcccatg tcctgtataa ccaatggaag tggtgcaaac 541 agaaaaccaa gtcataccag tgctgtctca attgcaggaa aagaaactct ttcatctgct 601 gctaaaagtg gtacagaaaa aaagaaagaa aaaccacaag gacagagaga aaaaaaagag 661 gaatctcatt ctaatgatca aagtccacaa attcgagcat caccttctcc ccagccctct 721 tcacaacctc tccaaataca cagacaaact ccagaaagca agaatgctac tcccaccaaa 781 agcataaaac gaccatcacc agctgaaaag tcacataatt cttgggaaaa ttcagatgat 841 agccgtaata aattgtcgaa aataccttca acacccaaat taataccaaa agttaccaaa 901 actgcagaca agcataaaga tgtcatcatc aaccaagaag gagaatatat taaaatgttt 961 atgcgcggtc ggccaattac catgttcatt ccttccgatg ttgacaacta tgatgacatc 1021 agaacggaac tgcctcctga gaagctcaaa ctggagtggg catatggtta tcgaggaaag 1081 gactgtagag ctaatgttta ccttcttccg accggggaaa tagtttattt cattgcatca 1141 gtagtagtac tatttaatta tgaggagaga actcagcgac actacctggg ccatacagac 1201 tgtgtgaaat gccttgctat acatcctgac aaaattagga ttgcaactgg acagatagct 1261 ggcgtggata aagatggaag gcctctacaa ccccacgtca gagtgtggga ttctgttact 1321 ctatccacac tgcagattat tggacttggc acttttgagc gtggagtagg atgcctggat -continued

```
1381 ttttcaaaag cagattcagg tgttcattta tgtgttattg atgactccaa tgagcatatg
1441 cttactgtat gggactggca gaagaaagca aaaggagcag aaataaagac aacaaatgaa
1501 gttgttttgg ctgtggagtt tcacccaaca gatgcaaata ccataattac atgcggtaaa
1561 tctcatattt tcttctggac ctggagcggc aattcactaa caagaaaaca gggaattttt
1621 gggaaatatg aaaagccaaa atttgtgcag tgtttagcat tcttggggaa tggagatgtt
1681 cttactggag actcaggtgg agtcatgctt atatggagca aaactactgt agagcccaca
1741 cctgggaaag gacctaaagt gtaccgccgg aagcaccagg agctgcaagc catgcagatg
1801 gagctgcaga gccctgagta caagctgagc aagctccgca cctcgaccat catgaccgac
1861 tacaacccca actactgctt tgctggcaag acctcctcca tcagtgacct gaaggaggtg
1921 ccgcggaaaa acatcaccct cattcggggt ctgggccatg gagcctttgg ggaggtgtat
1981 gaaggccagg tgtccggaat gcccaacgac ccaagccccc tgcaagtggc tgtgaagacg
2041 ctgcctgaag tgtgctctga acaggacgaa ctggatttcc tcatggaagc cctgatcatc
2101 agcaaattca accaccagaa cattgttcgc tgcattgggg tgagcctgca atccctgccc
2161 cggttcatcc tgctggagct catggcgggg ggagacctca agtccttcct ccgagagacc
2221 cgccctcgcc cgagccagcc ctcctccctg gccatgctgg accttctgca cgtggctcgg
2281 gacattgcct gtggctgtca gtatttggag gaaaaccact tcatccaccg agacattgct
2341 gccagaaact gcctcttgac ctgtccaggc cctggaagag tggccaagat tggagacttc
2401 gggatggccc gagacatcta cagggcgagc tactatagaa agggaggctg tgccatgctg
2461 ccagttaagt ggatgccccc agaggccttc atggaaggaa tattcacttc taaaacagac
2521 acatggtcct ttggagtgct gctatgggaa atcttttctc ttggatatat gccatacccc
2581 agcaaaagca accaggaagt tctggagttt gtcaccagtg gaggccggat ggacccaccc
2641 aagaactgcc ctgggcctgt ataccggata atgactcagt gctggcaaca tcagcctgaa
2701 gacaggccca actttgccat cattttggag aggattgaat actgcaccca ggacccggat
2761 gtaatcaaca ccgctttgcc gatagaatat ggtccacttg tggaagagga agagaaagtg
2821 cctgtgaggc ccaaggaccc tgaggggggtt cctcctctcc tggtctctca acaggcaaaa
2881 cgggaggagg agcgcagccc agctgcccca ccacctctgc ctaccacctc ctctggcaag
2941 gctgcaaaga aacccacagc tgcagaggtc tctgttcgag tccctagagg gccggccgtg
3001 gaagggggac acgtgaatat ggcattctct cagtccaacc ctccttcgga gttgcacagg
3061 gtccacggat ccagaaacaa gcccaccagc ttgtggaacc caacgtacgg ctcctggttt
3121 acagagaaac ccaccaaaaa gaataatcct atagcaaaga aggagccaca cgagaggggt
3181 aacctggggc tggagggaag ctgtactgtc ccacctaacg ttgcaactgg gagacttccg
3241 ggggcctcac tgctcctaga gccctcttcg ctgactgcca atatgaagga ggtacctctg
3301 ttcaggctac gtcacttccc ttgtgggaat gtcaattacg gctaccagca acagggcttg
3361 cccttagaag ccgctactgc ccctggagct ggtcattacg aggataccat tctgaaaagc
3421 aagaatagca tgaaccagcc tgggccctga gctcggtcac acactcactt ctcttccttg
3481 ggatccctaa gaccgtggag gagagagagg caatcaatgg ctccttcaca aaccagagac
3541 caaatgtcac gttttgtttt gtgccaacct attttgaagt accaccaaaa aagctgtatt
3601 ttgaaaatgc tttagaaagg ttttgagcat gggttcatcc tattctttcg aaagaagaaa
3661 atatcataaa aatgagtgat aaatacaagg cccagatgtg gttgcataag gtttttatgc
3721 atgtttgttg tatacttcct tatgcttctt ttaaattgtg tgtgctctgc ttcaatgtag
```

-continued

```
3781 tcagaattag ctgcttctat gtttcatagt tggggtcata gatgtttcct tgccttgttg

3841 atgtggacat gagccatttg aggggagagg gaacggaaat aaaggagtta tttgtaatga

3901 aaaaaaaaaa aaaaaaaaaa aaaaaa
```

In some embodiments, the ELM4-ALK fusion protein is at least 85%, at least 90%, at least 95%, at least 98%, at least 99%, or 100% identical to an exemplary ELM4-ALK variant 1 fusion protein amino acid sequence from *Homo Sapiens* (GenBank: BAF73611.1) as provided below:

```
                                                   (SEQ ID NO: 15)
   1 mdgfagsldd sisaastsdv qdrlsalesr vqqqedeitv ikaaladvlr rlaisedhva

  61 svkksvsskg qpspravipm scitngsgan rkpshtsavs iagketlssa aksgtekkke

 121 kpqgqrekke eshsndqspq iraspspqps sqplqihrqt pesknatptk sikrpspaek

 181 shnswensdd srnklskips tpklipkvtk tadkhkdvii nqegeyikmf mrgrpitmfi

 241 psdvdnyddi rtelppeklk lewaygyrgk dcranvyllp tgeivyfias vvvlfnyeer

 301 tqrhylghtd cvkclaihpd kiriatgqia gvdkdgrplq phvrvwdsvt lstlqiiglg

 361 tfergvgcld fskadsgvhl cviddsnehm ltvwdwqkka kgaeikttne vvlavefhpt

 421 dantiitcgk shiffwtwsg nsltrkqgif gkyekpkfvq claflgngdv ltgdsggvml

 481 iwskttvept pgkgpkvyrr khqelqamqm elqspeykls klrtstimtd ynpnycfagk

 541 tssisdlkev prknitlirg lghgafgevy egqvsgmpnd psplqvavkt lpevcseqde

 601 ldflmealii skfnhqnivr cigvslqslp rfillelmag gdlksflret rprpsqpssl

 661 amldllhvar diacgcqyle enhfihrdia arncllltcpg pgrvakigdf gmardiyras

 721 yyrkggcaml pvkwmppeaf megiftsktd twsfgvllwe ifslgympyp sksnqevlef

 781 vtsggrmdpp kncpgpvyri mtqcwqhqpe drpnfaiile rieyctqdpd vintalpiey

 841 gplveeeekv pvrpkdpegv ppllvsqqak reeerspaap pplpttssgk aakkptaaev

 901 svrvprgpav egghvnmafs qsnppselhr vhgsrnkpts lwnptygswf tekptkknnp

 961 iakkepherg nlglegsctv ppnvatgrlp gaslllepss ltanmkevpl frlrhfpcgn

1021 vnygyqqqgl pleaatapga ghyedtilks knsmnqpgp
```

By "genetic vaccine" is meant an immunogenic composition comprising a polynucleotide encoding an antigen.

"Hybridization" means hydrogen bonding, which may be Watson-Crick, Hoogsteen, or reversed Hoogsteen hydrogen bonding, between complementary nucleobases. For example, in DNA, adenine and thymine, and cytosine and guanine, are, respectively, complementary nucleobases that pair through the formation of hydrogen bonds. By "hybridize" is meant pairing to form a double-stranded molecule between complementary polynucleotide sequences (e.g., a gene), or portions thereof, under various conditions of stringency. (See, e.g., Wahl, G. M. and S. L. Berger, (1987), *Methods Enzymol.,* 152:399; Kimmel, A. R., (1987), *Methods Enzymol.* 152:507).

By way of example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred: embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 μg/ml denatured salmon sperm DNA (ssDNA). In a most preferred embodiment, hybridization will occur at 42° C. in 250 mM NaCl, 25 mM trisodium citrate, 1% SDS, 50% formamide, and 200 μg/ml ssDNA. Useful variations on these conditions will be apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42 C in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be apparent to those skilled in the art. Hybridization techniques are well known to those skilled in the art and are described, for example, in Benton and Davis (*Science* 196:180, 1977); Grunstein and Hogness (*Proc. Natl. Acad. Sci., USA* 72:3961, 1975); Ausubel et al. (*Current Protocols in Molecular Biology*, Wiley Interscience, New York, 2001); Berger and Kimmel (*Guide to Molecular Cloning Techniques,* 1987, Academic Press, New York); and Sambrook et al., *Molecular Cloning: A Laboratory Manual*, Cold Spring Harbor Laboratory Press, New York.

By "immunogen" is meant an agent which is capable, under appropriate conditions, of eliciting or stimulating an immune response, such as the production a T-cell response, in an animal, including compositions that are injected or absorbed into an animal. As used herein, an "immunogenic composition" is a composition comprising an immunogen (such as an ALK polypeptide) or a vaccine comprising an immunogen (such as an ALK polypeptide). As will be appreciated by the skilled person in the art, if administered to a subject in need prior to the subject's contracting disease or experiencing full-blown disease, an immunogenic composition can be prophylactic and result in the subject's eliciting an immune response, e.g., a cellular immune response, to protect against disease, or to prevent more severe disease or condition, and/or the symptoms thereof. If administered to a subject in need following the subject's contracting disease, an immunogenic composition can be therapeutic and result in the subject's eliciting an immune response, e.g., a cellular immune response, to treat the disease, e.g., by reducing, diminishing, abrogating, ameliorating, or eliminating the disease, and/or the symptoms thereof. In some embodiments, the immune response is a B-cell response, which results in the production of antibodies, e.g., neutralizing antibodies, directed against the immunogen or immunogenic composition comprising the antigen or antigen sequence. In some embodiments, the immune response is a T-cell response, which results in the production of T-lymphocytes. In a manner similar to the foregoing, in some embodiments, an immunogenic composition or vaccine can be prophylactic. In some embodiments, an immunogenic composition or vaccine can be therapeutic. In some embodiments, the disease is caused by oncogenic ALK gene fusions, rearrangements, duplications or mutations (e.g., ALK-positive cancers). In some embodiments, the cancer is an ALK-positive cancer. In some embodiments, the ALK-positive cancer is non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, melanoma, or a combination thereof.

The term "immune response" is meant any response mediated by an immunoresponsive cell. In one example of an immune response, leukocytes are recruited to carry out a variety of different specific functions in response to exposure to an antigen (e.g., a foreign entity). Immune responses are multifactorial processes that differ depending on the type of cells involved. Immune responses include cell-mediated responses (e.g., T-cell responses), humoral responses (B-cell/antibody responses), innate responses and combinations thereof.

By "immunogenic composition" is meant a composition comprising an antigen, antigen sequence, or immunogen, wherein the composition elicits an immune response in an immunized subject.

The term "immunize" (or immunization) refers to rendering a subject protected from a disease or pathology, or the symptoms thereof, caused by oncogenic ALK gene fusions, rearrangements, duplications or mutations (e.g., ALK-positive cancers), such as by vaccination.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid, protein, or peptide is purified if it is substantially free of cellular material, debris, non-relevant viral material, or culture medium when produced by recombinant DNA techniques, or of chemical precursors or other chemicals when chemically synthesized. Purity and homogeneity are typically determined using standard purification methods and analytical chemistry techniques, for example, polyacrylamide gel electrophoresis or high-performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified. The term "isolated" also embraces recombinant nucleic acids or proteins, as well as chemically synthesized nucleic acids or peptides.

By "isolated polynucleotide" is meant a nucleic acid (e.g., a DNA molecule) that is free of the genes which flank the gene, in the naturally-occurring genome of the organism from which the nucleic acid molecule of the invention is derived. The term includes, for example, a recombinant DNA that is incorporated into a vector; into an autonomously replicating plasmid or virus; into the genomic DNA of a prokaryote or eukaryote; or that exists as a separate molecule independent of other sequences (for example, a cDNA or a genomic or cDNA fragment produced by PCR or restriction endonuclease digestion). In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 40%, by weight, at least 50%, by weight, at least 60%, by weight, free from the proteins and naturally-occurring organic molecules with which it is naturally associated. Preferably, an isolated polypeptide preparation is at least 75%, more preferably at least 90%, and most preferably at least 99%, by weight, free from the proteins and naturally-occurring organic molecules with which it is naturally associated. An isolated polypeptide may be obtained, for example, by extraction from a natural source; by expression of a recombinant nucleic acid encoding such a polypeptide; or by chemically synthesizing the protein.

Purity can be measured by any standard, appropriate method, for example, column chromatography, polyacrylamide gel electrophoresis, or by HPLC analysis. An isolated polypeptide can refer to an ALK antigen or immunogen polypeptide generated by the methods described herein.

By "linker" is meant one or more amino acids that serve as a spacer between two polypeptides or peptides of a fusion protein.

By "marker" is meant any protein or polynucleotide having an alteration in expression level or activity that is associated with a disease, condition, pathology, or disorder.

As used herein, "obtaining" as in "obtaining an agent" includes synthesizing, isolating, purchasing, or otherwise acquiring the agent.

The term "operably linked" refers to nucleic acid sequences as used herein. By way of example, a first nucleic acid sequence is operably linked to a second nucleic acid sequence when the first nucleic acid sequence is placed in a functional relationship with the second nucleic acid sequence. For instance, a promoter is operably linked to a coding sequence if the promoter affects (allows) the transcription or expression of the coding sequence. Generally, operably linked DNA sequences are contiguous and, where necessary to join two protein-coding regions, are in the same open reading frame.

The nucleic acid sequence encoding an ALK protein (antigen protein) generated by the described methods can be optimized for expression in mammalian cells via codon-optimization and RNA optimization (such as to increase RNA stability) using procedures and techniques practiced in the art.

By "open reading frame (ORF)" is meant a series of nucleotide triplets (codons) that code for amino acids without any termination codons. These sequences are usually translatable into a peptide or polypeptide.

The term "pharmaceutically acceptable vehicle" refers to conventional carriers (vehicles) and excipients that are physiologically and pharmaceutically acceptable for use, particularly in mammalian, e.g., human, subjects. Such pharmaceutically acceptable vehicles are known to the skilled practitioner in the pertinent art and can be readily found in *Remington's Pharmaceutical Sciences*, by E. W. Martin, Mack Publishing Co., Easton, Pa., 15th Edition (1975) and its updated editions, which describes compositions and formulations suitable for pharmaceutical delivery of one or more therapeutic or immunogenic compositions, such as one or more vaccines, and additional pharmaceutical agents. In general, the nature of a pharmaceutically acceptable carrier depends on the particular mode of administration being employed. For instance, parenteral formulations usually comprise injectable fluids/liquids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers may include, for example, pharmaceutical grades of mannitol, lactose, starch, or magnesium stearate, which typically stabilize and/or increase the half-life of a composition or drug. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

By "plasmid" is meant a circular nucleic acid molecule capable of autonomous replication in a host cell.

The terms "protein," "peptide," "polypeptide," and their grammatical equivalents are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three (3) amino acids long. A protein, peptide, or polypeptide can refer to an individual protein or a collection of proteins. One or more of the amino acids in a protein, peptide, or polypeptide can be modified, such as glycoproteins, for example, by the addition of a chemical entity such as a carbohydrate group, a hydroxyl group, a phosphate group, a farnesyl group, an isofamesyl group, a fatty acid group, a linker for conjugation, functionalization, or other modifications, etc. A protein, peptide, or polypeptide can also be a single molecule or can be a multi-molecular complex. A protein, peptide, or polypeptide can be just a fragment of a naturally occurring protein or peptide. A protein, peptide, or polypeptide can be naturally occurring, recombinant, or synthetic, or any combination thereof.

In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA or DNA. Any of the proteins provided herein can be produced by any method known in the art. For example, the proteins provided herein can be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference.

Conservative amino acid substitutions are those substitutions that, when made, least interfere with the properties of the original protein, that is, the structure and especially the function of the protein is conserved and is not significantly changed by such substitutions. Examples of conservative amino acid substitutions are known in the art, e.g., as set forth in, for example, U.S. Publication No. 2015/0030628. Conservative substitutions generally maintain (a) the structure of the polypeptide backbone in the area of the substitution, for example, as a sheet or helical conformation; (b) the charge or hydrophobicity of the molecule at the target site; and/or (c) the bulk of the side chain The substitutions that are generally expected to produce the greatest changes in protein properties are non-conservative, for instance, changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

By "promoter" is meant an array of nucleic acid control sequences, which direct transcription of a nucleic acid. A promoter includes necessary nucleic acid sequences near the start site of transcription. A promoter also optionally includes distal enhancer or repressor sequence elements. A "constitutive promoter" is a promoter that is continuously active and is not subject to regulation by external signals or molecules. In contrast, the activity of an "inducible promoter" is regulated by an external signal or molecule (for example, a transcription factor). By way of example, a promoter may be a CMV promoter.

As will be appreciated by the skilled practitioner in the art, the term "purified" does not require absolute purity; rather, it is intended as a relative term. Thus, for example, a purified peptide, protein, or other active compound is one that is isolated in whole or in part from naturally associated proteins and other contaminants. In certain embodiments, the term "substantially purified" refers to a peptide, protein, or other active compound that has been isolated from a cell, cell culture medium, or other crude preparation and subjected to routine methods, such as fractionation, chromatography, or electrophoresis, to remove various components of the initial preparation, such as proteins, cellular debris, and other components.

A "recombinant" nucleic acid or protein is one that has a sequence that is not naturally occurring or that has a sequence that is made by an artificial combination of two otherwise separated segments of sequence. Such an artificial combination is often accomplished by chemical synthesis or by the artificial manipulation of isolated segments of nucleic acids, for example, by genetic engineering techniques. A "non-naturally occurring" nucleic acid or protein is one that may be made via recombinant technology, artificial manipulation, or genetic or molecular biological engineering procedures and techniques, such as those commonly practiced in the art.

By "reduces" is meant a negative alteration of at least 5%, 10%, 25%, 30%, 40%, 50%, 75%, 80%, 85%, 90%, 95%, 98%, or 100%.

By "reference" is meant a standard or control condition.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, preferably at least about 20 amino acids, more preferably at least about 25 amino acids, and even more preferably about 35 amino acids, about 50 amino acids, or about 100 amino acids. For nucleic acids, the length of the reference nucleic acid sequence will generally be at least about 50 nucleotides, preferably at least about 60 nucleotides, more preferably at least about 75 nucleotides, and even more preferably about 100 nucleotides or about 300 nucleotides or any integer thereabout or therebetween.

By "specifically binds" is meant a compound or antibody that recognizes and binds a polypeptide, such as an ALK polypeptide, peptide, or vaccine product, but which does not substantially recognize and bind other molecules in a sample, for example, a biological sample, which naturally includes a polypeptide of the invention, such as an ALK polypeptide or peptide.

Nucleic acid molecules useful in the methods described herein include any nucleic acid molecule that encodes a polypeptide as described, or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Preferably, such a sequence is at least 60%, or at least 80% or 85%, or at least or equal to 90%, 95%, 98% or even 99% identical at the amino acid level or nucleic acid to the sequence used for comparison.

"Sequence identity" refers to the similarity between amino acid or nucleic acid sequences that is expressed in terms of the similarity between the sequences. Sequence identity is frequently measured in terms of percentage identity (or similarity or homology); the higher the percentage, the more similar the sequences are. Homologs or variants of a given gene or protein will possess a relatively high degree of sequence identity when aligned using standard methods. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence. In addition, other programs and alignment algorithms are described in, for example, Smith and Waterman, 1981, *Adv. Appl. Math.* 2:482; Needleman and Wunsch, 1970, *J. Mol. Biol.* 48:443; Pearson and Lipman, 1988, *Proc. Natl. Acad. Sci. U.S.A.* 85:2444; Higgins and Sharp, 1988, *Gene* 73:237-244; Higgins and Sharp, 1989, *CABIOS* 5:151-153; Corpet et al., 1988, *Nucleic Acids Research* 16:10881-10890; Pearson and Lipman, 1988, *Proc. Natl. Acad. Sci. U.S.A.* 85:2444; and Altschul et al., 1994, *Nature Genet.* 6:119-129. The NCBI Basic Local Alignment Search Tool (BLAST™) (Altschul et al. 1990, *J. Mol. Biol.* 215:403-410) is readily available from several sources, including the National Center for Biotechnology Information (NCBI, Bethesda, Md.) and on the Internet, for use in connection with the sequence analysis programs blastp, blastn, blastx, tblastn and tblastx.

By "subject" is meant an animal, e.g., a mammal, including, but not limited to, a human, a non-human primate, or a non-human mammal, such as a bovine, equine, canine, ovine, or feline mammal, or a sheep, goat, llama, camel, or a rodent (rat, mouse), gerbil, or hamster. In a nonlimiting example, a subject is one who has, is at risk of developing, or who is susceptible to a disease caused by oncogenic ALK gene fusions, rearrangements, duplications or mutations (e.g., ALK-positive cancers). In particular aspects as described herein, the subject is a human subject, such as a patient.

Ranges provided herein are understood to be shorthand for all of the values within the range, inclusive of the first and last stated values. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or greater, consecutively, such as to 100 or greater.

As used herein, the terms "treat," "treating," "treatment," and the like refer to reducing, diminishing, decreasing, delaying, abrogating, ameliorating, or eliminating, a disease, condition, disorder, or pathology, and/or symptoms associated therewith. While not intending to be limiting, "treating" typically relates to a therapeutic intervention that occurs after a disease, condition, disorder, or pathology, and/or symptoms associated therewith, have begun to develop to reduce the severity of the disease, etc., and the associated signs and symptoms. It will be appreciated that, although not precluded, treating a disorder or condition does not require that the disease, condition, disorder, pathology, or the symptoms associated therewith, be completely eliminated.

As used herein, the terms "prevent," "preventing," "prevention," "prophylactic treatment" and the like, refer to inhibiting or blocking a disease state, or the full development of a disease in a subject, or reducing the probability of developing a disease, disorder or condition in a subject, who does not have, but is at risk of developing, or is susceptible to developing, a disease, disorder, or condition.

As referred to herein, a "transformed" or "transfected" cell is a cell into which a nucleic acid molecule or polynucleotide sequence has been introduced by molecular biology techniques. As used herein, the term "transfection" encompasses all techniques by which a nucleic acid molecule or polynucleotide may be introduced into such a cell, including transfection with viral vectors, transformation with plasmid vectors, and introduction of naked nucleic acid (DNA or RNA) by electroporation, lipofection, and particle gun acceleration.

By "vaccine" is meant a preparation of immunogenic material (e.g., protein or nucleic acid; vaccine) capable of stimulating (eliciting) an immune response, administered to a subject to treat a disease, condition, or pathology, or to prevent a disease, condition, or pathology caused by oncogenic ALK gene fusions, rearrangements, duplications or mutations (e.g., ALK-positive cancers). The immunogenic material may include, for example, antigenic proteins, peptides or DNA derived from ALK-expressing tumors or cell lines. Vaccines may elicit a prophylactic (preventative) immune response in the subject; they may also elicit a therapeutic response immune response in a subject. As mentioned above, methods of vaccine administration vary according to the vaccine, and can include routes or means, such as inoculation (intravenous or subcutaneous injection), ingestion, inhalation, or other forms of administration. Inoculations can be delivered by any number of routes, including parenteral, such as intravenous, subcutaneous or intramuscular. Vaccines may also be administered with an adjuvant to boost the immune response.

As used herein, a "vector" refers to a nucleic acid (polynucleotide) molecule into which foreign nucleic acid can be inserted without disrupting the ability of the vector to replicate in and/or integrate into a host cell. A vector can include nucleic acid sequences that permit it to replicate in a host cell, such as an origin of replication. An insertional vector is capable of inserting itself into a host nucleic acid. A vector can also include one or more selectable marker genes and other genetic elements. An expression vector is a vector that contains the necessary regulatory sequences to allow transcription and translation of inserted gene or genes in a host cell. In some embodiments of the present disclosure, the vector encodes an ALK protein. In some embodiments, the vector is the pTR600 expression vector (U.S. Patent Application Publication No. 2002/0106798; Ross et al., 2000, *Nat Immunol.* 1(2):102-103; and Green et al., 2001, *Vaccine* 20:242-248).

Unless specifically stated or obvious from context, as used herein, the term "or" is understood to be inclusive. Unless specifically stated or obvious from context, as used herein, the terms "a," "an," and "the" are understood to be singular or plural. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description.

Unless specifically stated or obvious from context, as used herein, the term "about" is understood as within a range of normal tolerance in the art, for example within two (2) standard deviations (SD) of the mean. About may be understood as being within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of some embodiments for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 1A shows a western blot of transduced B721.221/A*02:01, B721.221/A*01:01 and B721.221/C*06:02 cells with a construct encoding the EML4-ALK variant 1 and GFP. Cells were sorted based on the GFP positivity and expanded. The untransduced B721.221/A*02:01 cell line was used as a negative control and the H3122 ALK+NSCLC cell line was used as a positive control. FIG. 1B provides graphical depictions of targeted mass spectrometry in HLA*02:01 elute from B721.221/A*02:01 cells measuring endogenous un-labeled peptides (light peptides) and two algorithm predicted isotope-labeled ALK-specific peptides, AMLDLLHVA (SEQ ID NO: 1) and SLAMLDLLHV (SEQ ID NO: 16) (heavy standard).

FIG. 2A provides graphical depictions of targeted mass spectrometry in HLA*02:01 elute from DEL cells measuring endogenous un-labeled peptides (light peptides) and two algorithm predicted isotope-labeled ALK-specific peptides, AMLDLLHVA (SEQ ID NO: 1) and SLAMLDLLHV (SEQ ID NO: 16) (heavy standard). FIG. 2B provides a graphical depiction of the IVRCIGVSL (SEQ ID NO: 3) ALK-peptide identified by discovery mass spectrometry in the pan-HLA elute from the Karpas-299 cell line and a table depicting the assignment of the ALK-peptide to an HLA allele. Karpas-299 alleles are shown in bold font. FIG. 2C provides a graphical depiction of the RPRPSQPSSL (SEQ ID NO: 2) ALK-peptide identified by discovery mass spectrometry in the pan-HLA elute from the Karpas-299 cell line and a table depicting the assignment of the ALK-peptide to an HLA allele. Karpas-299 alleles are shown in bold font. FIG. 2D provides a graphical depiction of the VPRKNITLI (SEQ ID NO: 4) ALK-peptide identified by discovery mass spectrometry in the pan-HLA elute from the Karpas-299 cell line and a table depicting the assignment of the ALK-peptide to an HLA allele. Karpas-299 alleles are shown in bold font. FIG. 2D discloses "PRKNITLI" as SEQ ID NO: 74.

FIG. 4A shows images of an interferon-gamma (IFN-γ) ELISPOT assay challenged with splenocytes from two (2) C57BL/6-Mcph1$^{Tg(HLA-A2.1)1Enge}$/j transgenic mice vaccinated with AMLDLLHVA (SEQ ID NO: 1) together with Freund's complete adjuvant. Splenocytes were challenged with either the ALK peptide, OVA peptide (negative control), or media (negative control) in an IFN-γ-ELISPOT assay. FIG. 4B is a graphical depiction measuring the INF-γ spot forming units (SFU) between wells with splenocytes challenged with AMLDLLHVA (SEQ ID NO: 1) and those wells challenged with OVA-peptide from the two (2) C57BL/6-Mcph1$^{Tg(HLA-A2.1)1Enge}$/J mice vaccinated with AMLDLLHVA (SEQ ID NO: 1). Error bars mean SD. FIG. 4C shows images of a direct IFN-γ ELISPOT assay challenged with PBMCs from ALK-positive NSCLC HLA*02:01 patients with AMLDLLHVA (SEQ ID NO: 1). HIV peptide and no peptide stimulation were used as negative controls. HLA*02:01-specific Flu matrix peptide was used as a positive control.

FIG. 5A depicts an illustrative scheme of the protocol followed for peptide-specific $CD8^+$ T-cell expansion. PBMCs from ALK-positive NSCLC HLA*07:02 patients were thawed and rested overnight in the presence of rh-IL-7 at day-1. At day 0, PBMCs were stimulated alternatively with IVRCIGVSL (SEQ ID NO: 3) or RPRPSQPSSL (SEQ ID NO: 2). From day 3, and every 3-4 days, fresh media containing rh-IL-2 and rh-IL-7 was added. Second and third stimulation was done by incubating purified $CD8^+$ T-cells with peptide-pulsed mature DCs (mDCs) or CD40-activated B-cells, respectively. IFN-γ ELISPOT was performed as a read out of the expansion at day 21. FIG. 5B shows images of an IFN-γ ELISPOT assay of IVRCIGVSL-expanded (SEQ ID NO: 3) $CD8^+$ T-cells challenged with B-cells pulsed with different peptides. HIV-pulsed and non-pulsed B-cells were used as negative controls. CEF plus-pulsed B-cells were used as positive control. FIG. 5B discloses "RPRPSQPSSL" as SEQ ID NO: 2. FIG. 5C is a graphical depiction measuring the INF-γ spot forming units (SFU) between wells challenged with IVRCIGVSL-pulsed (SEQ ID NO: 3) B-cells and those wells with B-cells pulsed with control peptides. HIV-pulsed and non-pulsed B-cells were used as negative controls. Error bars mean SD. FIG. 5C discloses "RPRPSQPSSL" as SEQ ID NO: 2.

FIG. 6A depicts a schematic illustration of amphiphile-peptide vaccine function by binding to endogenous albumin present in interstitial fluid following injection, with subsequent albumin-mediated transport to lymph nodes for efficient capture by dendritic cells. FIG. 6B is a graphical depiction of $CD4^+$ and $CD8^+$ T-cell responses in Balb/c mice immunized with a series of different ALK peptides and then assayed for ex vivo antigen-specific cytokine production. No peptide and naïve peptide were used as negative controls. FIG. 6C is a graphical depiction of the number of tumors assessed 14 days after Balb/c mice were immunized with a series of different ALK peptides. Naïve peptide was used as a negative control.

FIG. 7A depicts a schematic illustration of ALK-peptide vaccination administration for either naked ALK-peptide or amphiphilic-conjugated ALK-peptide monotherapy. FIG. 7B depicts a schematic illustration of ALK-peptide vaccination administration for ALK-peptide (naked or amphiphilic-conjugated) in combination therapy with a PD-1 inhibitor.

FIG. 8A depicts a schematic illustration of a vaccination administration schedule for mice with NSCLC cell induced lung tumors treated with an ALK-peptide in combination with lorlatinib and anti-PD-1 antibodies. FIG. 8B is a graphical depiction of Kaplan-Meyer survival curves of mice with NSCLC cell induced lung tumors treated with either control, lorlatinib, lorlatinib with anti-PD-1 antibodies, lorlatinib with ALK-peptide vaccine, or lorlatinib with ALK-peptide vaccine and anti-PD-1 antibodies.

DETAILED DESCRIPTION OF THE INVENTION

Figure 1A:
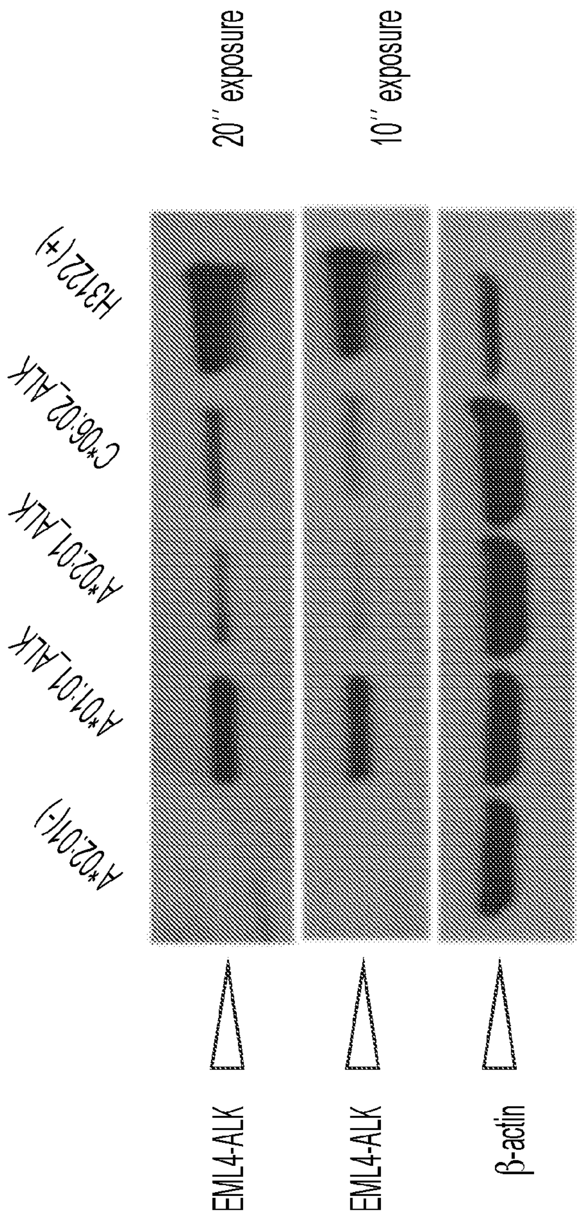
FIGS. 1A and 1B depict the identification of ALK-specific peptides in B721.221/HLA monoallelic cells.

Lung cancer is the most common cause of cancer-related death worldwide, and the annual incidence of anaplastic lymphoma kinase (ALK) expressing non-small cell lung cancer (NSCLC) in the U.S. is about 8,000 cases. In these patients, treatment with ALK tyrosine kinase inhibitors (TKIs) fails to induce durable remissions. In this context, a successful ALK vaccine could lead to durable responses and greatly improve survival and quality of life for NSCLC patients. ALK represents an attractive target for vaccine development because of its oncogenicity, its immunogenicity, and its restricted expression to tumor tissue rather than healthy adult tissue. Importantly, use of a therapeutic ALK peptide vaccine could potentially be extended to many other cancer types which are driven by ALK rearrangements or activating mutations (i.e., ALK-positive cancers), such as anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, and melanoma. Therefore, a vaccine as described herein generated against the rearranged portion of ALK can both prevent the development of ALK-positive tumors and more effectively treat patients diagnosed with ALK-positive tumors.

As described below, the present invention features isolated ALK-specific immunogenic antigens, e.g., peptide antigens, derived from ALK-positive cell lines and immune cells from patients with ALK-positive cancers. Such immunogenic antigens are also referred to as "immunogens" herein. The ALK-specific immunogenic antigens elicit a potent immune response, e.g., in the form of reactive T-lymphocytes, following administration or delivery to, or introduction into, a subject, particularly, a human subject. The isolated ALK-specific immunogenic antigens may be used in methods to treat and/or reduce disease caused by oncogenic ALK gene fusions, rearrangements, duplications or mutations. The isolated ALK-specific immunogenic antigens may be conjugated to an amphiphilic tail in order to significantly increase T-cell expansion and greatly enhance anti-tumor efficacy.

The immunogenic ALK antigens described herein may be used in immunogenic compositions (e.g., ALK-specific vaccines) that treat ALK-positive cancers caused by oncogenic ALK gene fusions, rearrangements, duplications or mutations in a subject, particularly a human subject, to whom the immunogenic composition or vaccine, is administered. The vaccine elicits a potent ALK protein-specific T cell response that treats and/or protects against ALK-positive cancers in a subject. The antigens, immunogens, immunogenic compositions and vaccines, and pharmaceutical compositions thereof, of the invention provide an additional treatment option for patients that have either become resistant to or have failed to respond to prior and traditional therapies for ALK-positive cancers.

Identification of ALK Proteins

The use of computational algorithms has been successfully applied in recent studies to identify T-cell neoantigens in both human and mice. (Carreno B M, et al. Cancer immunotherapy. A dendritic cell vaccine increases the breadth and diversity of melanoma neoantigen-specific T-cells. Science. 2015; 348(6236):803-808; Gubin M M, et al. Checkpoint blockade cancer immunotherapy targets tumour-specific tumor antigens. Nature. 2014; 515(7528): 577-581). However, these algorithms are almost exclusively based on the affinities of synthetic peptides, and do not necessarily consider other parameters such as antigen expression levels, intracellular processing, and the transport of the peptides prior to HLA binding. Altogether, these factors can significantly limit the accuracy of the current algorithms in predicting genuine T-cell epitopes.

By using a liquid chromatography-tandem mass spectrometry (LC-MS/MS) analysis of the peptides presented on the surface of HLA monoallelic cells, only 26% of the peptides that actually bind common HLA alleles were predicted by Immune Epitope Database (IEDB) algorithms, one of the most commonly used algorithms (www.iedb.org). (Abelin J G, et al. Mass Spectrometry Profiling of HLA-Associated Peptidomes in Mono-allelic Cells Enables More Accurate Epitope Prediction. Immunity. 2017; 46(2):315-326). The level of accuracy drops down to 0% for rare HLA alleles. Thus, current algorithms used to predict antigenic peptides are generally inaccurate and misleading as to which antigens are actually presented on tumor cell surfaces. (See Abelin J G, et al. Mass Spectrometry Profiling of HLA-Associated Peptidomes in Mono-allelic Cells Enables More Accurate Epitope Prediction. Immunity. 2017; 46(2):315-326).

For direct identification of ALK antigenic peptides effectively presented on the cell surface of tumor cells in the most common HLA haplotypes, the HLA monoallelic cell system and algorithms as provided in Abelin J G, et al. (Mass Spectrometry Profiling of HLA-Associated Peptidomes in Mono-allelic Cells Enables More Accurate Epitope Prediction. Immunity. 2017; 46(2):315-326), which is incorporated herein in its entirety, were adapted. To directly identify ALK peptides actually presented on the surface of ALK-expressing tumor cells, HLA-peptide complexes were pulled from ALK-expressing cell lines lysates and the HLA-bound peptides were analyzed using liquid chromatography-tandem mass spectrometry (LC-MS/MS).

The invention provides for a method for identifying the ALK-specific peptides provided herein as described in Example 1. In some embodiments, the ALK-expressing cell lines for use in identifying the ALK antigenic peptides provided herein encode specific HLA-alleles (e.g., HLA class I alleles) and may express or may be transduced with a construct to express an ALK fusion protein. In some embodiments, the ALK-expressing cells lines are generated as described in Abelin J G, et al. (Mass Spectrometry Profiling of HLA-Associated Peptidomes in Mono-allelic Cells Enables More Accurate Epitope Prediction. Immunity. 2017; 46(2):315-326), which is incorporated herein in its entirety. In some embodiments, the HLA is encoded by a HLA class I allele. Nonlimiting examples of HLA class I alleles expressed by ALK-expressing cell lines are provided in Table 1, Table 2 or Table 3. In some embodiments, the HLA class I allele is HLA A*02:01, HLA A*68:02, HLA B*07:02, or HLA C*07:02.

In some embodiments, the fusion protein is an ALK protein fused to an echinoderm microtubule-associated protein-like 4 (EML4) protein (ELM4-ALK). In some embodiments, the ELM4-ALK fusion protein is at least 85%, at least 90%, at least 95%, at least 98%, at least 99%, or 100% identical to a ELM4-ALK fusion protein in *Homo Sapiens* or a variant thereof. In some embodiments, the ELM4-ALK fusion protein is at least 85%, at least 90%, at least 95%, at least 98%, at least 99%, or 100% identical to an exemplary ELM4-ALK fusion protein amino acid sequence from *Homo Sapiens* (GenBank: BAM37627.1) as provided below:

```
                                                                   (SEQ ID NO: 13)
  1 mdgfagsldd sisaastsdv qdrlsalesr vqqqedeitv lkaaladvlr rlaisedhva

 61 svkksvsskg qpspravipm scitngsgan rkpshtsavs iagketlssa aksgtekkke

121 kpqgqrekke eshsndqspq iraspspqps sqplqihrqt pesknatptk sikrpspaek

181 shnswensdd srnklskips tpklipkvtk tadkhkdvii nqegeyikmf mrgrpitmfi

241 psdvdnyddi rtelppeklk lewaygyrgk dcranvyllp tgeivyfias vvvlfnyeer

301 tqrhylghtd cvkclaihpd kiriatgqia gvdkdgrplq phvrvwdsvt lstlqiiglg

361 tfergvgcld fskadsgvhl cviddsnehm ltvwdwqrka kgaeikttne vvlavefhpt

421 dantiitcgk shiffwtwsg nsltrkqgif gkyekpkfvq claflgngdv ltgdsggvml

481 iwskttvept pgkgpkgvyq iskqikahdg svftlcqmrn gmlltgggkd rkiilwdhdl

541 npereiefsa srarlpghva adhppavyrr khqelqamqm elqspeykls klrtstimtd

601 ynpnycfagk tssisdlkev prknitlirg lghgafgevy egqvsgmpnd psplqvavkt
```

-continued

```
 661 lpevcseqde ldflmealii skfnhqnivr cigvslqslp rfillelmag gdlksflret
 721 rprpsqpssl amldllhvar diacgcqyle enhfihrdia arnclltcpg pgrvakigdf
 781 gmardiyras yyrkggcaml pvkwmppeaf megiftsktd twsfgvllwe ifslgympyp
 841 sksnqevlef vtsggrmdpp kncpgpvyri mtqcwqhqpe drpnfaiile rieyctqdpd
 901 vintalpiey gplveeeekv pvrpkdpegv ppllvsqqak reeerspaap pplpttssgk
 961 aakkptaaei svrvprgpav egghvnmafs qsnppselhk vhgsrnkpts lwnptygswf
1021 tekptkknnp iakkephdrg nlglegsctv ppnvatgrlp gaslllepss ltanmkevpl
1081 frlrhfpcgn vnygyqqqgl pleaatapga ghyedtilks knsmnqpgp
```

In some embodiments, the ELM4-ALK fusion protein is encoded by a nucleic acid sequence from *Homo Sapiens* that is at least 85%, at least 90%, at least 95%, at least 98%, at least 99%, or 100% identical to GenBank: AB274722.1 as provided below:

```
                                                        (SEQ ID NO: 14)
   1   ggcggcgcgg cgcggcgctc gcggctgctg cctgggaggg aggccgggca ggcggctgag
  61   cggcgcggct ctcaacgtga cggggaagtg gttcgggcgg ccgcggctta ctaccccagg
 121   gcgaacggac ggacgacgga ggcgggagcc ggtagccgag ccgggcgacc tagagaacga
 181   gcgggtcagg ctcagcgtcg gccactctgt cggtccgctg aatgaagtgc ccgcccctct
 241   gagcccggag cccggcgctt tccccgcaag atggacggtt tcgccggcag tctcgatgat
 301   agtatttctg ctgcaagtac ttctgatgtt caagatcgcc tgtcagctct tgagtcacga
 361   gttcagcaac aagaagatga aatcactgtg ctaaaggcgg ctttggctga tgttttgagg
 421   cgtcttgcaa tctctgaaga tcatgtggcc tcagtgaaaa aatcagtctc aagtaaaggc
 481   caaccaagcc ctcgagcagt tattcccatg tcctgtataa ccaatggaag tggtgcaaac
 541   agaaaaccaa gtcataccag tgctgtctca attgcaggaa aagaaactct ttcatctgct
 601   gctaaaagtg gtacagaaaa aaagaaagaa aaaccacaag gacagagaga aaaaaaagag
 661   gaatctcatt ctaatgatca aagtccacaa attcgagcat caccttctcc ccagcccctct
 721   tcacaacctc tccaaataca cagacaaact ccagaaagca agaatgctac tcccaccaaa
 781   agcataaaac gaccatcacc agctgaaaag tcacataatt cttgggaaaa ttcagatgat
 841   agccgtaata aattgtcgaa aataccttca acacccaaat taataccaaa agttaccaaa
 901   actgcagaca agcataaaga tgtcatcatc aaccaagaag gagaatatat taaaatgttt
 961   atgcgcggtc ggccaattac catgttcatt ccttccgatg ttgacaacta tgatgacatc
1021   agaacggaac tgcctcctga gaagctcaaa ctggagtggg catatggtta tcgaggaaag
1081   gactgtagag ctaatgttta ccttcttccg accggggaaa tagtttattt cattgcatca
1141   gtagtagtac tatttaatta tgaggagaga actcagcgac actacctggg ccatacagac
1201   tgtgtgaaat gccttgctat acatcctgac aaaattagga ttgcaactgg acagatagct
1261   ggcgtggata aagatggaag gcctctacaa ccccacgtca gagtgtggga ttctgttact
1321   ctatccacac tgcagattat tggacttggc acttttgagc gtggagtagg atgcctggat
1381   ttttcaaaag cagattcagg tgttcattta tgtgttattg atgactccaa tgagcatatg
1441   cttactgtat gggactggca gaagaaagca aaaggagcag aaataaagac aacaaatgaa
1501   gttgttttgg ctgtggagtt tcacccaaca gatgcaaata ccataattac atgcggtaaa
1561   tctcatattt tcttctggac ctggagcggc aattcactaa caagaaaaca gggaattttt
1621   gggaaatatg aaaagccaaa atttgtgcag tgtttagcat tcttggggaa tggagatgtt
```

-continued

```
1681   cttactggag actcaggtgg agtcatgctt atatggagca aaactactgt agagcccaca
1741   cctgggaaag gacctaaagt gtaccgccgg aagcaccagg agctgcaagc catgcagatg
1801   gagctgcaga gccctgagta caagctgagc aagctccgca cctcgaccat catgaccgac
1861   tacaacccca actactgctt tgctggcaag acctcctcca tcagtgacct gaaggaggtg
1921   ccgcggaaaa acatcaccct cattcggggt ctgggccatg gagcctttgg ggaggtgtat
1981   gaaggccagg tgtccggaat gcccaacgac ccaagccccc tgcaagtggc tgtgaagacg
2041   ctgcctgaag tgtgctctga acaggacgaa ctggatttcc tcatggaagc cctgatcatc
2101   agcaaattca accaccagaa cattgttcgc tgcattgggg tgagcctgca atccctgccc
2161   cggttcatcc tgctggagct catggcgggg ggagacctca agtccttcct ccgagagacc
2221   cgccctcgcc cgagccagcc ctcctccctg gccatgctgg accttctgca cgtggctcgg
2281   gacattgcct gtggctgtca gtatttggag gaaaaccact tcatccaccg agacattgct
2341   gccagaaact gcctcttgac ctgtccaggc cctggaagag tggccaagat tggagacttc
2401   gggatggccc gagacatcta cagggcgagc tactatagaa agggaggctg tgccatgctg
2461   ccagttaagt ggatgccccc agaggccttc atggaaggaa tattcacttc taaaacagac
2521   acatggtcct ttggagtgct gctatgggaa atcttttctc ttggatatat gccatacccc
2581   agcaaaagca accaggaagt tctggagttt gtcaccagtg gaggccggat ggacccaccc
2641   aagaactgcc ctgggcctgt ataccggata atgactcagt gctggcaaca tcagcctgaa
2701   gacaggccca actttgccat cattttggag aggattgaat actgcaccca ggacccggat
2761   gtaatcaaca ccgctttgcc gatagaatat ggtccacttg tggaagagga agagaaagtg
2821   cctgtgaggc ccaaggaccc tgaggggggtt cctcctctcc tggtctctca acaggcaaaa
2881   cgggaggagg agcgcagccc agctgcccca ccacctctgc ctaccacctc ctctggcaag
2941   gctgcaaaga aacccacagc tgcagaggtc tctgttcgag tccctagagg gccggccgtg
3001   gaagggggac acgtgaatat ggcattctct cagtccaacc ctccttcgga gttgcacagg
3061   gtccacggat ccagaaacaa gcccaccagc ttgtggaacc caacgtacgg ctcctggttt
3121   acagagaaac ccaccaaaaa gaataatcct atagcaaaga aggagccaca cgagaggggt
3181   aacctggggc tggagggaag ctgtactgtc ccacctaacg ttgcaactgg gagacttccg
3241   ggggcctcac tgctcctaga gccctcttcg ctgactgcca atatgaagga ggtacctctg
3301   ttcaggctac gtcacttccc ttgtgggaat gtcaattacg gctaccagca acagggcttg
3361   cccttagaag ccgctactgc ccctggagct ggtcattacg aggataccat tctgaaaagc
3421   aagaatagca tgaaccagcc tgggccctga gctcggtcac acactcactt ctcttccttg
3481   ggatccctaa gaccgtggag gagagagagg caatcaatgg ctccttcaca aaccagagac
3541   caaatgtcac gttttgtttt gtgccaacct attttgaagt accaccaaaa aagctgtatt
3601   ttgaaaatgc tttagaaagg ttttgagcat gggttcatcc tattctttcg aaagaagaaa
3661   atatcataaa aatgagtgat aaatacaagg cccagatgtg gttgcataag gtttttatgc
3721   atgtttgttg tatacttcct tatgcttctt ttaaattgtg tgtgctctgc ttcaatgtag
3781   tcagaattag ctgcttctat gtttcatagt tggggtcata gatgtttcct tgccttgttg
3841   atgtggacat gagccatttg aggggagagg gaacggaaat aaaggagtta tttgtaatga
3901   aaaaaaaaaa aaaaaaaaaa aaaaaa
```

In some embodiments, the ALK-expressing cell line may include the B721.221 human lymphoblastic cell line, which does not express endogenous HLA class I (A, B and C) due to gamma-ray-induced mutations in the HLA complex. (Shimizu Y, DeMars R. Production of human cells expressing individual transferred HLA-A, -B, -C genes using an HLA-A, -B, -C null human cell line. *J. Immunol.* 1989; 142(9):3320-3328). In some embodiments, the B721.221 cell line is transduced with a construct encoding an EML4-ALK fusion protein. In some embodiments, the construct encodes EML4-ALK variant 1, the most frequent EML4-ALK fusion protein (Lin J J, et al. Impact of EML4-ALK Variant on Resistance Mechanisms and Clinical Outcomes in ALK-Positive Lung Cancer. J. Clin. Oncol. 2018: JC02017762294). In one embodiment, the ELM4-ALK variant 1 fusion protein has an amino acid sequence from *Homo Sapiens* that is at least 85%, at least 90%, at least 95%, at least 98%, at least 99%, or 100% identical to GenBank: BAF73611.1 as provided below:

(SEQ ID NO: 10)

MEDSMDMDMSPLRPQNYLFGCELKADKDYHFKVDNDENEHQLSLRTVSLG

AGAKDELHIVEAEAMNYEGSPIKVTLATLKMSVQPTVSLGGFEITPPVVL

RLKCGSGPVHISGQHLVVYRRKHQELQAMQMELQSPEYKLSKLRTSTIMT

DYNPNYCFAGKTSSISDLKEVPRKNNTLIRGLGHGAFGEVYEGQVSGMPN

DPSPLQVAVKTLPEVCSEQDELDFLMEALIISKFNHQNIVRCIGVSLQSL

PRFILLELMAGGDLKSFLRETRPRPSQPSSLAMLDLLHVARDIACGCQYL

EENHFIHRDIAARNCLLTCPGPGRVAKIGDFGMARDIYRASYYRKGGCAM

LPVKWMPPEAFMEGIFTSKTDTWSFGVLLWEIFSLGYMPYPSKSNQEVLE

FVTSGGRMDPPKNCPGPVYRIMTQCWQHQPEDRPNFAIILERIEYCTQDP

DVINTALPIEYGPLVEEEEKVPVRPKDPEGVPPLLVSQQAKREEERSPAA

(SEQ ID NO: 15)

```
   1 mdgfagsldd sisaastsdv qdrlsalesr vqqqedeitv lkaaladvlr rlaisedhva
  61 svkksvsskg qpspravipm scitngsgan rkpshtsavs iagketlssa aksgtekkke
 121 kpqgqrekke eshsndqspq iraspspqps sqplqihrqt pesknatptk sikrpspaek
 181 shnswensdd srnklskips tpklipkvtk tadkhkdvii nqegeyikmf mrgrpitmfi
 241 psdvdnyddi rtelppeklk lewaygyrgk dcranvyllp tgeivyfias vvvlfnyeer
 301 tqrhylghtd cvkclaihpd kiriatgqia gvdkdgrplq phvrvwdsvt lstlqiiglg
 361 tfergvgcld fskadsgvhl cviddsnehm ltvwdwqkka kgaeikttne vvlavefhpt
 421 dantiitcgk shiffwtwsg nsltrkqgif gkyekpkfvq claflgngdv ltgdsggvml
 481 iwskttvept pgkgpkvyrr khqelqamqm elqspeykls klrtstimtd ynpnycfagk
 541 tssisdlkev prknitlirg lghgafgevy egqvsgmpnd psplqvavkt lpevcseqde
 601 ldflmealii skfnhqnivr cigvslqslp rfillelmag gdlksflret rprpsqpssl
 661 amldllhvar diacgcqyle enhfihrdia arnclltcpg pgrvakigdf gmardiyras
 721 yyrkggcaml pvkwmppeaf megiftsktd twsfgvllwe ifslgympyp sksnqevlef
 781 vtsggrmdpp kncpgpvyri mtqcwqhqpe drpnfaiile rieyctqdpd vintalpiey
 841 gplveeeekv pvrpkdpegv ppllvsqqak reeerspaap pplpttssgk aakkptaaev
 901 svrvprgpav egghvnmafs qsnppselhr vhgsrnkpts lwnptygswf tekptkknnp
 961 iakkepherg nlglegsctv ppnvatgrlp gaslllepss ltanmkevpl frlrhfpcgn
1021 vnygyqqqgl pleaatapga ghyedtilks knsmnqpgp
```

In some embodiments, the fusion protein is an ALK protein fused to a nucleophosmin (NPM) protein (NPM-ALK). In some embodiments, ALK-expressing cell lines may include anaplastic large cell lymphoma (ALCL) cell lines encoding frequent HLA-alleles (e.g., Karpas-299, DEL, and SR-786). These ALCL cell lines express high levels of the NPM-ALK fusion protein. In some embodiments, the NPM-ALK fusion protein is at least 85%, at least 90%, at least 95%, at least 98%, at least 99%, or 100% identical to a NPM-ALK fusion protein in *Homo Sapiens*. In some embodiments, the NPM-ALK fusion protein is at least 85%, at least 90%, at least 95%, at least 98%, at least 99%, or 100% identical to an exemplary NPM-ALK fusion protein amino acid sequence from *Homo Sapiens* as provided below (ALK cytoplasmic portion in bold font):

-continued

PPPLPTTSSGKAAKKPTAAEVSVRVPRGPAVEGGHVNMAFSQSNPPSELH

RVHGSRNKPTSLWNPTYGSWFTEKPTKKNNPIAKKEPHERGNLGLEGSCT

VPPNVATGRLPGASLLLEPSSLTANMKEVPLFRLRHFPCGNVNYGYQQQG

LPLEAATAPGAGHYEDTILKSKNSMNQPGP

In some embodiments, the NPM-ALK fusion protein is at least 85%, at least 90%, at least 95%, at least 98%, at least 99%, or 100% identical to an exemplary NPM-ALK fusion protein amino acid sequence from *Homo Sapiens* (GenBank: AAA58698.1) as provided below:

(SEQ ID NO: 11)
```
1   medsmdmdms plrpqnylfg celkadkdyh fkvdndeneh qlslrtvslg agakdelhiv
61  eaeamnyegs pikvtlatlk msvqptvslg gfeitppvvl rlkcgsgpvh isgqhlvvyr
121 rkhqelqamq melqspeykl sklrtstimt dynpnycfag ktssisdlke vprknitlir
181 glghgafgev yegqvsgmpn dpsplqvavk tlpevcseqd eldflmeali iskfnhqniv
241 rcigvslqsl prfillelma ggdlksflre trprpsqpss lamldllhva rdiacgcqyl
301 eenhfihrdi aarnclltcp gpgrvakigd fgmardiyra syyrkggcam lpvkwmppea
361 fmegiftskt dtwsfgvllw eifslgympy psksnqevle fvtsggrmdp pkncpgpvyr
421 imtqcwqhqp edrpnfaiil erieyctqdp dvintalpie ygplveeeek vpvrpkdpeg
481 vppllvsqqa kreeerspaa ppplpttssg kaakkptaae vsvrvprgpa vegghvnmaf
541 sqsnppselh kvhgsrnkpt slwnptygsw ftekptkknn piakkephdr gnlglegsct
601 vppnvatgrl pgaslllleps sltanmkevp lfrlrhfpcg nvnygyqqqg lpleaatapg
661 aghyedtilk sknsmnqpgp
```

In some embodiments, the NPM-ALK fusion protein is at least 85%, at least 90%, at least 95%, at least 98%, at least 99%, or 100% identical to an exemplary NPM-ALK fusion protein amino acid sequence from *Homo Sapiens* as provided below:

(SEQ ID NO: 17)
```
M E D S M D M D M S P L R P Q N Y L F G
C E L K A D K D Y H F K V D N D E N E H
Q L S L R T V S L G A G A K D E L H I V
E A E A M N Y E G S P I K V T L A T L K
M S V Q P T V S L G G F E I T P P V V L
R L K C G S G P V H I S G Q H L V V Y R
R K H Q E L Q A M Q M E L Q S P E Y K L
S K L R T S T I M T D Y N P N Y C F A G
K T S S I S D L K E V P R K N I T L I R
G L G H G A F G E V Y E G Q V S G M P N
D P S P L Q V A V K T L P E V C S E Q D
E L D F L M E A L I I S K F N H Q N I V
R C I G V S L Q S L P R F I L L E L M A
G G D L K S F L R E T R P R P S Q P S S
L A M L D L L H V A R D I A C G C Q Y L
E E N H F I H R D I A A R N C L L T C P
G P G R V A K I G D F G M A R D I Y R A
```

-continued
```
S Y Y R K G G C A M L P V K W M P P E A
F M E G I F T S K T D T W S F G V L L W
E I F S L G Y M P Y P S K S N Q E V L E
F V T S G G R M D P P K N C P G P V Y R
I M T Q C W Q H Q P E D R P N F A I I L
E R I E Y C T Q D P D V I N T A L P I E
Y G P L V E E E E K V P V R P K D P E G
V P P L L V S Q Q A K R E E E R S P A A
P P P L P T T S S G K A A K K P T A A E
V S V R V P R G P A V E G G H V N M A F
S Q S N P P S E L H K V H G S R N K P T
S L W N P T Y G S W F T E K P T K K N N
P I A K K E P H D R G N L G L E G S C T
V P P N V A T G R L P G A S L L L E P S
S L T A N M K E V P L F R L R H F P C G
N V N Y G Y Q Q Q G L P L E A A T A P G
A G H Y E D T I L K S K N S M N Q P G P
*
```

In some embodiments, an exemplary NPM-ALK fusion protein is encoded by a nucleic acid sequence from *Homo Sapiens* that is at least 85%, at least 90%, at least 95%, at least 98%, at least 99%, or 100% identical to the sequence provided below:

(SEQ ID NO: 12)
```
1   atggaagattcgatggacatggacatgagcccccctgaggccccagaactatcttttcggt   60
61  tgtgaactaaaggccgacaaagattatcactttaaggtggataatgatgaaaatgagcac   120
121 cagttatctttaagaacggtcagtttaggggctggtgcaaaggatgagttgcacattgtt   180
181 gaagcagaggcaatgaattacgaaggcagtccaattaaagtaacactggcaactttgaaa   240
```

-continued

```
241   atgtctgtacagccaacggtttcccttgggggctttgaaataacaccaccagtggtctta   300

301   aggttgaagtgtggttcagggccagtgcatattagtggacagcacttagtagtgtaccgc   360

361   cggaagcaccaggagctgcaagccatgcagatggagctgcagagccctgagtacaagctg   420

421   agcaagctccgcacctcgaccatcatgaccgactacaaccccaactactgctttgctggc   480

481   aagacctcctccatcagtgacctgaaggaggtgccgcggaaaaacatcaccctcattcgg   540

541   ggtctgggccatggcgcctttggggaggtgtatgaaggccaggtgtccggaatgcccaac   600

601   gacccaagcccccctgcaagtggctgtgaagacgctgcctgaagtgtgctctgaacaggac   660

661   gaactggatttcctcatggaagccctgatcatcagcaaattcaaccaccagaacattgtt   720

721   cgctgcattggggtgagcctgcaatccctgccccggttcatcctgctggagctcatggcg   780

781   gggggagacctcaagtccttcctccgagagacccgccctcgcccgagccagccctcctcc   840

841   ctggccatgctggaccttctgcacgtggctcgggacattgcctgtggctgtcagtatttg   900

901   gaggaaaaccacttcatccaccgagacattgctgccagaaactgcctcttgacctgtcca   960

961   ggccctggaagagtggccaagattggagacttcgggatggcccgagacatctacagggcg  1020

1021  agctactatagaaagggaggctgtgccatgctgccagttaagtggatgcccccagaggcc  1080

1081  ttcatggaaggaatattcacttctaaaacagacacatggtcctttggagtgctgctatgg  1140

1141  gaaatcttttctcttggatatatgccataccccagcaaaagcaaccaggaagttctggag  1200

1201  tttgtcaccagtggaggccggatggacccacccaagaactgccctgggcctgtataccgg  1260

1261  ataatgactcagtgctggcaacatcagcctgaagacaggcccaactttgccatcattttg  1320

1321  gagaggattgaatactgcacccaggacccggatgtaatcaacaccgctttgccgatagaa  1380

1381  tatggtccacttgtggaagaggaagagaaagtgcctgtgaggcccaaggaccctgagggg  1440

1441  gttcctcctctcctggtctctcaacaggcaaaacgggaggaggagcgcagcccagctgcc  1500

1501  ccaccacctctgcctaccacctcctctggcaaggctgcaaagaaacccacagctgcagag  1560

1561  gtctctgttcgagtccctagagggccggccgtggaaggggacacgtgaatatggcattc  1620

1621  tctcagtccaaccctccttcggagttgcacaaggtccacggatccagaaacaagcccacc  1680

1681  agcttgtggaacccaacgtacggctcctggtttacagagaaacccaccaaaaagaataat  1740

1741  cctatagcaaagaaggagccacacgacaggggtaacctggggctggagggaagctgtact  1800

1801  gtcccacctaacgttgcaactgggagacttccgggggcctcactgctcctagagccctct  1860

1861  tcgctgactgccaatatgaaggaggtacctctgttcaggctacgtcacttcccttgtggg  1920

1921  aatgtcaattacggctaccagcaacagggcttgcccttagaagccgctactgcccctgga  1980

1981  gctggtcattacgaggataccattctgaaaagcaagaatagcatgaaccagcctgggccc  2040

2041  tga                                                           2043
```

ALK Immunogenic Polypeptides

The present invention features the identification of ALK antigens and immunogenic polypeptides (immunogens) with the ability to generate an immune response so as to treat a disease and its symptoms, either prophylactically or therapeutically, caused by oncogenic ALK gene fusions, rearrangements, duplications or mutations (e.g., ALK-positive cancers) following administration and delivery to a susceptible subject. It will also be appreciated that the isolated ALK antigen proteins as described herein and used as immunogens elicit an immune response, e.g., producing T-lymphocytes, in a subject. The ALK antigens and immunogens of the invention may be incorporated into a pharmaceutical composition, immunogenic composition, or vaccine as provided herein.

In some embodiments, the isolated ALK antigen protein elicits a protective immune response against at least one, more than one, or all types of ALK-positive cancers.

In some embodiments, the disease caused by oncogenic ALK gene fusions, rearrangements, duplications or mutations is an ALK-positive cancer. Nonlimiting examples of ALK-positive cancers include non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, melanoma, or a combination thereof. In some embodiments, the ALK-positive cancer is non-small cell lung cancer (NSCLC). In some embodiments, the ALK-positive cancer is anaplastic large cell lymphoma (ALCL).

ALK Antigens and Immunogens

The present invention provides herein ALK antigens and immunogens capable of generating an immune response against one or more diseases caused by oncogenic ALK gene fusions, rearrangements, duplications or mutations (e.g., ALK-positive cancers). An ALK antigen or immunogen as described herein is a polypeptide, peptide, or antibody-binding portion thereof. In some embodiments, the ALK antigen or immunogen is a protein or fragment thereof having an amino acid sequence that is at least 85%, at least 90%, at least 95%, at least 98%, at least 99%, or 100% identical to an anaplastic lymphoma kinase (ALK) capable of inducing an immune response in an immunized subject. In some embodiments, the ALK antigen or immunogen is at least 85%, at least 90%, at least 95%, at least 98%, at least 99%, or 100% identical to the ALK protein in *Homo Sapiens*. In some embodiments, the ALK antigen or immunogen is at least 85%, at least 90%, at least 95%, at least 98%, at least 99%, or 100% identical to the full-length amino acid sequence from *Homo Sapiens* as provided below (ALK cytoplasmic portion in bold font):

(SEQ ID NO: 6)

TASSGGMGAIGLLWLLPLLLSTAAVGSGMGTGQRAGSPAAGPPLQPREP

LSYSRLQRKSLAVDEVVPSLFRVYARDLLLPPSSSELKAGRPEARGSLA

LDCAPLLRLLGPAPGVSWTAGSPAPAEARTLSRVLKGGSVRKLRRAKQL

VLELGEEAILEGCVGPPGEAAVGLLQFNLSELFSWWIRQGEGRLRIRLM

PEKKASEVGREGRLSAAIRASQPRLLFQIFGTGHSSLESPTNMPSPSPD

YFTWNLTWIMKDSFPFLSHRSRYGLECSFDFPCELEYSPPLHDLRNQSW

SWRRIPSEEASQMDLLDGPGAERSKEMPRGSFLLLNTSADSKHTILSPW

MRSSSEHCTLAVSVHRHLQPSGRYIAQLLPHNEAAREILLMPTPGKHGW

TVLQGRIGRPDNPFRVALEYISSGNRSLSAVDFFALKNCSEGTSPGSKM

ALQSSFTCWNGTVLQLGQACDFHQDCAQGEDESQMCRKLPVGFYCNFED

GFCGWTQGTLSPHTPQWQVRTLKDARFQDHQDHALLLSTTDVPASESAT

-continued

VTSATFPAPIKSSPCELRMSWLIRGVLRGNVSLVLVENKTGKEQGRMVW

HVAAYEGLSLWQWMVLPLLDVSDRFWLQMVAWWGQGSRAIVAFDNISIS

LDCYLTISGEDKILQNTAPKSRNLFERNPNKELKPGENSPRQTPIFDPT

VHWLFTTCGASGPHGPTQAQCNNAYQNSNLSVEVGSEGPLKGIQIWKVP

ATDTYSISGYGAAGGKGGKNTMMRSHGVSVLGIFNLEKDDMLYILVGQQ

GEDACPSTNQLIQKVCIGENNVIEEEIRVNRSVHEWAGGGGGGGATYV

FKMKDGVPVPLIIAAGGGGRAYGAKTDTFHPERLENNSSVLGLNGNSGA

AGGGGGWNDNTSLLWAGKSLQEGATGGHSCPQAMKKWGWETRGGFGGGG

GGCSSGGGGGGYIGGNAASNNDPEMDGEDGVSFISPLGILYTPALKVME

GHGEVNIKHYLNCSHCEVDECHMDPESHKVICFCDHGTVLAEDGVSCIV

SPTPEPHLPLSLILSVVTSALVAALVLAFSGIMIVYRRKHQELQAMQME

LQSPEYKLSKLRTSTIMTDYNPNYCFAGKTSSISDLKEVPRKNITLIRG

LGHGAFGEVYEGQVSGMPNDPSPLQVAVKTLPEVCSEQDELDFLMEALI

ISKFNHQNIVRCIGVSLQSLPRFILLELMAGGDLKSFLRETRPRPSQPS

SLAMLDLLHVARDIACGCQYLEENHFIHRDIAARNCLLTCPGPGRVAKI

GDFGMARDIYRASYYRKGGCAMLPVKWMPPEAFMEGIFTSKTDTWSFGV

LLWEIFSLGYMPYPSKSNQEVLEFVTSGGRMDPPKNCPGPVYRIMTQCW

QHQPEDRPNFAIILERIEYCTQDPDVINTALPIEYGPLVEEEEKVPVRP

KDPEGVPPLLVSQQAKREEERSPAAPPPLPTTSSGKAAKKPTAAEISVR

VPRGPAVEGGHVNMAFSQSNPPSELHKVHGSRNKPTSLWNPTYGSWFTE

KPTKKNNPIAKKEPHDRGNLGLEGSCTVPPNVATGRLPGASLLLEPSSL

TANMKEVPLFRLRHFPCGNVNYGYQQQGLPLEAATAPGAGHYEDTILKS

KNSMNQPGP

In some embodiments, the ALK antigen or immunogen is at least 85%, at least 90%, at least 95%, at least 98%, at least 99%, or 100% identical to the full-length ALK amino acid sequence from *Homo Sapiens* as provided below:

(SEQ ID NOS: 7 and 75-89, respectively, in order of appearance)

G A A A V V A A G T S R R L C S E G R G

A P R C F P A A L W S A T Q S R G R * *

W V R R G R Q D F G R P C P E R P Q L L

P P G P L Q C L R T L R S R G A G E S K

D A A N L R S A G A G I H A Q K F S R Q

T V R S L P A A E R * L E G A Q D G S L

R P R F P P R P G R R A W R S Q K E R K

R R P G Q R A A A G S R R S Q P * K L Q

R L E A A P R G D R P Q L R L R G A G E

D G T Q L P P P F N H S S S S V P S A A

S Y R R G R G T R R G E R E A Q G P S Q

* A Q C A * V S L D S P L S F Q V C F I

* T P A R L R A V G G K Q E T C A H A Q

-continued

S S G D Q V E G A A G Y Q G L F R A S S

H L G E S E G * G W A R R A V * T A S S

G G M G A I G L L W L L P L L L S T A A

V G S G M G T G Q R A G S P A A G P P L

Q P R E P L S Y S R L Q R K S L A V D F

V V P S L F R V Y A R D L L L P P S S S

E L K A G R P E A R G S L A L D C A P L

L R L L G P A P G V S W T A G S P A P A

E A R T L S R V L K G G S V R K L R R A

K Q L V L E L G E E A I L E G C V G P P

G E A A V G L L Q F N L S E L F S W W I

R Q G E G R L R I R L M P E K K A S E V

G R E G R L S A A I R A S Q P R L L F Q

I F G T G H S S L E S P T N M P S P S P

D Y F T W N L T W I M K D S F P F L S H

R S R Y G L E C S F D F P C E L E Y S P

P L H D L R N Q S W S W R R I P S E E A

S Q M D L L D G P G A E R S K E M P R G

S F L L L N T S A D S K H T I L S P W M

R S S S E H C T L A V S V H R H L Q P S

G R Y I A Q L L P H N E A A R E I L L M

P T P G K H G W T V L Q G R I G R P D N

P F R V A L E Y I S S G N R S L S A V D

F F A L K N C S E G T S P G S K M A L Q

S S F T C W N G T V L Q L G Q A C D F H

Q D C A Q G E D E S Q M C R K L P V G F

Y C N F E D G F C G W T Q G T L S P H T

P Q W Q V R T L K D A R F Q D H Q D H A

L L L S T T D V P A S E S A T V T S A T

F P A P I K S S P C E L R M S W L I R G

V L R G N V S L V L V E N K T G K E Q G

R M V W H V A A Y E G L S L W Q W M V L

P L L D V S D R F W L Q M V A W W G Q G

S R A I V A F D N I S I S L D C Y L T I

S G E D K I L Q N T A P K S R N L F E R

N P N K E L K P G E N S P R Q T P I F D

P T V H W L F T T C G A S G P H G P T Q

A Q C N N A Y Q N S N L S V E V G S E G

P L K G I Q I W K V P A T D T Y S I S G

Y G A A G G K G G K N T M M R S H G V S

-continued

V L G I F N L E K D D M L Y I L V G Q Q

G E D A C P S T N Q L I Q K V C I G E N

N V I E E E I R V N R S V H E W A G G G

G G G G G A T Y V F K M K D G V P V P L

I I A A G G G R A Y G A K T D T F H P

E R L E N N S S V L G L N G N S G A A G

G G G G W N D N T S L L W A G K S L Q E

G A T G G H S C P Q A M K K W G W E T R

G G F G G G G G C S S G G G G G G Y I

G G N A A S N N D P E M D G E D G V S F

I S P L G I L Y T P A L K V M E G H G E

V N I K H Y L N C S H C E V D E C H M D

P E S H K V I C F C D H G T V L A E D G

V S C I V S P T P E P H L P L S L I L S

V V T S A L V A A L V L A F S G I M I V

Y R R K H Q E L Q A M Q M E L Q S P E Y

K L S K L R T S T I M T D Y N P N Y C F

A G K T S S I S D L K E V P R K N I T L

I R G L G H G A F G E V Y E G Q V S G M

P N D P S P L Q V A V K T L P E V C S E

Q D E L D F L M E A L I I S K F N H Q N

I V R C I G V S L Q S L P R F I L L E L

M A G G D L K S F L R E T R P R P S Q P

S S L A M L D L L H V A R D I A C G C Q

Y L E E N H F I H R D I A A R N C L L T

C P G P G R V A K I G D F G M A R D I Y

R A S Y Y R K G G C A M L P V K W M P P

E A F M E G I F T S K T D T W S F G V L

L W E I F S L G Y M P Y P S K S N Q E V

L E F V T S G G R M D P P K N C P G P V

Y R I M T Q C W Q H Q P E D R P N F A I

I L E R I E Y C T Q D P D V I N T A L P

I E Y G P L V E E E E K V P V R P K D P

E G V P P L L V S Q Q A K R E E E R S P

A A P P P L P T T S S G K A A K K P T A

A E I S V R V P R G P A V E G G H V N M

A F S Q S N P P S E L H K V H G S R N K

P T S L W N P T Y G S W F T E K P T K K

N N P I A K K E P H D R G N L G L E G S

C T V P P N V A T G R L P G A S L L L E

P S S L T A N M K E V P L F R L R H F P

-continued

C G N V N Y G Y Q Q Q G L P L E A A T A

P G A G H Y E D T I L K S K N S M N Q P

G P * A R S H T H F S S L G S L R P W R

R E R Q W L L H K P E T K C H V L F C A

N L F * S T T K K A V F * K C F R K V L

S M G S S Y S F E R R K Y H K N E * * I

Q G P D V V A * G F Y A C L L Y T S L C

F F Q I V C A L L Q C S Q N * L L L C F

I V G V I D V S L P C * C G H E P F E G

R G N G N K G V I C N D *.

In some embodiments, ALK antigen or immunogen amino acid sequence comprises an amino acid sequence that is at least 95%, at least 98%, at least 99%, or 100% identical to a sequence provided in Table 3, Table 4, or Table 5. In some embodiments, the ALK antigen or immunogen comprises an amino acid sequence that is at least 95%, at least 98%, at least 99%, or 100% identical to: RPRPSQPSSL (SEQ ID NO: 2). In some embodiments, the ALK antigen or immunogen comprises an amino acid sequence that is at least 95%, at least 98%, at least 99%, or 100% identical to: IVRCIGVSL (SEQ ID NO: 3). In some embodiments, the ALK antigen or immunogen comprises an amino acid sequence that is at least 95%, at least 98%, at least 99%, or 100% identical to: VPRKNITLI (SEQ ID NO: 4). In some embodiments, the ALK antigen or immunogen comprises an amino acid sequence that is at least 95%, at least 98%, at least 99%, or 100% identical to: TAAEVSVRV (SEQ ID NO: 5). In some embodiments, the ALK antigen or immunogen comprises an amino acid sequence that is at least 95%, at least 98%, at least 99%, or 100% identical to: AMLDLLHVA (SEQ ID NO: 1).

Figure 6A:
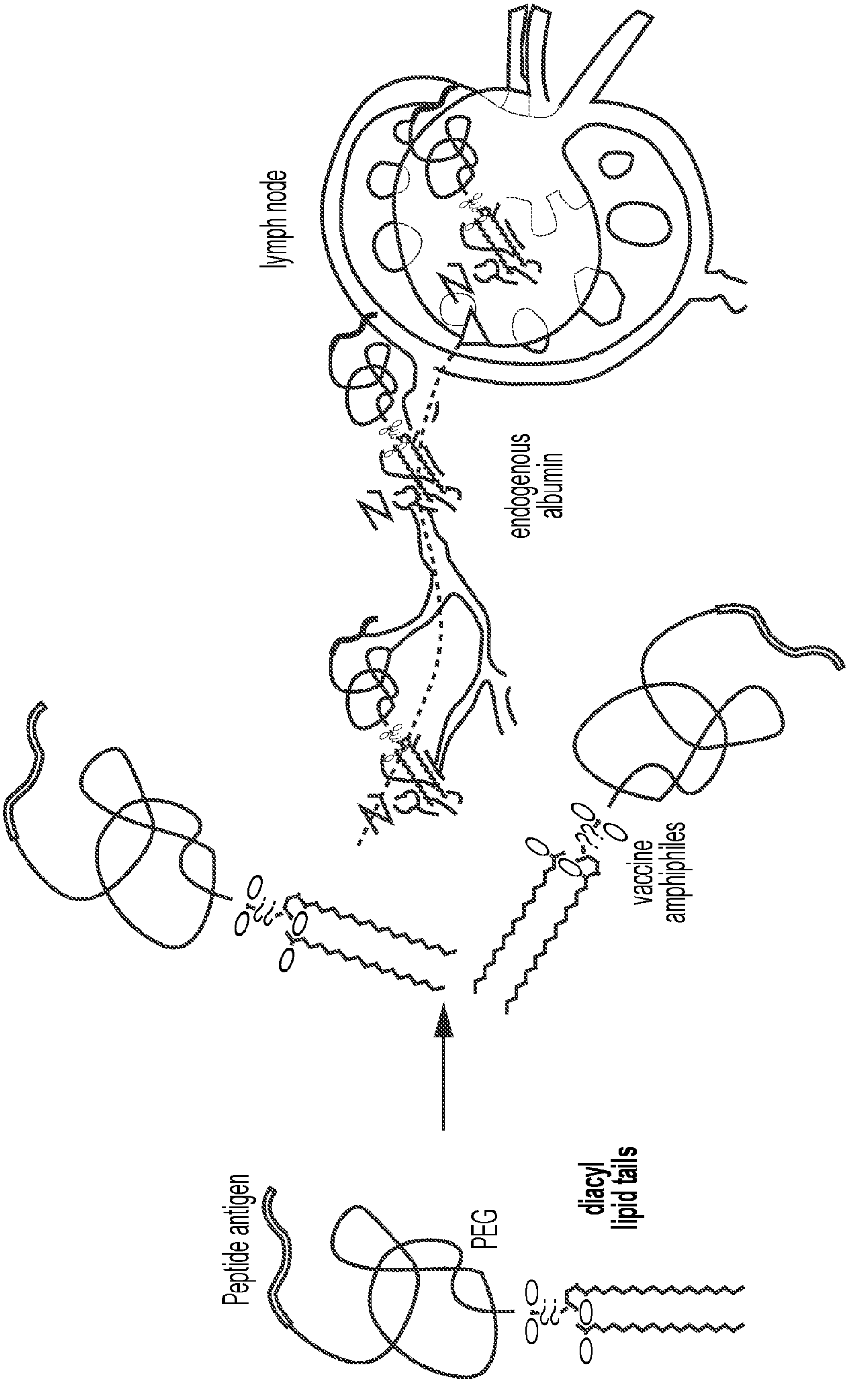
FIGS. 6A-6C depict amphiphile vaccines eliciting protective T-cell responses in mice.

In some embodiments, the ALK antigen or immunogen is conjugated to an amphiphile or amphiphilic tail (see, e.g., FIG. 6A). In some embodiments, the amphiphile is N-hydroxy succinimidyl ester-end-functionalized poly(ethylene glycol)-lipid (NHS-PEG2KDa-DSPE). ALK amph-peptides may significantly increase T-cell expansion and greatly enhance anti-tumor efficacy (see Example 2). ALK amph-peptides may be generated as taught in H. Liu et al., Structure-based programming of lymph-node targeting in molecular vaccines. Nature 507, 5199522 (2014), which is incorporated herein in its entirety.

In some embodiments, the ALK antigen or immunogen conjugated to an amphiphile or amphiphilic tail comprises an amino acid sequence from Table 3. In some embodiments, the ALK antigen or immunogen conjugated to an amphiphile or amphiphilic tail comprises an amino acid sequence from Table 4. In some embodiments, the ALK antigen or immunogen conjugated to an amphiphile or amphiphilic tail comprises an amino acid sequence from Table 5. In some embodiments, the ALK antigen or immunogen conjugated to an amphiphile or amphiphilic tail comprises flanking amino acid sequences. In some embodiments, the flanking amino acid sequences are on either side or on both sides of the ALK antigen or immunogen sequence. In some embodiments, the ALK antigen or immunogen conjugated to an amphiphile or amphiphilic tail comprises a central core amino acid sequence with flanking amino acid sequences on both sides of the core. In some embodiments, the core amino acid sequence is about 9 to 10 amino acids in length. In some embodiments, the flanking amino acid sequences are between 5 to 15 amino acids. In some embodiments, the ALK antigen or immunogen conjugated to an amphiphile or amphiphilic tail comprises an amino acid sequence that is about 9 to about 30 amino acids in length. In some embodiments, the ALK antigen or immunogen conjugated to an amphiphile or amphiphilic tail comprises an amino acid sequence from Table 3 with flanking amino acid sequences.

In some embodiments, the ALK antigen or immunogen is a polynucleotide sequence. In some embodiments, the ALK antigen or immunogen is a polynucleotide sequence that encodes a polypeptide or peptide antigen or fragment thereof as described herein. In some embodiments, the nucleic acid molecule encoding an ALK polypeptide or fragment thereof (antigen or antigen protein or immunogen) is at least 85%, at least 90%, at least 95%, at least 98%, at least 99%, or 100% identical to the full-length ALK nucleic acid sequence from *Homo Sapiens* provided below:

(SEQ ID NO: 9)

2 ggggcggcagcggtggtagcagctggtacctcccgccgcctctgttcggagggtcgcggg 61

62 gcaccgaggtgctttccggccgccctctggtcggccacccaaagccgcgggcgctgatga 121

122 tgggtgaggagggggcggcaagatttcgggcgcccctgccctgaacgccctcagctgctg 181

182 ccgccggggccgctccagtgcctgcgaactctgaggagccgaggcgccggtgagagcaag 241

242 gacgctgcaaacttgcgcagcgcgggggctgggattcacgcccagaagttcagcaggcag 301

302 acagtccgaagccttcccgcagcggagagatagcttgagggtgcgcaagacggcagcctc 361

362 cgccctcggttcccgcccagaccgggcagaagagcttggaggagccaaaaggaacgcaaa 421

-continued

```
 422  aggcggccaggacagcgtgcagcagctgggagccgccgttctcagccttaaaagttgcag   481
 482  agattggaggctgccccgagaggggacagaccccagctccgactgcggggggcaggagag   541
 542  gacggtacccaactgccacctcccttcaaccatagtagttcctctgtaccgagcgcagcg   601
 602  agctacagacgggggcgcggcactcggcgcggagagcgggaggctcaaggtcccagccag   661
 662  tgagcccagtgtgcttgagtgtctctggactcgcccctgagcttccaggtctgtttcatt   721
 722  tagactcctgctcgcctccgtgcagttgggggaaagcaagagacttgcgcgcacgcacag   781
 782  tcctctggagatcaggtggaaggagccgctgggtaccaaggactgttcagagcctcttcc   841
 842  catctcggggagagcgaagggtgaggctgggcccggagagcagtgtaaacggcctcctcc   901
 902  ggcgggatgggagccatcgggctcctgtggctcctgccgctgctgctttccacggcagct   961
 962  gtgggctccgggatggggaccggccagcgcgcgggctccccagctgcggggccgccgctg  1021
1022  cagccccgggagccactcagctactcgcgcctgcagaggaagagtctggcagttgacttc  1081
1082  gtggtgccctcgctcttccgtgtctacgcccgggacctactgctgccaccatcctcctcg  1141
1142  gagctgaaggctggcaggcccgaggcccgcggctcgctagctctggactgcgccccgctg  1201
1202  ctcaggttgctggggccggcgccgggggtctcctggaccgccggttcaccagccccggca  1261
1262  gaggcccggacgctgtccagggtgctgaagggcggctccgtgcgcaagctccggcgtgcc  1321
1322  aagcagttggtgctggagctgggcgaggaggcgatcttggagggttgcgtcgggcccccc  1381
1382  ggggaggcggctgtggggctgctccagttcaatctcagcgagctgttcagttggtggatt  1441
1442  cgccaaggcgaagggcgactgaggatccgcctgatgcccgagaagaaggcgtcggaagtg  1501
1502  ggcagagagggaaggctgtccgcggcaattcgcgcctcccagccccgccttctcttccag  1561
1562  atcttcgggactggtcatagctccttggaatcaccaacaaacatgccttctccttctcct  1621
1622  gattattttacatggaatctcacctggataatgaaagactccttccctttcctgtctcat  1681
1682  cgcagccgatatggtctggagtgcagctttgacttcccctgtgagctggagtattcccct  1741
1742  ccactgcatgacctcaggaaccagagctggtcctggcgccgcatcccctccgaggaggcc  1801
1802  tcccagatggacttgctggatgggcctggggcagagcgttctaaggagatgcccagaggc  1861
1862  tcctttctccttctcaacacctcagctgactccaagcacaccatcctgagtccgtggatg  1921
1922  aggagcagcagtgagcactgcacactggccgtctcggtgcacaggcacctgcagccctct  1981
1982  ggaaggtacattgcccagctgctgccccacaacgaggctgcaagagagatcctcctgatg  2041
2042  cccactccagggaagcatggttggacagtgctccagggaagaatcgggcgtccagacaac  2101
2102  ccatttcgagtggccctggaatacatctccagtggaaaccgcagcttgtctgcagtggac  2161
2162  ttctttgccctgaagaactgcagtgaaggaacatccccaggctccaagatggccctgcag  2221
2222  agctccttcacttgttggaatgggacagtcctccagcttgggcaggcctgtgacttccac  2281
2282  caggactgtgcccagggagaagatgagagccagatgtgccggaaactgcctgtgggtttt  2341
2342  tactgcaactttgaagatggcttctgtggctggacccaaggcacactgtcaccccacact  2401
2402  cctcaatggcaggtcaggaccctaaaggatgcccggttccaggaccaccaagaccatgct  2461
2462  ctattgctcagtaccactgatgtccccgcttctgaaagtgctacagtgaccagtgctacg  2521
2522  tttcctgcaccgatcaagagctctccatgtgagctccgaatgtcctggctcattcgtgga  2581
2582  gtcttgaggggaaacgtgtccttggtgctagtggagaacaaaaccgggaaggagcaaggc  2641
2642  aggatggtctggcatgtcgccgcctatgaaggcttgagcctgtggcagtggatggtgttg  2701
2702  cctctcctcgatgtgtctgacaggttctggctgcagatggtcgcatggtggggacaagga  2761
2762  tccagagccatcgtggcttttgacaatatctccatcagcctggactgctacctcaccatt  2821
```

-continued 2822 agcggagaggacaagatcctgcagaatacagcacccaaatcaagaaacctgtttgagaga 2881

2882 aacccaaacaaggagctgaaacccggggaaaattcaccaagacagacccccatctttgac 2941

2942 cctacagttcattggctgttcaccacatgtggggccagcgggccccatggccccacccag 3001

3002 gcacagtgcaacaacgcctaccagaactccaacctgagcgtggaggtggggagcgagggc 3061

3062 cccctgaaaggcatccagatctggaaggtgccagccaccgacacctacagcatctcgggc 3121

3122 tacggagctgctggcgggaaaggcgggaagaacaccatgatgcggtcccacggcgtgtct 3181

3182 gtgctgggcatcttcaacctggagaaggatgacatgctgtacatcctggttgggcagcag 3241

3242 ggagaggacgcctgccccagtacaaaccagttaatccagaaagtctgcattggagagaac 3301

3302 aatgtgatagaagaagaaatccgtgtgaacagaagcgtgcatgagtgggcaggaggcgga 3361

3362 ggaggagggggtggagccacctacgtatttaagatgaaggatggagtgccggtgcccctg 3421

3422 atcattgcagccggaggtggtggcagggcctacggggccaagacagacacgttccaccca 3481

3482 gagagactggagaataactcctcggttctagggctaaacggcaattccggagccgcaggt 3541

3542 ggtggaggtggctggaatgataacacttccttgctctgggccggaaaatctttgcaggag 3601

3602 ggtgccaccggaggacattcctgcccccaggccatgaagaagtgggggtgggagacaaga 3661

3662 gggggtttcggaggggggtggagggggggtgctcctcaggtggaggaggcggaggatatata 3721

3722 ggcggcaatgcagcctcaaacaatgaccccgaaatggatggggaagatggggtttccttc 3781

3782 atcagtccactgggcatcctgtacaccccagctttaaaagtgatggaaggccacggggaa 3841

3842 gtgaatattaagcattatctaaactgcagtcactgtgaggtagacgaatgtcacatggac 3901

3902 cctgaaagccacaaggtcatctgcttctgtgaccacgggacggtgctggctgaggatggc 3961

3962 gtctcctgcattgtgtcacccaccccggagccacacctgccactctcgctgatcctctct 4021

4022 gtggtgacctctgccctcgtggccgccctggtcctggctttctccggcatcatgattgtg 4081

4082 taccgccggaagcaccaggagctgcaagccatgcagatggagctgcagagccctgagtac 4141

4142 aagctgagcaagctccgcacctcgaccateatgaccgactacaaccccaactactgcttt 4201

4202 gctggcaagacctcctccatcagtgacctgaaggaggtgccgcggaaaaacatcaccctc 4261

4262 attcggggtctgggccatggcgcctttggggaggtgtatgaaggccaggtgtccggaatg 4321

4322 cccaacgacccaagcccccctgcaagtggctgtgaagacgctgcctgaagtgtgctctgaa 4381

4382 caggacgaactggatttcctcatggaagccctgatcatcagcaaattcaaccaccagaac 4441

4442 attgttcgctgcattggggtgagcctgcaatccctgccccggttcatcctgctggagctc 4501

4502 atggcgggggggagacctcaagtccttcctccgagagacccgccctcgcccgagccagccc 4561

4562 tcctccctggccatgctggaccttctgcacgtggctcgggacattgcctgtggctgtcag 4621

4622 tatttggaggaaaaccacttcatccaccgagacattgctgccagaaactgcctcttgacc 4681

4682 tgtccaggccctggaagagtggccaagattggagacttcgggatggcccgagacatctac 4741

4742 agggcgagctactatagaaagggaggctgtgccatgctgccagttaagtggatgcccccca 4801

4802 gaggccttcatggaaggaatattcacttctaaaacagacacatggtcctttggagtgctg 4861

4862 ctatgggaaatcttttctcttggatatatgccataccccagcaaaagcaaccaggaagtt 4921

4922 ctggagtttgtcaccagtggaggccggatggacccacccaagaactgccctgggcctgta 4981

4982 taccggataatgactcagtgctggcaacatcagcctgaagacaggcccaactttgccatc 5041

5042 atttggagaggattgaatactgcacccaggacccggatgtaatcaacaccgctttgccg 5101

5102 atagaatatggtccacttgtggaagaggaagagaaagtgcctgtgaggcccaaggaccct 5161

5162 gagggggttcctcctctcctggtctctcaacaggcaaaacgggaggaggagcgcagccca 5221

5222 gctgccccaccacctctgcctaccacctcctctggcaaggctgcaaagaaacccacagct 5281

-continued

```
5282  gcagagatctctgttcgagtccctagagggccggccgtggaaggggacacgtgaatatg  5341

5342  gcattctctcagtccaaccctccttcggagttgcacaaggtccacggatccagaaacaag  5401

5402  cccaccagcttgtggaacccaacgtacggctcctggtttacagagaaacccaccaaaaag  5461

5462  aataatcctatagcaaagaaggagccacacgacaggggtaacctggggctggagggaagc  5521

5522  tgtactgtcccacctaacgttgcaactgggagacttccgggggcctcactgctcctagag  5581

5582  ccctcttcgctgactgccaatatgaaggaggtacctctgttcaggctacgtcacttccct  5641

5642  tgtgggaatgtcaattacggctaccagcaacagggcttgcccttagaagccgctactgcc  5701

5702  cctggagctggtcattacgaggataccattctgaaaagcaagaatagcatgaaccagcct  5761

5762  gggccctgagctcggtcgcacactcacttctcttccttgggatccctaagaccgtggagg  5821

5822  agagagaggcaatggctccttcacaaaccagagaccaaatgtcacgttttgttttgtgcc  5881

5882  aacctattttgaagtaccaccaaaaaagctgtattttgaaaatgctttagaaaggttttg  5941

5942  agcatgggttcatcctattctttcgaaagaagaaaatatcataaaaatgagtgataaata  6001

6002  caaggcccagatgtggttgcataaggtttttatgcatgtttgttgtatacttccttatgc  6061

6062  ttctttcaaattgtgtgtgctctgcttcaatgtagtcagaattagctgcttctatgtttc  6121

6122  atagttggggtcatagatgtttccttgccttgttgatgtggacatgagccatttgagggg  6181

6182  agagggaacggaaataaaggagttatttgtaatgactaaaa                     6222
```

In some embodiments, ALK polynucleotide sequences encode ALK antigen or immunogen amino acid sequences that are at least 95%, at least 98%, at least 99%, or 100% identical to the sequences provided in Table 3, Table 4, and Table 5. In some embodiments, the ALK polynucleotide sequence encodes the ALK antigen or immunogen amino acid sequence that is at least 95%, at least 98%, at least 99%, or 100% identical to: RPRPSQPSSL (SEQ ID NO: 2). In some embodiments, the ALK polynucleotide sequence encodes the ALK antigen or immunogen amino acid sequence that is at least 95%, at least 98%, at least 99%, or 100% identical to: IVRCIGVSL (SEQ ID NO: 3). In some embodiments, the ALK polynucleotide sequence encodes the ALK antigen or immunogen amino acid sequence that is at least 95%, at least 98%, at least 99%, or 100% identical to: VPRKNITLI (SEQ ID NO: 4). In some embodiments, the ALK polynucleotide sequence encodes the ALK antigen or immunogen amino acid sequence that is at least 95%, at least 98%, at least 99%, or 100% identical to: TAAEVSVRV (SEQ ID NO: 5). In some embodiments, the ALK polynucleotide sequence encodes the ALK antigen or immunogen amino acid sequence that is at least 95%, at least 98%, at least 99%, or 100% identical to: AMLDLLHVA (SEQ ID NO: 1).

In some embodiments, the amino acid sequence of the antigen or immunogen, e.g., the ALK protein, is reverse translated and optimized for expression in mammalian cells. As will be appreciated by a skilled practitioner in the art, optimization of the nucleic acid sequence includes optimization of the codons for expression of a sequence in mammalian cells and RNA optimization (such as RNA stability).

In some embodiments, the ALK antigen or immunogen is isolated and/or purified. In some embodiments, the antigen or immunogen is formulated for administration to a subject in need. In some embodiments, the antigen or immunogen is administered to a subject in need thereof in an effective amount to elicit an immune response (e.g., a T-cell response) in the subject. In some embodiments, the immune response produces T-lymphocytes. In some embodiments, the immune response is prophylactic or therapeutic.

In some embodiments, fusion proteins comprising the ALK antigen polypeptides are described herein. In some embodiments, the ALK polypeptide can be fused to any heterologous amino acid sequence to form the fusion protein. By way of example, peptide components of ALK polypeptides may be generated independently and then fused together to produce an intact ALK polypeptide antigen, for use as an immunogen.

ALK Immunogenic Compositions and Vaccines

The ALK antigens or immunogens may be used in immunogenic compositions or vaccines to elicit an immune response, e.g., a T-cell response, against disease caused by oncogenic ALK gene fusions, rearrangements, duplications or mutations (e.g., ALK-positive cancers). In some embodiments, the immune response includes producing T-lymphocytes.

In particular embodiments, the ALK polypeptides of the immunogenic compositions or vaccines contain antigenic determinants that serve to elicit an immune response in a subject (e.g., the production of activated T-cells) that can treat and/or protect a subject against disease caused by oncogenic ALK gene fusions, rearrangements, duplications or mutations (e.g., ALK-positive cancers) and symptoms thereof.

In some embodiments, such immunogenic compositions or vaccines as described herein contain at least one ALK antigen or immunogen and are effective in treating, reducing, delaying, or preventing at least one disease caused by oncogenic ALK gene fusions, rearrangements, duplications or mutations (e.g., ALK-positive cancers). In some embodiments, such immunogenic compositions or vaccines as described herein contain two or more ALK antigens or immunogens and are effective in treating, reducing, or preventing at least one disease caused by oncogenic ALK gene fusions, rearrangements, duplications or mutations (e.g., ALK-positive cancers). In some embodiments, the two or more ALK antigens or immunogens comprise two or more amino acid sequences selected from the following: AMLDLLHVA (SEQ ID NO: 1); RPRPSQPSSL (SEQ ID NO: 2); IVRCIGVSL (SEQ ID NO: 3); VPRKNITLI (SEQ ID NO: 4); and/or TAAEVSVRV (SEQ ID NO: 5). In some embodiments, the two or more ALK antigens or immunogens comprise two or more amino acid sequences selected from Table 3, Table 4 and/or Table 5. In some embodiments, the immunogenic compositions or vaccines contain at least one ALK antigen or immunogen conjugated to an amphiphile or amphiphilic tail (see, e.g. FIG. 6A). In some embodiments, at least one of the two or more ALK antigens or immunogens in an immunogenic composition or vaccine is conjugated to an amphiphile or amphiphilic tail. In some embodiments, the amphiphile is N-hydroxy succinimidyl ester-end-functionalized poly(ethylene glycol)-lipid (NHS-PEG2KDa-DSPE). In some embodiments, the two or more ALK antigens or immunogens are provided in equal concentration ratios in an immunogenic composition or vaccine.

Because the ALK antigens or immunogens and the sequences thereof as described herein and used as immunogenic compositions or vaccines, elicit an immune response in an immunocompetent subject, they provide a superior vaccine against which an immune response (e.g., producing T-lymphocytes) is generated.

In some embodiments, an immunogenic composition or a vaccine is provided that elicits an immune response (e.g., producing T-lymphocytes) in a subject following introduction, administration, or delivery of the antigen or immunogen to the subject. The route of introduction, administration, or delivery is not limited and may include, for example, intravenous, subcutaneous, intramuscular, oral, or other routes. The immunogenic composition or vaccine may be therapeutic (e.g., administered to a subject following a symptom of disease caused by oncogenic ALK gene fusions, rearrangements, duplications or mutations (e.g., ALK-positive cancers)) or prophylactic (e.g., administered to a subject prior to the subject having or expressing a symptom of disease, or full-blown disease, caused by oncogenic ALK gene fusions, rearrangements, duplications or mutations (e.g., ALK-positive cancers)).

Vectors

Vectors containing a nucleotide sequence encoding an isolated ALK polypeptide or peptide antigen are provided. In some embodiments, the vectors comprise a nucleotide sequence encoding the full-length ALK polypeptide or peptide antigen that is at least 85%, at least 90%, at least 95%, at least 96%, at least 97%, at least 98%, at least 99%, or 100% identical to a *Homo Sapiens* full-length ALK polypeptide as provided herein. In some embodiments, the vectors comprise a nucleotide sequence encoding the ALK polypeptide or peptide antigen that is at least 95%, at least 96%, at least 97%, at least 98%, at least 99%, or 100% identical to a polynucleotide encoding at least one ALK polypeptide sequence provided in Table 3, Table 4 or Table 5. In some embodiments, the vector further includes a promoter operably linked to the nucleotide sequence encoding the ALK polypeptide. In a particular embodiment, the promoter is a cytomegalovirus (CMV) promoter. In some embodiments, the nucleotide sequence of the vector is at least 85%, at least 90%, at least 95%, at least 98%, at least 99%, or 100% identical to the polynucleotide sequence provided below. In some embodiments, the nucleotide sequence of the vector is at least 85%, at least 90%, at least 95%, at least 98%, at least 99%, or 100% identical to the *Homo Sapiens* full-length ALK nucleic acid sequence provided below.

```
                                                        (SEQ ID NO: 9)
   2 ggggcggcagcggtggtagcagctggtacctcccgccgcctctgttcggagggtcgcggg   61

  62 gcaccgaggtgctttccggccgccctctggtcggccacccaaagccgcgggcgctgatga  121

 122 tgggtgaggagggggcggcaagatttcgggcgcccctgccctgaacgccctcagctgctg  181

 182 ccgccggggccgctccagtgcctgcgaactctgaggagccgaggcgccggtgagagcaag  241

 242 gacgctgcaaacttgcgcagcgcgggggctgggattcacgcccagaagttcagcaggcag  301

 302 acagtccgaagccttcccgcagcggagagatagcttgagggtgcgcaagacggcagcctc  361

 362 cgccctcggttcccgcccagaccgggcagaagagcttggaggagccaaaaggaacgcaaa  421

 422 aggcggccaggacagcgtgcagcagctgggagccgccgttctcagccttaaaagttgcag  481

 482 agattggaggctgccccgagaggggacagaccccagctccgactgcgggggcaggagag  541

 542 gacggtacccaactgccacctcccttcaaccatagtagttcctctgtaccgagcgcagcg  601

 602 agctacagacgggggcgcggcactcggcgcggagagcgggaggctcaaggtcccagccag  661

 662 tgagcccagtgtgcttgagtgtctctggactcgcccctgagcttccaggtctgtttcatt  721

 722 tagactcctgctcgcctccgtgcagttgggggaaagcaagagacttgcgcgcacgcacag  781

 782 tcctctggagatcaggtggaaggagccgctgggtaccaaggactgttcagagcctcttcc  841

 842 catctcggggagagcgaagggtgaggctgggcccggagagcagtgtaaacggcctcctcc  901

 902 ggcgggatgggagccatcgggctcctgtggctcctgccgctgctgctttccacggcagct  961

 962 gtgggctccgggatggggaccggccagcgcgcgggctccccagctgcggggccgccgctg 1021

1022 cagccccgggagccactcagctactcgcgcctgcagaggaagagtctggcagttgacttc 1081

1082 gtggtgccctcgctcttccgtgtctacgcccgggacctactgctgccaccatcctcctcg 1141
```

-continued

```
1142  gagctgaaggctggcaggcccgaggcccgcggctcgctagctctggactgcgccccgctg  1201
1202  ctcaggttgctggggccggcgccgggggtctcctggaccgccggttcaccagccccggca  1261
1262  gaggcccggacgctgtccagggtgctgaagggcggctccgtgcgcaagctccggcgtgcc  1321
1322  aagcagttggtgctggagctgggcgaggaggcgatcttggagggttgcgtcgggcccccc  1381
1382  ggggaggcggctgtggggctgctccagttcaatctcagcgagctgttcagttggtggatt  1441
1442  cgccaaggcgaagggcgactgaggatccgcctgatgcccgagaagaaggcgtcggaagtg  1501
1502  ggcagagagggaaggctgtccgcggcaattcgcgcctcccagccccgccttctcttccag  1561
1562  atcttcgggactggtcatagctccttggaatcaccaacaaacatgccttctccttctcct  1621
1622  gattattttacatggaatctcacctggataatgaaagactccttccctttcctgtctcat  1681
1682  cgcagccgatatggtctggagtgcagctttgacttcccctgtgagctggagtattcccct  1741
1742  ccactgcatgacctcaggaaccagagctggtcctggcgccgcatcccctccgaggaggcc  1801
1802  tcccagatggacttgctggatgggcctggggcagagcgttctaaggagatgcccagaggc  1861
1862  tcctttctccttctcaacacctcagctgactccaagcacaccatcctgagtccgtggatg  1921
1922  aggagcagcagtgagcactgcacactggccgtctcggtgcacaggcacctgcagccctct  1981
1982  ggaaggtacattgcccagctgctgccccacaacgaggctgcaagagagatcctcctgatg  2041
2042  cccactccagggaagcatggttggacagtgctccagggaagaatcgggcgtccagacaac  2101
2102  ccatttcgagtggccctggaatacatctccagtggaaaccgcagcttgtctgcagtggac  2161
2162  ttctttgccctgaagaactgcagtgaaggaacatccccaggctccaagatggccctgcag  2221
2222  agctccttcacttgttggaatgggacagtcctccagcttgggcaggcctgtgacttccac  2281
2282  caggactgtgcccagggagaagatgagagccagatgtgccggaaactgcctgtgggtttt  2341
2342  tactgcaactttgaagatggcttctgtggctggacccaaggcacactgtcaccccacact  2401
2402  cctcaatggcaggtcaggaccctaaaggatgcccggttccaggaccaccaagaccatgct  2461
2462  ctattgctcagtaccactgatgtccccgcttctgaaagtgctacagtgaccagtgctacg  2521
2522  tttcctgcaccgatcaagagctctccatgtgagctccgaatgtcctggctcattcgtgga  2581
2582  gtcttgaggggaaacgtgtccttggtgctagtggagaacaaaaccgggaaggagcaaggc  2641
2642  aggatggtctggcatgtcgccgcctatgaaggcttgagcctgtggcagtggatggtgttg  2701
2702  cctctcctcgatgtgtctgacaggttctggctgcagatggtcgcatggtggggacaagga  2761
2762  tccagagccatcgtggcttttgacaatatctccatcagcctggactgctacctcaccatt  2821
2822  agcggagaggacaagatcctgcagaatacagcacccaaatcaagaaacctgtttgagaga  2881
2882  aacccaaacaaggagctgaaacccggggaaaattcaccaagacagaccccccatctttgac  2941
2942  cctacagttcattggctgttcaccacatgtggggccagcgggccccatggccccacccag  3001
3002  gcacagtgcaacaacgcctaccagaactccaacctgagcgtggaggtggggagcgagggc  3061
3062  cccctgaaaggcatccagatctggaaggtgccagccaccgacacctacagcatctcgggc  3121
3122  tacggagctgctggcgggaaaggcgggaagaacaccatgatgcggtcccacggcgtgtct  3181
3182  gtgctgggcatcttcaacctggagaaggatgacatgctgtacatcctggttgggcagcag  3241
3242  ggagaggacgcctgccccagtacaaaccagttaatccagaaagtctgcattggagagaac  3301
3302  aatgtgatagaagaagaaatccgtgtgaacagaagcgtgcatgagtgggcaggaggcgga  3361
3362  ggaggagggggtggagccacctacgtatttaagatgaaggatggagtgccggtgcccctg  3421
3422  atcattgcagccggaggtggtggcagggcctacggggccaagacagacacgttccaccca  3481
3482  gagagactggagaataactcctcggttctagggctaaacggcaattccggagccgcaggt  3541
```

-continued 3542 ggtggaggtggctggaatgataacacttccttgctctgggccggaaaatctttgcaggag 3601

3602 ggtgccaccggaggacattcctgcccccaggccatgaagaagtgggggtgggagacaaga 3661

3662 gggggtttcggaggggggtggaggggggtgctcctcaggtggaggaggcggaggatatata 3721

3722 ggcggcaatgcagcctcaaacaatgaccccgaaatggatggggaagatggggtttccttc 3781

3782 atcagtccactgggcatcctgtacaccccagctttaaaagtgatggaaggccacggggaa 3841

3842 gtgaatattaagcattatctaaactgcagtcactgtgaggtagacgaatgtcacatggac 3901

3902 cctgaaagccacaaggtcatctgcttctgtgaccacgggacggtgctggctgaggatggc 3961

3962 gtctcctgcattgtgtcacccaccccggagccacacctgccactctcgctgatcctctct 4021

4022 gtggtgacctctgccctcgtggccgccctggtcctggctttctccggcatcatgattgtg 4081

4082 taccgccggaagcaccaggagctgcaagccatgcagatggagctgcagagccctgagtac 4141

4142 aagctgagcaagctccgcacctcgaccateatgaccgactacaaccccaactactgcttt 4201

4202 gctggcaagacctcctccatcagtgacctgaaggaggtgccgcggaaaaacatcaccctc 4261

4262 attcggggtctgggccatggcgcctttggggaggtgtatgaaggccaggtgtccggaatg 4321

4322 cccaacgacccaagcccccctgcaagtggctgtgaagacgctgcctgaagtgtgctctgaa 4381

4382 caggacgaactggatttcctcatggaagccctgatcatcagcaaattcaaccaccagaac 4441

4442 attgttcgctgcattggggtgagcctgcaatccctgccccggttcatcctgctggagctc 4501

4502 atggcgggggggagacctcaagtccttcctccgagagacccgccctcgcccgagccagccc 4561

4562 tcctccctggccatgctggaccttctgcacgtggctcgggacattgcctgtggctgtcag 4621

4622 tatttggaggaaaaccacttcatccaccgagacattgctgccagaaactgcctcttgacc 4681

4682 tgtccaggccctggaagagtggccaagattggagacttcgggatggcccgagacatctac 4741

4742 agggcgagctactatagaaagggaggctgtgccatgctgccagttaagtggatgcccccca 4801

4802 gaggccttcatggaaggaatattcacttctaaaacagacacatggtcctttggagtgctg 4861

4862 ctatgggaaatcttttctcttggatatatgccataccccagcaaaagcaaccaggaagtt 4921

4922 ctggagtttgtcaccagtggaggccggatggacccacccaagaactgccctgggcctgta 4981

4982 taccggataatgactcagtgctggcaacatcagcctgaagacaggcccaactttgccatc 5041

5042 attttggagaggattgaatactgcacccaggacccggatgtaatcaacaccgctttgccg 5101

5102 atagaatatggtccacttgtggaagaggaagagaaagtgcctgtgaggcccaaggaccct 5161

5162 gaggggggttcctcctctcctggtctctcaacaggcaaaacgggaggaggagcgcagccca 5221

5222 gctgccccaccacctctgcctaccacctcctctggcaaggctgcaaagaaacccacagct 5281

5282 gcagagatctctgttcgagtccctagagggccggccgtggaagggggacacgtgaatatg 5341

5342 gcattctctcagtccaaccctccttcggagttgcacaaggtccacggatccagaaacaag 5401

5402 cccaccagcttgtggaacccaacgtacggctcctggtttacagagaaacccaccaaaaag 5461

5462 aataatcctatagcaaagaaggagccacacgacaggggtaacctggggctggagggaagc 5521

5522 tgtactgtcccacctaacgttgcaactgggagacttccgggggcctcactgctcctagag 5581

5582 ccctcttcgctgactgccaatatgaaggaggtacctctgttcaggctacgtcacttccct 5641

5642 tgtgggaatgtcaattacggctaccagcaacagggcttgcccttagaagccgctactgcc 5701

5702 cctggagctggtcattacgaggataccattctgaaaagcaagaatagcatgaaccagcct 5761

5762 gggccctgagctcggtcgcacactcacttctcttccttgggatccctaagaccgtggagg 5821

5822 agagagaggcaatggctccttcacaaaccagagaccaaatgtcacgttttgttttgtgcc 5881

5882 aacctattttgaagtaccaccaaaaaagctgtattttgaaaatgctttagaaaggttttg 5941

5942 agcatgggttcatcctattctttcgaaagaagaaaatatcataaaaatgagtgataaata 6001

-continued

```
6002   caaggcccagatgtggttgcataaggtttttatgcatgtttgttgtatacttccttatgc  6061
6062   ttctttcaaattgtgtgtgctctgcttcaatgtagtcagaattagctgcttctatgtttc  6121
6122   atagttggggtcatagatgtttccttgccttgttgatgtggacatgagccatttgagggg  6181
6182   agagggaacggaaataaaggagttatttgtaatgactaaaa                     6222
```

The vectors used to express an ALK antigen as described herein may be any suitable expression vector known and used in the art. In some embodiments, the vector is a prokaryotic or eukaryotic vector. In some embodiments, the vector is an expression vector, such as a eukaryotic (e.g., mammalian) expression vector. In another embodiment, the vector is a plasmid (prokaryotic or bacterial) vector. In another embodiment, the vector is a viral vector.

Provided are isolated, non-naturally occurring polypeptide antigens, e.g., ALK polypeptide antigens, produced by transfecting a host cell with an expression vector as known and used in the art under conditions sufficient to allow for expression of the polypeptide, e.g., an ALK polypeptide, in the cell. Isolated cells containing the vectors are also provided.

Also provided is an ALK polypeptide, as described herein, produced by transfecting a host cell with a vector containing a polynucleotide encoding the ALK polypeptide. Also provided in some embodiments is an ALK polypeptide, as described herein, produced by transfecting a host cell with a vector encoding the ALK polypeptide under conditions sufficient to allow for expression of the ALK protein. Collections of plasmids (vectors) are also contemplated. In certain embodiments, the collection of plasmids includes plasmid encoding an ALK protein as described herein.

Compositions and Pharmaceutical Compositions for Administration

Compositions comprising at least one ALK protein, or a polynucleotide encoding at least one ALK protein, as described herein are provided. In some embodiments, the compositions further comprise a pharmaceutically acceptable carrier, diluent, excipient, or vehicle. In some embodiments, an adjuvant (a pharmacological or immunological agent that modifies or boosts an immune response, e.g., to produce more antibodies that are longer-lasting) is also employed. For example, without limitation, the adjuvant can be an inorganic compound, such as alum, aluminum hydroxide, or aluminum phosphate; mineral or paraffin oil; squalene; detergents such as Quil A; plant saponins; Freund's complete or incomplete adjuvant, a biological adjuvant (e.g., cytokines such as IL-1, IL-2, or IL-12); bacterial products such as killed *Bordetella pertussis*, or toxoids; or immunostimulatory oligonucleotides (such as CpG oligonucleotides). In some embodiments, the adjuvant is conjugated to an amphiphile as previously described (H. Liu et al., Structure-based programming of lymph-node targeting in molecular vaccines. Nature 507, 5199522 (2014)). In some embodiments, the amphiphile is N-hydroxy succinimidyl ester-end-functionalized poly(ethylene glycol)-lipid (NHS-PEG2KDa-DSPE)

Compositions and preparations (e.g., physiologically or pharmaceutically acceptable compositions) containing ALK polypeptides or polynucleotides for parenteral administration include, without limitation, sterile aqueous or non-aqueous solutions, suspensions, and emulsions. Nonlimiting examples of non-aqueous solvents include propylene glycol, polyethylene glycol, vegetable oils, such as olive oil and canola oil, and injectable organic esters, such as ethyl oleate. Aqueous carriers include water, alcoholic/aqueous solutions, emulsions or suspensions, including saline and buffered media. Parenteral vehicles include, for example, sodium chloride solution, Ringer's dextrose, dextrose and sodium chloride, lactated Ringer's, or fixed oils. Intravenous vehicles include, for example, fluid and nutrient replenishers, electrolyte replenishers (such as those based on Ringer's dextrose), and the like. Preservatives and other additives may also be present in such compositions and preparations, such as, for example, antimicrobials, antioxidants, chelating agents, colorants, stabilizers, inert gases and the like.

Some of the compositions may potentially be administered as a pharmaceutically acceptable acid- or base-addition salt, formed by reaction with inorganic acids, such as hydrochloric acid, hydrobromic acid, perchloric acid, nitric acid, thiocyanic acid, sulfuric acid, and phosphoric acid, and organic acids, such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, tri-alkyl and aryl amines and substituted ethanolamines.

Provided herein are pharmaceutical compositions which include a therapeutically effective amount of an isolated ALK polypeptide or polynucleotide antigen, alone, or in combination with a pharmaceutically acceptable carrier. Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid or aqueous solution, suspension, emulsion, dispersion, tablet, pill, capsule, powder, or sustained release formulation. A liquid or aqueous composition can be lyophilized and reconstituted with a solution or buffer prior to use. The composition can be formulated as a suppository, with traditional binders and carriers such as triglycerides. Oral formulations can include standard carriers, such as pharmaceutical grades of mannitol, lactose, starch, magnesium stearate, sodium saccharine, cellulose, and magnesium carbonate. Any of the commonly known pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used in the compositions and administration methods as described are normal saline and sesame oil.

Methods of Treatment, Administration and Delivery

Methods of treating a disease, or symptoms thereof, caused by the oncogenic ALK gene fusions, rearrangements, duplications or mutations (e.g., ALK-positive cancers) are provided. The methods comprise administering a therapeutically effective amount of an antigen, immunogen, immunogenic composition, or vaccine, as described herein, or a pharmaceutical composition comprising the immunogen or a vaccine, as described herein, to a subject (e.g., a mammal), in particular, a human subject. The invention provides methods of treating a subject suffering from, or at risk of, or susceptible to disease, or a symptom thereof, or delaying the progression of a disease caused by oncogenic ALK gene fusions, rearrangements, duplications or mutations (e.g., ALK-positive cancers). In some embodiments, the method includes administering to the subject (e.g., a mammalian subject), an amount or a therapeutic amount of an immunogenic composition or a vaccine comprising at least one ALK antigen polypeptide, sufficient to treat the disease, delay the growth of, or treat the symptoms thereof, caused by the oncogenic ALK gene under conditions in which the disease and/or the symptoms thereof are treated.

In some embodiments, the methods herein include administering to the subject (including a human subject identified as in need of such treatment) an effective amount of an isolated, ALK antigen or immunogen polypeptide, or an immunogenic composition or vaccine, or a pharmaceutical composition thereof, as described herein to produce such effect. The treatment methods are suitably administered to subjects, particularly humans, suffering from, are susceptible to, or at risk of having a disease, or symptoms thereof, caused by oncogenic ALK gene fusions, rearrangements, duplications or mutations, namely, ALK-positive cancers. Nonlimiting examples of ALK-positive cancers include non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, melanoma, or a combination thereof.

Identifying a subject in need of such treatment can be based on the judgment of the subject or of a health care professional and can be subjective (e.g., opinion) or objective (e.g., measurable by a test or diagnostic method). Briefly, the determination of those subjects who are in need of treatment or who are "at risk" or "susceptible" can be made by any objective or subjective determination by a diagnostic test (e.g., blood sample, biopsy, genetic test, enzyme or protein marker assay), marker analysis, family history, and the like, including an opinion of the subject or a health care provider. In some embodiments, the subject in need of treatment can be identified by measuring ALK specific autoantibodies and ALK-specific T-cell responses in a patient sample (e.g., blood sample) or by assessing infiltrating immune cell subsets from a tumor core biopsy from a subject (see Example 3). The ALK antigens and immunogens, such as ALK polypeptides, immunogenic compositions and vaccines as described herein, may also be used in the treatment of any other disorders in which disease caused by oncogenic ALK gene fusions, rearrangements, duplications or mutations may be implicated. A subject undergoing treatment can be a non-human mammal, such as a veterinary subject, or a human subject (also referred to as a "patient").

In addition, prophylactic methods of preventing or protecting against a disease, or symptoms thereof, caused by oncogenic ALK gene fusions, rearrangements, duplications or mutations are provided. Such methods comprise administering a therapeutically effective amount of a pharmaceutical composition comprising an ALK immunogenic composition or vaccine as described herein to a subject (e.g., a mammal, such as a human), in particular, prior to development or onset of a disease, such as ALK-positive tumors or cancers.

In another embodiment, a method of monitoring the progress of a disease caused by oncogenic ALK gene fusions, rearrangements, duplications or mutations (e.g., ALK-positive cancers), or monitoring treatment of the disease is provided. The method includes a diagnostic measurement (e.g., CT scan, screening assay or detection assay) in a subject suffering from or susceptible to disease or symptoms thereof associated with oncogenic ALK gene fusions, rearrangements, duplications or mutations (e.g., ALK-positive cancers), in which the subject has been administered an amount (e.g., a therapeutic amount) of an isolated ALK protein, as described herein, or an immunogenic composition or vaccine as described herein, sufficient to treat the disease or symptoms thereof. The diagnostic measurement in the method can be compared to samples from healthy, normal controls; in a pre-disease sample of the subject; or in other afflicted/diseased patients to establish the treated subject's disease status. For monitoring, a second diagnostic measurement may be obtained from the subject at a time point later than the determination of the first diagnostic measurement, and the two measurements can be compared to monitor the course of disease or the efficacy of the therapy/treatment. In certain embodiments, a pre-treatment measurement in the subject (e.g., in a sample or biopsy obtained from the subject or CT scan) is determined prior to beginning treatment as described; this measurement can then be compared to a measurement in the subject after the treatment commences and/or during the course of treatment to determine the efficacy of (monitor the efficacy of) the disease treatment. In some embodiments, efficacy of the disease treatment can be performed with antibody marker analysis and/or interferon-gamma (IFN-γ) ELISPOT assays.

The isolated ALK antigen polypeptide, or compositions thereof, can be administered to a subject by any of the routes normally used for introducing a recombinant protein or composition containing the recombinant protein into a subject. Routes and methods of administration include, without limitation, intradermal, intramuscular, intraperitoneal, intrathecal, parenteral, such as intravenous (IV) or subcutaneous (SC), vaginal, rectal, intranasal, inhalation, intraocular, intracranial, or oral. Parenteral administration, such as subcutaneous, intravenous or intramuscular administration, is generally achieved by injection (immunization). Injectables can be prepared in conventional forms and formulations, either as liquid solutions or suspensions, solid forms (e.g., lyophilized forms) suitable for solution or suspension in liquid prior to injection, or as emulsions. Injection solutions and suspensions can be prepared from sterile powders, granules, and tablets. Administration can be systemic or local.

The isolated ALK polypeptides or compositions thereof, can be administered in any suitable manner, such as with pharmaceutically acceptable carriers, diluents, or excipients as described supra. Pharmaceutically acceptable carriers are determined in part by the particular immunogen or composition being administered, as well as by the particular method used to administer the composition. Accordingly, a pharmaceutical composition comprising the isolated ALK antigen polypeptides or compositions thereof, can be prepared using a wide variety of suitable and physiologically and pharmaceutically acceptable formulations.

Further provided is a method of eliciting or generating an immune response in a subject with a disease caused by oncogenic ALK gene fusions, rearrangements, duplications or mutations (e.g., ALK-positive cancers) by administering to the subject an isolated ALK protein antigen or immunogen, or immunogenic composition or vaccine thereof, as described herein. In some embodiments, the ALK protein can be administered using any suitable route of administration, such as, for example, by intramuscular injection. In some embodiments, the ALK protein is administered as a composition comprising a pharmaceutically acceptable carrier. In some embodiments, the composition comprises an adjuvant selected from, for example, alum, Freund's complete or incomplete adjuvant, a biological adjuvant or immunostimulatory oligonucleotides (such as CpG oligonucleotides). In some embodiments, the adjuvant is conjugated to an amphiphile. In other embodiments, the composition may be administered in combination with one or more therapeutic agents or molecules.

Also provided is a method of immunizing a subject against disease or the symptoms thereof caused by oncogenic ALK gene fusions, rearrangements, duplications or mutations (e.g., ALK-positive cancers), in which the method involves administering to the subject an isolated ALK protein as described herein, or administering an immunogenic composition or vaccine thereof. In some embodiments of the method, the composition further comprises a pharmaceutically acceptable carrier, diluent, excipient, and/or an adjuvant. For example, the adjuvant can be alum, Freund's complete or incomplete adjuvant, a biological adjuvant or immunostimulatory oligonucleotides (such as CpG oligonucleotides). In some embodiments, the adjuvant is conjugated to an amphiphile. In some embodiments, the ALK peptides (or compositions thereof) are administered intramuscularly.

An advantage of the immunogens and immunogenic compositions comprising ALK antigens described herein is that an immune response is elicited against not only the ALK-expressing tumor or cell line from which the antigen was derived, but also against one or more, or all, ALK-positive cancers, e.g., non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, melanoma, or a combination thereof. In some embodiments, the immunogens and immunogenic compositions described herein elicit immune responses against NSCLC. In some embodiments, the immunogens and immunogenic compositions described herein elicit immune responses against ALCL. Thus, the ALK immunogens are more cost effective to produce, and beneficially elicit an immune response, thus, obviating a need to make and administer a poly- or multivalent immunogenic composition or vaccine.

Figure 7A:
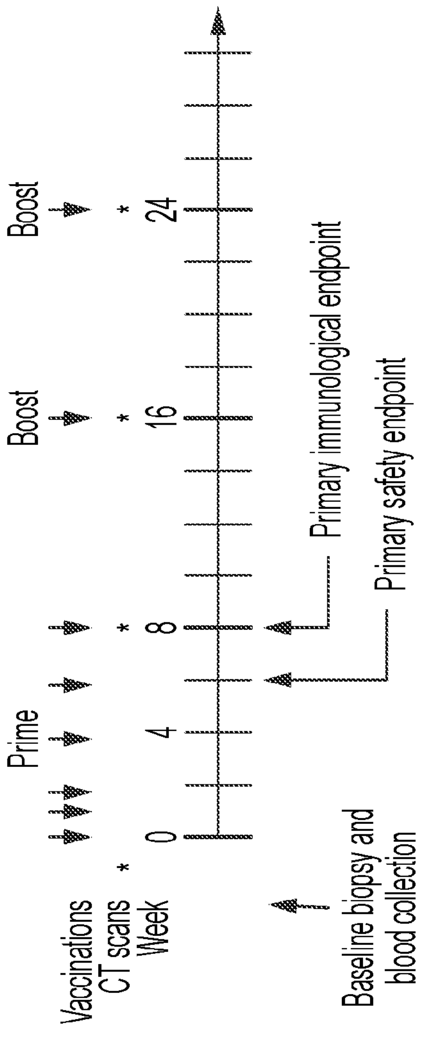
FIGS. 7A and 7B depict schematic illustrations of ALK-peptide vaccination administration schedules.

Administration of the isolated ALK antigen polypeptides or compositions thereof, can be accomplished by single or multiple doses. In some embodiments, the doses can be administered according to the vaccination schedule described in Example 3 and FIG. 7A. The dose administered to a subject should be sufficient to induce a beneficial therapeutic response in a subject over time, such as to inhibit, block, reduce, ameliorate, protect against, or prevent disease caused by oncogenic ALK gene fusions, rearrangements, duplications or mutations (e.g., ALK-positive cancers). The dose required will vary from subject to subject depending on the species, age, weight and general condition of the subject, by the severity of the cancer being treated, by the particular composition being used and by the mode of administration. An appropriate dose can be determined by a person skilled in the art, such as a clinician or medical practitioner, using only routine experimentation. One of skill in the art is capable of determining therapeutically effective amounts of ALK antigen or immunogen, or immunogenic compositions or vaccines thereof, that provide a therapeutic effect or protection against diseases caused by ALK gene fusions, rearrangements, duplications or mutations (e.g., ALK-positive cancers) suitable for administering to a subject in need of treatment or protection.

Adjuvants and Combination Therapies

The ALK immunogens or immunogenic compositions or vaccines containing an ALK-specific peptide antigen can be administered alone or in combination with other therapeutic agents to enhance antigenicity or immunogenicity, i.e., to increase an immune response, such as the elicitation of specific or neutralizing antibodies, in a subject. For example, the ALK-specific peptide can be administered with an adjuvant, such as alum, Freund's incomplete adjuvant, Freund's complete adjuvant, biological adjuvant, or immunostimulatory oligonucleotides (such as CpG oligonucleotides). The adjuvant may be conjugated to an amphiphile as previously described (H. Liu et al., Structure-based programming of lymph-node targeting in molecular vaccines. *Nature* 507, 5199522 (2014)). In some embodiments, the amphiphile conjugated to the adjuvant is N-hydroxy succinimidyl ester-end-functionalized poly(ethylene glycol)-lipid (NHS-PEG2KDa-DSPE).

One or more cytokines, such as interleukin-1 (IL-2), interleukin-6 (IL-6), interleukin-12 (IL-12), the protein memory T-cell attractant "Regulated on Activation, Normal T Expressed and Secreted" (RANTES), granulocyte-macrophage-colony stimulating factor (GM-CSF), tumor necrosis factor-alpha (TNF-α), or interferon-gamma (IFN-γ); one or more growth factors, such as GM-CSF or granulocyte-colony stimulation factor (G-CSF); one or more molecules such as the TNF ligand superfamily member 4 ligand (OX40L) or the type 2 transmembrane glycoprotein receptor belonging to the TNF superfamily (4-1BBL), or combinations of these molecules, can be used as biological adjuvants, if desired or warranted (see, e.g., Salgaller et al., 1998, *J. Surg. Oncol.* 68(2):122-38; Lotze et al., 2000, *Cancer J. Sci. Am.* 6(Suppl 1):561-6; Cao et al., 1998, *Stem Cells* 16(Suppl 1):251-60; Kuiper et al., 2000, *Adv. Exp. Med. Biol.* 465:381-90). These molecules can be administered systemically (or locally) to a subject.

Several ways of inducing cellular responses, both in vitro and in vivo, are known and practiced in the art. Lipids have been identified as agents capable of assisting in priming cytotoxic lymphocytes (CTL) in vivo against various antigens. For example, palmitic acid residues can be attached to the alpha and epsilon amino groups of a lysine residue and then linked (for example, via one or more linking residues, such as glycine, glycine-glycine, serine, serine-serine, or the like) to an immunogenic peptide (U.S. Pat. No. 5,662,907). The lipidated peptide can then be injected directly in a micellar form, incorporated in a liposome, or emulsified in an adjuvant. As another example, *E. coli* lipoproteins, such as tripalmitoyl-S-glycerylcysteinlyseryl-serine can be used to prime tumor-specific CTL when covalently attached to an appropriate peptide (see, e.g., Deres et al., 1989, *Nature* 342:561). Moreover, the induction of neutralizing antibodies can also be primed with the same molecule conjugated to a peptide which displays an appropriate epitope, and two compositions can be combined to elicit both humoral and cell-mediated responses where such a combination is deemed desirable.

The ALK-specific peptides can also be administered as a combination therapy with one or more other therapeutic agents, such as ALK inhibitors, tyrosine kinase inhibitors (TKIs), and/or immune checkpoint inhibitors. Non-limiting examples of ALK inhibitors include lorlatinib (Lobrena®). Non-limiting examples of checkpoint inhibitors include programmed cell death protein 1 (PD-1) inhibitors, programmed death-ligand 1 (PD-L1), and cytotoxic T-lymphocyte-associated antigen-4 (CTLA-4) inhibitors. Nonlimiting examples of PD-1 inhibitors include pembrolizumab (Keytruda®) and nivolumab (Opdivo®). Nonlimiting examples of CTLA-4 inhibitors include ipilimumab (Yervoy®). Non-limiting examples of TKI inhibitors include crizotinib, ceritinib, alectinib, brigatinib, and lorlatinib.

In some embodiments, one or more ALK inhibitors, immune checkpoint inhibitors, and/or TKI inhibitors is administered simultaneously or sequentially with ALK-specific peptide antigens, immunogens, or immunogenic compositions or vaccines containing an ALK-specific peptide antigen or immunogen. In some embodiments, the ALK-specific peptide antigen, immunogen, or immunogenic composition or vaccine containing an ALK-specific peptide antigen or immunogen is administered with a PD-1 inhibitor. In some embodiments, the PD-1 inhibitor is an anti-PD-1 antibody. In some embodiments, the ALK-specific peptide antigen, immunogen, or immunogenic composition or vaccine containing an ALK-specific peptide antigen or immunogen is administered with a PD-1 inhibitor according to the schedule described in Example 3 and/or FIG. 7B. In some embodiments, the ALK-specific peptide antigen, immunogen, or immunogenic composition or vaccine containing an ALK-specific peptide antigen or immunogen is administered with a PD-L1 inhibitor.

In some embodiments, the ALK-specific peptide antigen, immunogen, or immunogenic composition or vaccine containing an ALK-specific peptide antigen or immunogen is administered with a TKI inhibitor. In some embodiments, the ALK-specific peptide antigen, immunogen, or immunogenic composition or vaccine containing an ALK-specific peptide antigen or immunogen is administered with an ALK inhibitor. In some embodiments, the ALK-specific peptide antigen, immunogen, or immunogenic composition or vaccine containing an ALK-specific peptide antigen or immunogen is administered with lorlatinib.

In some embodiments, the ALK-specific peptide antigen, immunogen, or immunogenic composition or vaccine containing an ALK-specific peptide antigen or immunogen is administered with a PD-1 inhibitor in combination with an ALK inhibitor. In some embodiments, the ALK-specific peptide antigen, immunogen, or immunogenic composition or vaccine containing an ALK-specific peptide antigen or immunogen is administered with an anti-PD-1 antibody in combination with lorlatinib. In some embodiments, the ALK-specific peptide antigen, immunogen, or immunogenic composition or vaccine containing an ALK-specific peptide antigen or immunogen is administered with an anti-PD-1 antibody in combination with lorlatinib according to the schedule described in Example 4 and/or FIG. 8A.

While treatment methods may involve the administration of a vaccine containing a ALK immunogenic protein as described herein, one skilled in the art will appreciate that the ALK protein itself, as a component of a pharmaceutically acceptable composition or as a fusion protein, can be administered to a subject in need thereof to elicit an immune response against an ALK-positive cancer in the subject.

Kits

Also provided are kits containing the ALK antigen or immunogen as described, or an immunogenic composition, or a vaccine, or a pharmaceutically acceptable composition containing the antigen or immunogen and a pharmaceutically acceptable carrier, diluent, or excipient, for administering to a subject, for example. The antigen or immunogen may be in the form of an ALK protein (polypeptide) or a polynucleotide (a polynucleotide encoding an ALK polypeptide), as described herein. Kits containing one or more of the plasmids, or a collection of plasmids as described herein, are also provided. As will be appreciated by the skilled practitioner in the art, such a kit may contain one or more containers that house the antigen, immunogen, vaccine, or composition, carriers, diluents or excipients, as necessary, and instructions for use.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "*Molecular Cloning: A Laboratory Manual*", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Useful techniques for particular embodiments will be discussed in the sections that follow.

The following examples are put forth to provide those of ordinary skill in the art with a complete disclosure and description of how to make and use the assay, screening, and therapeutic methods of the invention, and are not intended to limit the scope of what the inventors regard as their invention.

EXAMPLES

The following examples are provided to illustrate certain particular features and/or embodiments. The examples should not be construed to limit the disclosure to the particular features or embodiments described.

Example 1. Identification of ALK-Specific Peptides for an ALK-Positive Cancer Vaccine The direct identification of ALK peptides that are effectively presented on the surface of ALK-expressing cancer cells in the context of the most frequent patient haplotypes will provide a powerful resource to design the most effective vaccine to elicit ALK-specific T-cell responses.

Example 1.1 Identification of ALK-Specific Peptides in Different HLA-Haplotypes The B721.221 human lymphoblastic cell line does not express endogenous HLA class I (A, B and C) due to gamma-ray-induced mutations in the HLA complex. (Shimizu Y, DeMars R. Production of human cells expressing individual transferred HLA-A, -B, -C genes using an HLA-A, -B, -C null human cell line. *J. Immunol.* 1989; 142(9): 3320-3328). Fifty (50) cell lines each expressing a single HLA class I allele (monoallelic cell lines) were generated by transducing B721.221 cells with retroviruses encoding HLA class I genes. This tool allows the unequivocal assignation of peptides identified by mass spectrometry to a specific HLA class I allele. The HLA-peptide complexes were immunoprecipitated with an anti-HLA A/B/C antibody (clone W6/32, Santa Cruz) and the peptides released were analyzed by liquid chromatography-tandem mass spectrometry (LC- MS/MS). Using retroviral transduction, the EML4-ALK variant 1, the most frequent EML4-ALK fusion protein (Lin J J, et al. Impact of EML4-ALK Variant on Resistance Mechanisms and Clinical Outcomes in ALK-Positive Lung Cancer. *J. Clin. Oncol.* 2018:JC02017762294), was expressed into different HLA-monoallelic B721.221 cell lines (FIG. 1A). The selection of the different cell lines to be transduced was based on the frequency of HLA class I alleles among patients with ALK-positive NSCLC (Table 1). B721.221/A*02:01, B721.221/A*01:01 and B721.221/C*06:02 cells were transduced with a construct encoding the EML4-ALK variant 1 and GFP. Cells were sorted based on the GFP positivity and expanded. A western blot was performed using an untransduced B721.221/A*02:01 cell line as a negative control and the H3122 ALK+NSCLC cell line as a positive control.

Figure 1B:
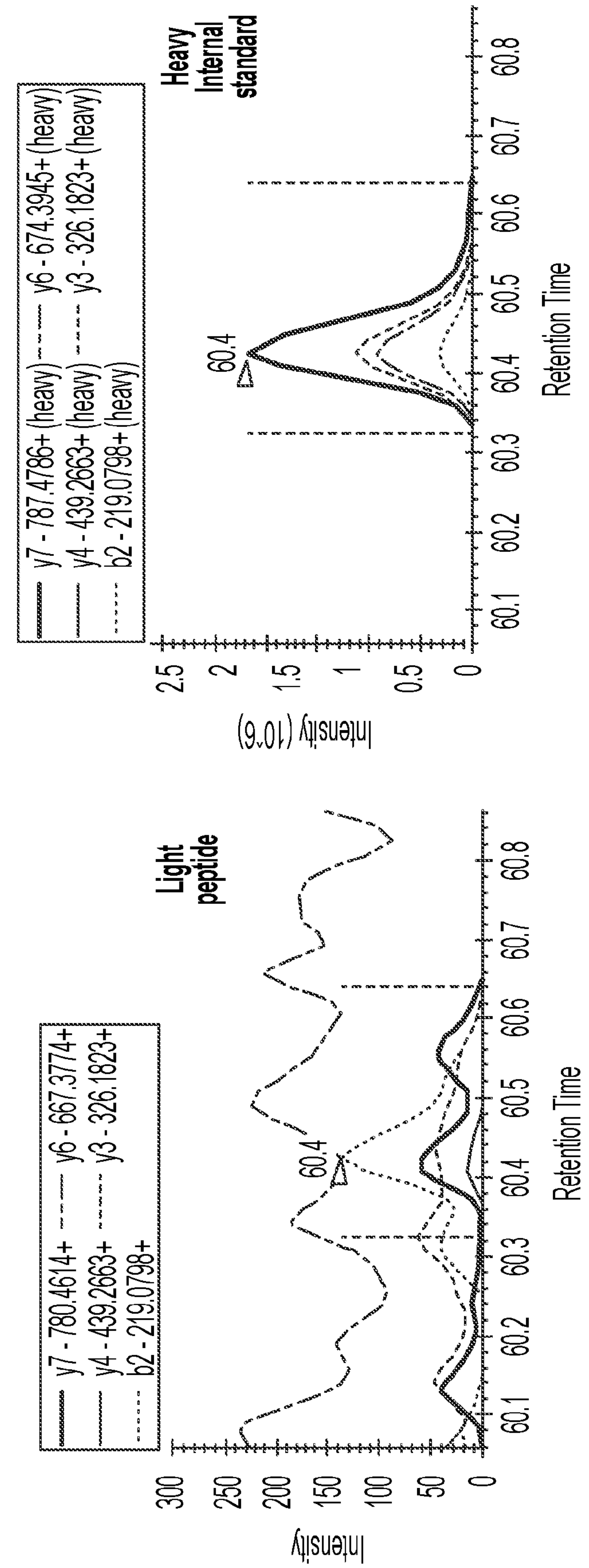

Using the most sensitive targeted mass spectrometry, two (2) peptides predicted by the algorithms from the immune epitope database (IEDB), AMLDLLHVA (SEQ ID NO: 1) and SLAMLDLLHV (SEQ ID NO: 16), were isotope-labelled (heavy standard) and searched in HLA*02:01 elute from B721.221/A*02:01 cells. Only the 9-mer, AMLDLLHVA (SEQ ID NO: 1), ALK-specific peptide binding the HLA A*02:01 allele was identified (FIG. 1B). ALK-specific peptides were not identified in the HLA A*01:01, HLA A*02:01 or HLA C*06:02 eluates using discovery mass spectrometry. Since protein overexpression can compensate for low binding affinity of the peptides for the HLA proteins (see, e.g., Abelin J G, et al. Mass Spectrometry Profiling of HLA-Associated Peptidomes in Mono-allelic Cells Enables More Accurate Epitope Prediction. Immunity. 2017; 46(2): 315-326) and considering that the level of EML4-ALK expression in B721.221/HLA A*02:01 cells was at least one order of magnitude below the range of expression of the reference NSCLC H3122 cell line (FIG. 1A), the identified ALK peptide, AMLDLLHVA (SEQ ID NO: 1), was determined to be presented on the surface of tumor cells with a strong affinity for HLA A*02:01.

TABLE 1

Percentage of different HLA class I alleles among 100 ALK-positive lung cancer patients.

| HLA A | | HLA B | | HLA C | |
|---|---|---|---|---|---|
| Allele | Frequency | Allele | Frequency | Allele | Frequency |
| *02:01 | 43% | *07:02 | 18% | *07:01 | 27% |
| *01:01 | 26% | *08:01 | 15% | *04:01 | 26% |
| *24:02 | 24% | *35:01 | 12% | *06:02 | 24% |
| *03:01 | 22% | *18:01 | 10% | *07:02 | 22% |
| *11:01 | 12% | *44:02 | 10% | *03:04 | 15% |

Example 1.2 Identification of ALK-Specific Peptides in Different Cell Lines

The low levels of EML4-ALK expression reached by transducing B721.221 cells make it difficult to identify ALK-specific peptides normally expressed on the surface of tumor cells. In order to avoid this technical challenge, different ALK-positive anaplastic large cell lymphoma (ALCL) cell lines encoding frequent HLA-alleles were selected (Karpas-299, DEL, and SR-786). ALCL cell lines express high levels of the NPM-ALK fusion protein, a fusion protein containing the exactly same ALK portion as the EML4-ALK fusion protein. The HLA genotype and HLA expression on the selected cell lines were confirmed before proceeding with mass spectrometry experiments (Table 2). The two HLA-A, -B and -C alleles were determined by Next Generation sequencing (NGS). Expression levels of HLA were determined by flow cytometry with a pan-HLA antibody. Positive or negative antibody staining for anti-HLA-A*02, which recognizes all the allelic variants of HLA-A*02, and anti-DR, which recognizes all the HLA class II DR (HLA-DR) subclasses, was determined by flow cytometry.

TABLE 2

Characterization of ALK-positive ALCL cell lines.

| | | Next Generation Sequencing | | | | | | Antibody Staining | | |
|---|---|---|---|---|---|---|---|---|---|---|
| | HLA | A(1) | A(2) | B(1) | B(2) | C(1) | C(2) | Pan-HLA | A02 | DR |
| ALCL | KARPAS | *03:01 | *11:01 | *07:02 | *35:01 | *04:01 | *07:02 | (+++) | No | Yes |
| Cell | DEL | *26:01 | *02:01 | *14:01 | *27:05 | *08:02 | *05:01 | (++++) | Yes | Yes |
| Lines | SR786 | *02:01 | *68:02 | *55:01 | *57:01 | *03:03 | *06:02 | (+++) | Yes | No |

Figure 2A:
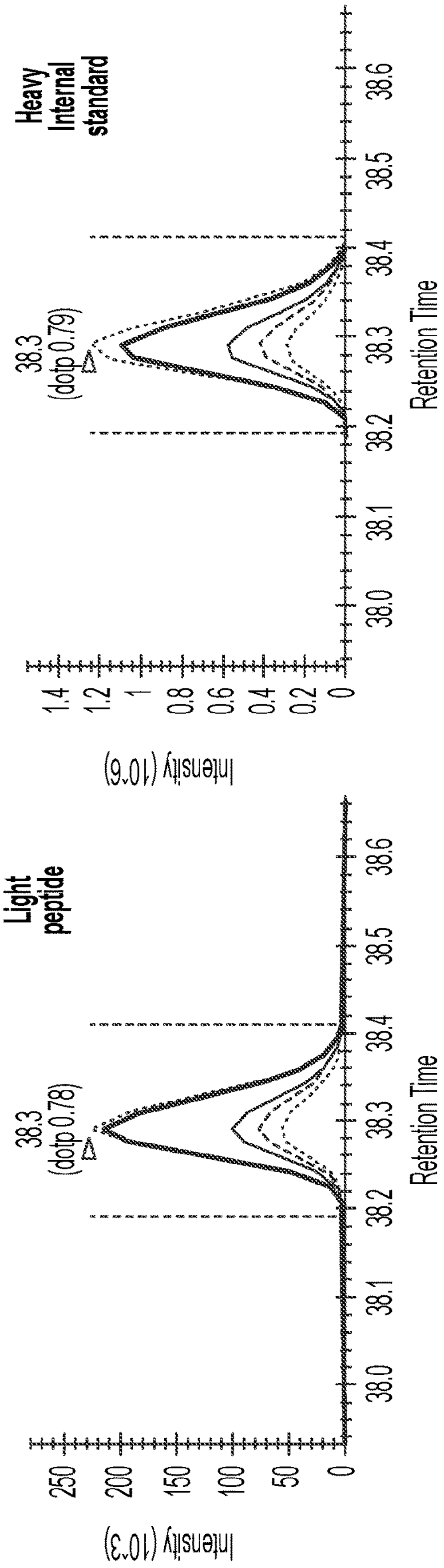
FIGS. 2A-2D depict the identification of ALK-specific peptides in ALK-positive ALCL cell lines.
Figure 2B:
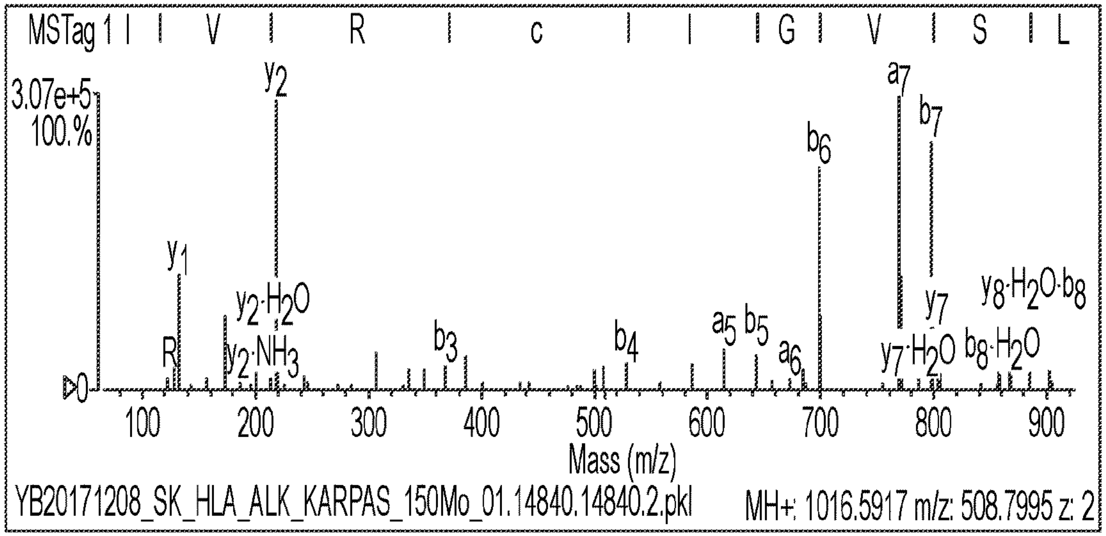
Figure 2C:
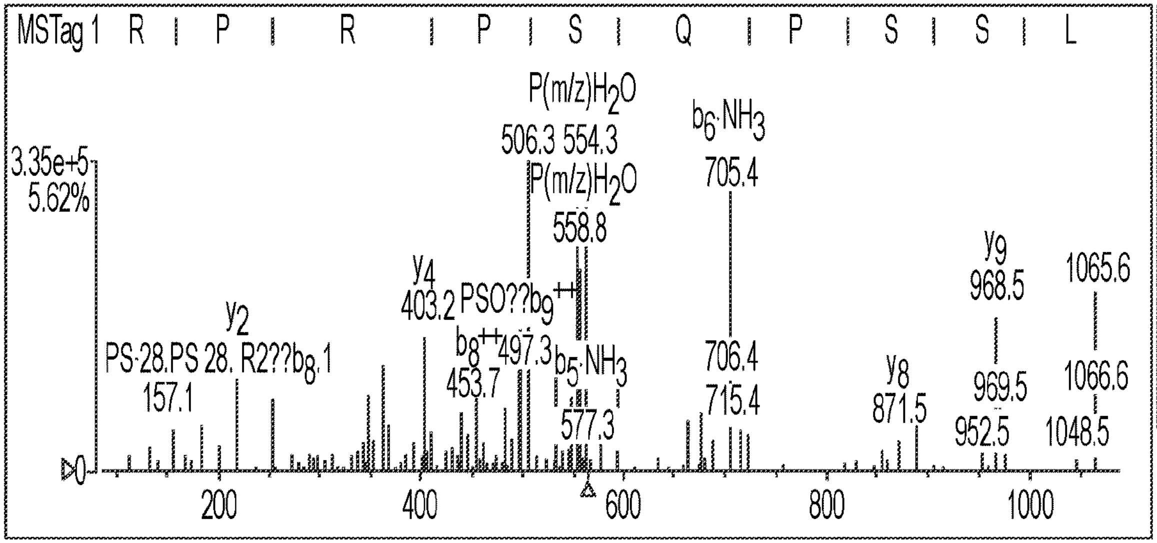
Figure 2D:
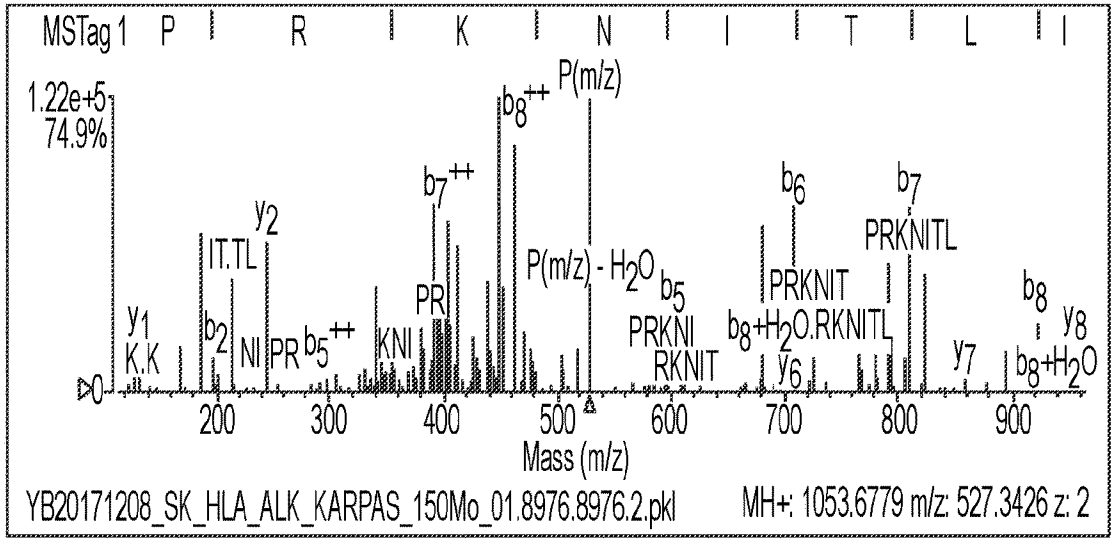

Since the HLA A*02:01 allele can be immunoprecipitated by a specific antibody (BB7.2 clone), the peptide, AMLDLLHVA (SEQ ID NO: 1), previously identified in B721.221/HLA A*02:01 cells, was isotope-labeled (heavy standard) and its presence was confirmed by targeted mass spectrometry in the HLA A*02:01 elute of DEL cells (FIG. 2A). For cell lines expressing different HLAs than HLA A*02:01, the HLA-peptide complexes were pulled down with an anti-pan-HLA antibody. ALK-specific peptides in the HLAs elutes were then searched by mass spectrometry in discovery mode. The system and algorithm as provided in Abelin J G, et al. (Mass Spectrometry Profiling of HLA-Associated Peptidomes in Mono-allelic Cells Enables More Accurate Epitope Prediction. Immunity. 2017; 46(2):315-326) was used to assign the discovered peptides to a specific HLA. This algorithm was trained with the endogenous peptides presented by several of the aforementioned HLA-monoallelic cell lines. Following this approach, three (3) ALK-specific peptides presented in the HLA elute from Karpas-299 cells were identified (FIGS. 2B-2D). Two independent injections were run in the mass spectrometer. IVRCIGVSL (SEQ ID NO: 3) and RPRPSQPSSL (SEQ ID NO: 2) were found in both injections (FIGS. 2B and 2C, respectively). VPRKNITLI (SEQ ID NO: 4) was only found in one of the two injections (FIG. 2D). All three (3) peptides were strongly predicted to bind the HLA B*07:02 allele (FIGS. 2B-2D).

This data showed the physiological processing and presentation of four (4) different ALK-peptides on the groove of two frequent HLA class I haplotypes, HLA A*02:01 and HLA B*07:02, by cancer cells (Table 3). The peptides described in Table 3 belong to the intracytoplasmic portion of ALK; therefore, are comprised in all the possible forms of ALK aberrant expression, such as overexpression (neuroblastoma) or the EML4-ALK (NSCLC) and NPM-ALK (ALCL) translocations. Based on the frequency of these HLA class I alleles among individuals with ALK-positive NSCLC, a therapeutic vaccine against these peptides would be applicable to about 54% of patients.

Figure 3:
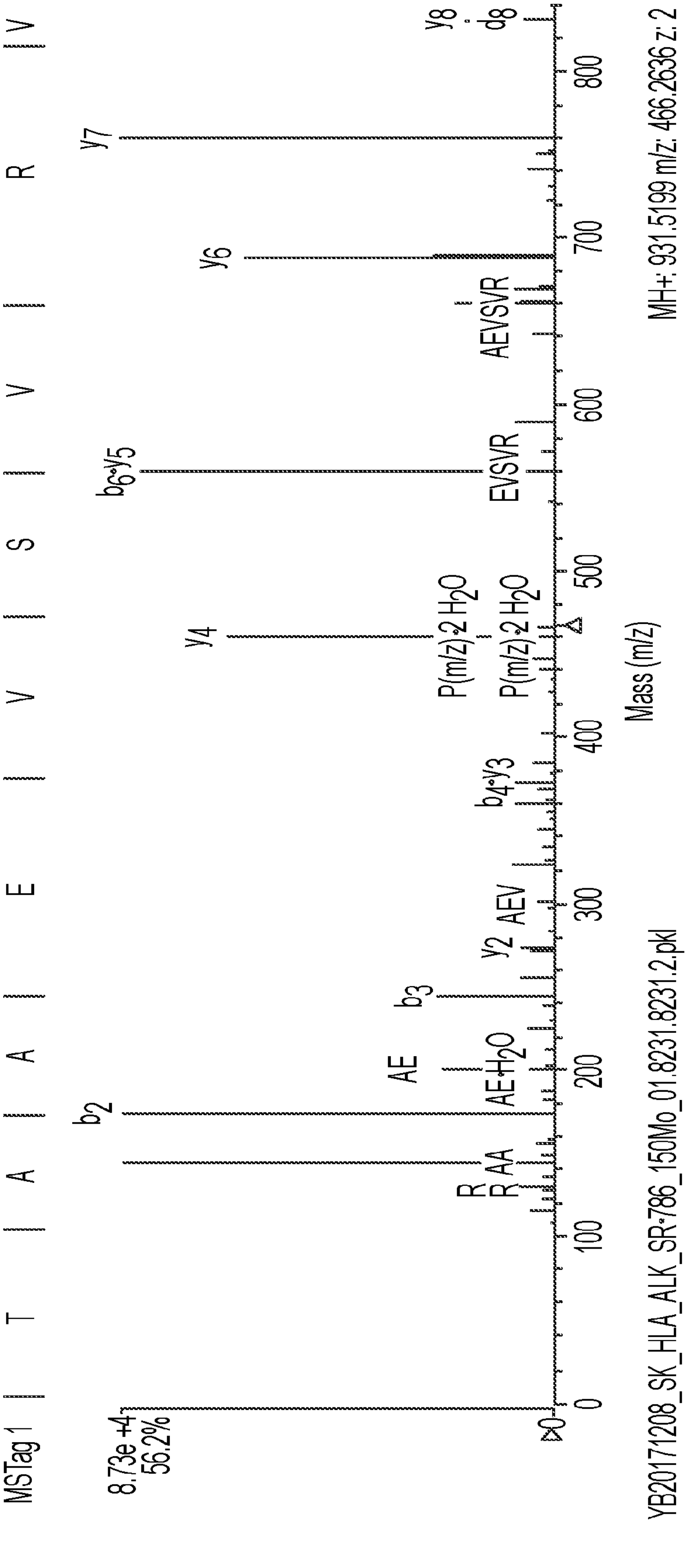
FIG. 3 provides a graphical depiction of discovery mass spectrometry of the TAAEVSVRV (SEQ ID NO: 5) ALK-peptide identified in HLA elute from the SR-786 cell line.

In addition, the 9-mer peptide, TAAEVSVRV (SEQ ID NO: 5), was identified in two independent experiments using pan-HLA elute from SR-786 cells (FIG. 3). According to the NetMHCpan and Artificial Neural Network (ANN) algorithms from IEDB, this peptide binds the HLA A*68:02 allele (Table 3), an allele found in about 5% of patients with ALK-positive tumors.

TABLE 3

Peptides discovered by mass spectrometry.

| Sequence | Predicted Allele |
|---|---|
| AMLDLLHVA (SEQ ID NO: 1) | HLA A*02:01 |
| RPRPSQPSSL (SEQ ID NO: 2) | HLA B*07:02 |
| IVRCIGVSL (SEQ ID NO: 3) | HLA B*07:02 |
| VPRKNITLI (SEQ ID NO: 4) | HLA B*07:02 |
| TAAEVSVRV (SEQ ID NO: 5) | HLA A*68:02 |

Example 1.3 Identified ALK-Specific Peptides Induce Immune Response In Vitro The ability of the identified peptides to induce an immune response was assessed in vitro. Cryopreserved PBMCs from ALK-positive NSCLC patients or PBMCs from healthy donors were incubated in vitro with autologous antigen presenting cells (APC) as previously described (Cai A, et al. Mutated BCR-ABL generates immunogenic T-cell epitopes in Chronic myelogenous leukemia (CML) patients (Rajasagi et al., Clin. Cancer Res. 2012; 18(20):5761-5772; Rajasagi M, et al. *Blood.* 2014; 124(3):453-462). $10\times10^6$ PBMCs were incubated in a 24-well plate with autologous dendritic cells (DCs) pulsed with 10 μM of the corresponding peptide (ratio 100:1) in a media supplemented with 10% human AB serum, rhIL7 (10 ng/ml) and rhIL2 (20 IU/ml). After 6 days, $CD8^+$ T-cells were isolated from the bulk population by magnetic beads (StemCell Technologies) and incubated with irradiated B721.221-HLA monoallele pulsed with 10 μM of the corresponding peptide (ratio 10:1). Cells were re-stimulated on days 7, 14, 21 and 28 by adding rhIL7 (10 ng/ml) and rhIL2 (20 IU/ml) on days 8, 15, 22 and 29. The specificity of the T-cells was evaluated one week after the last stimulation. T-cells were incubated with irradiated B721.221/corresponding HLA/peptide-pulsed or B721.221/corresponding HLA/EML4-ALK transduced (ratio 1:1) cells in an IFNγ-ELISPOT plate (Mabtech). As an alternative approach, T-cells were stained by dextramers that were synthesized based on the identified peptide in a complex with the corresponding HLA allele (Immunex).

Figure 4A:
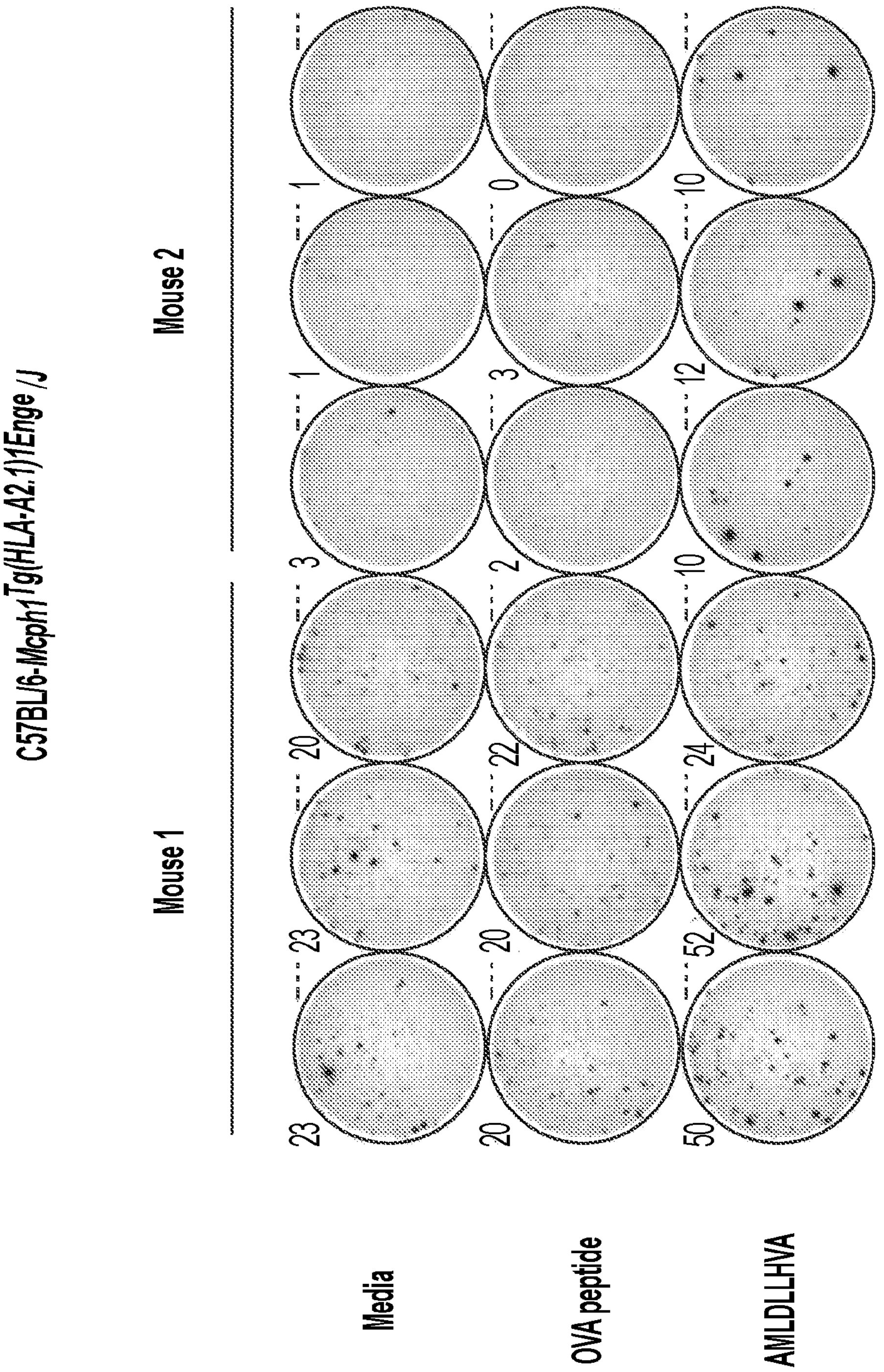
FIGS. 4A-4C depict an immune response against the HLA A*02:01-binding peptide AMLDLLHVA (SEQ ID NO: 1).
Figure 4B:
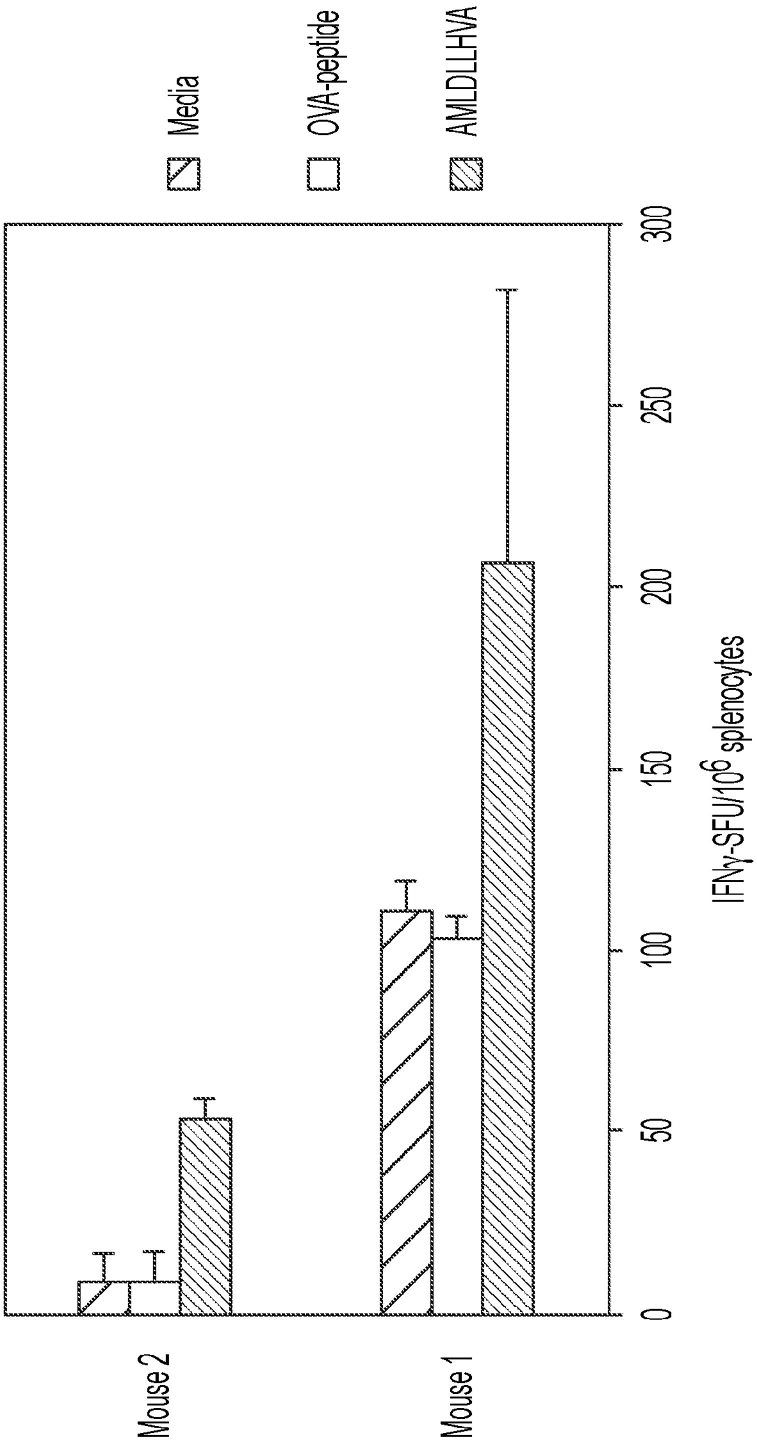
Figure 4C:
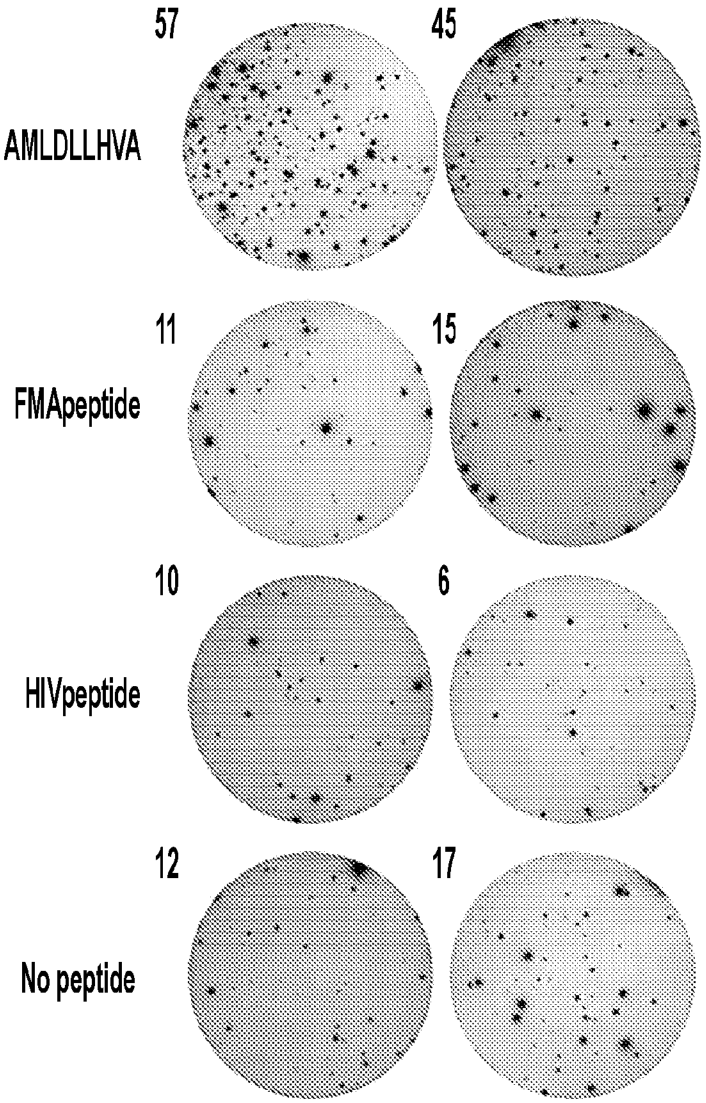

The capability of these peptides in generating T-cells responses was also assessed. HLA-A*02:01 transgenic mice (C57BL/6-Mcph1$^{Tg(HLA\text{-}A2.1)1Enge}$/J) were vaccinated with the AMLDLLHVA peptide (SEQ ID NO: 1) together with Freund's complete adjuvant. Three (3) weeks after vaccination, splenocytes from the vaccinated mice were challenged with AMLDLLHVA (SEQ ID NO: 1), OVA-peptide (negative control), and media (negative control) in an interferon-gamma (IFN-γ) ELISPOT assay (FIG. 4A). In the two (2) vaccinated mice, a 2- and 5-fold difference, respectively, was found in IFN-γ spot forming units (SFU) between wells with splenocytes challenged with AMLDLLHVA (SEQ ID NO: 1) and those wells challenged with OVA-peptide (FIG. 4B). Moreover, a direct IFN-γ-ELISPOT assay was performed by challenging PBMCs from ALK-positive NSCLC HLA A*02:01 patients with the AMLDLLHVA peptide (SEQ ID NO: 1), HIV peptide and no peptide stimulation negative controls, and flu matrix positive control (FIG. 4C). One (1) out of twenty (20) patients evaluated showed responses to this specific peptide, indicating an ALK-specific spontaneous T-cell response.

Figure 5A:
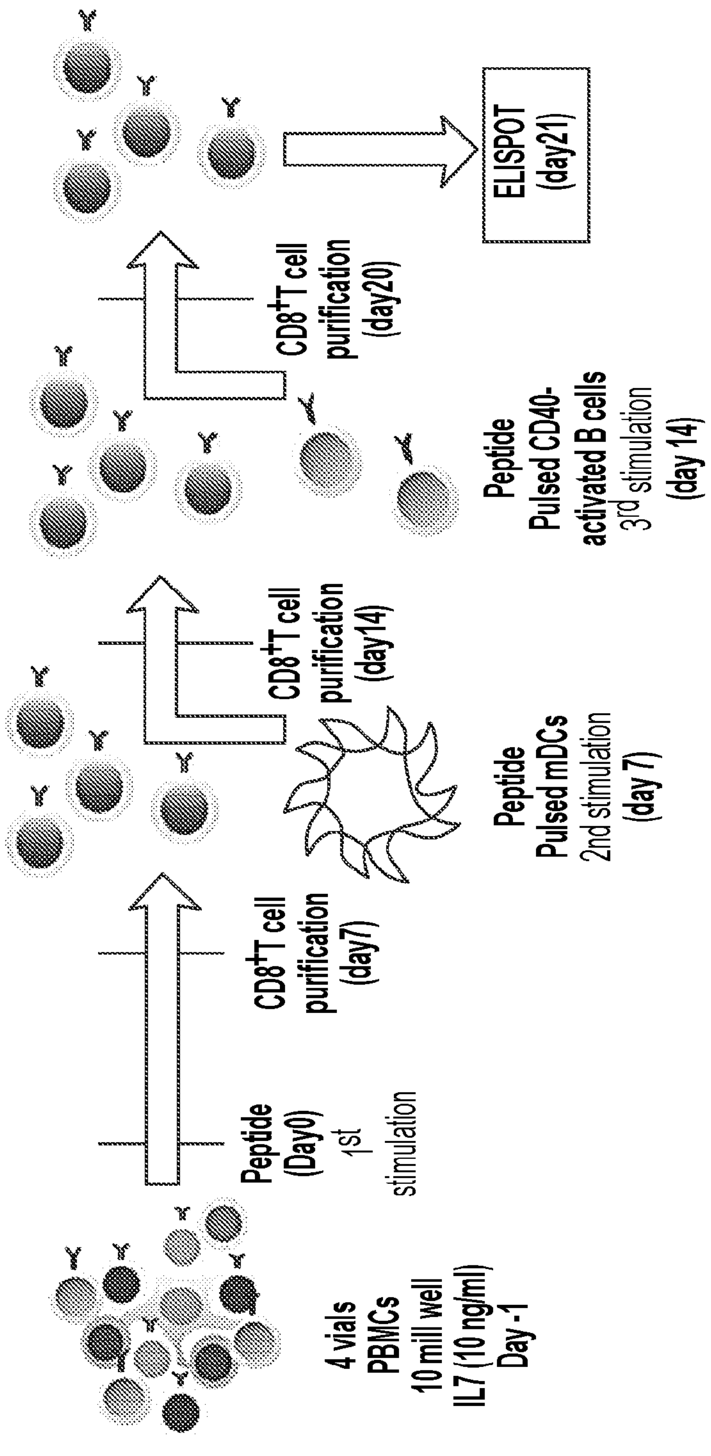
FIGS. 5A-5C depict peptide-specific $CD8^+$ T-cell expansion for ALK B*07:02 binding peptides.

For the ALK-specific HLA B*07:02 binding peptides, IVRCIGVSL (SEQ ID NO: 3) and RPRPSQPSSL (SEQ ID NO: 2), a significant response was not detected in the direct IFN-γ-ELISPOT performed with PBMCs from four (4) ALK-positive NSCLC patients. Thus, peptide-specific $CD8^+$ T-cell expansion with IVRCIGVSL (SEQ ID NO: 3) and RPRPSQPSSL (SEQ ID NO: 2) was evaluated in ALK-positive NSCLC HLA B*07:02 patient PBMCs according to the schematic in FIG. 5A. PBMCs from ALK-positive NSCLC HLA*07:02 patients were thawed and rested overnight in the presence of rh-IL-7 (10 ng/ml) at Day −1. At Day 0, PBMCs were stimulated alternatively with IVRCIGVSL (SEQ ID NO: 3) or RPRPSQPSSL (SEQ ID NO: 2). From Day 3, and every 3-4 days, fresh media containing rh-IL-2 and rh-IL-7 was added. Second and third stimulation was done by incubating purified $CD8^+$ T-cells with peptide-pulsed mature DCs (mDCs) or CD40-activated B-cells, respectively. IFN-γ ELISPOT was performed as a read out of the expansion at Day 21. HIV-pulsed and non-pulsed B-cells were used as negative controls. CEF plus-pulsed B-cells were used as positive control.

Figure 5B:
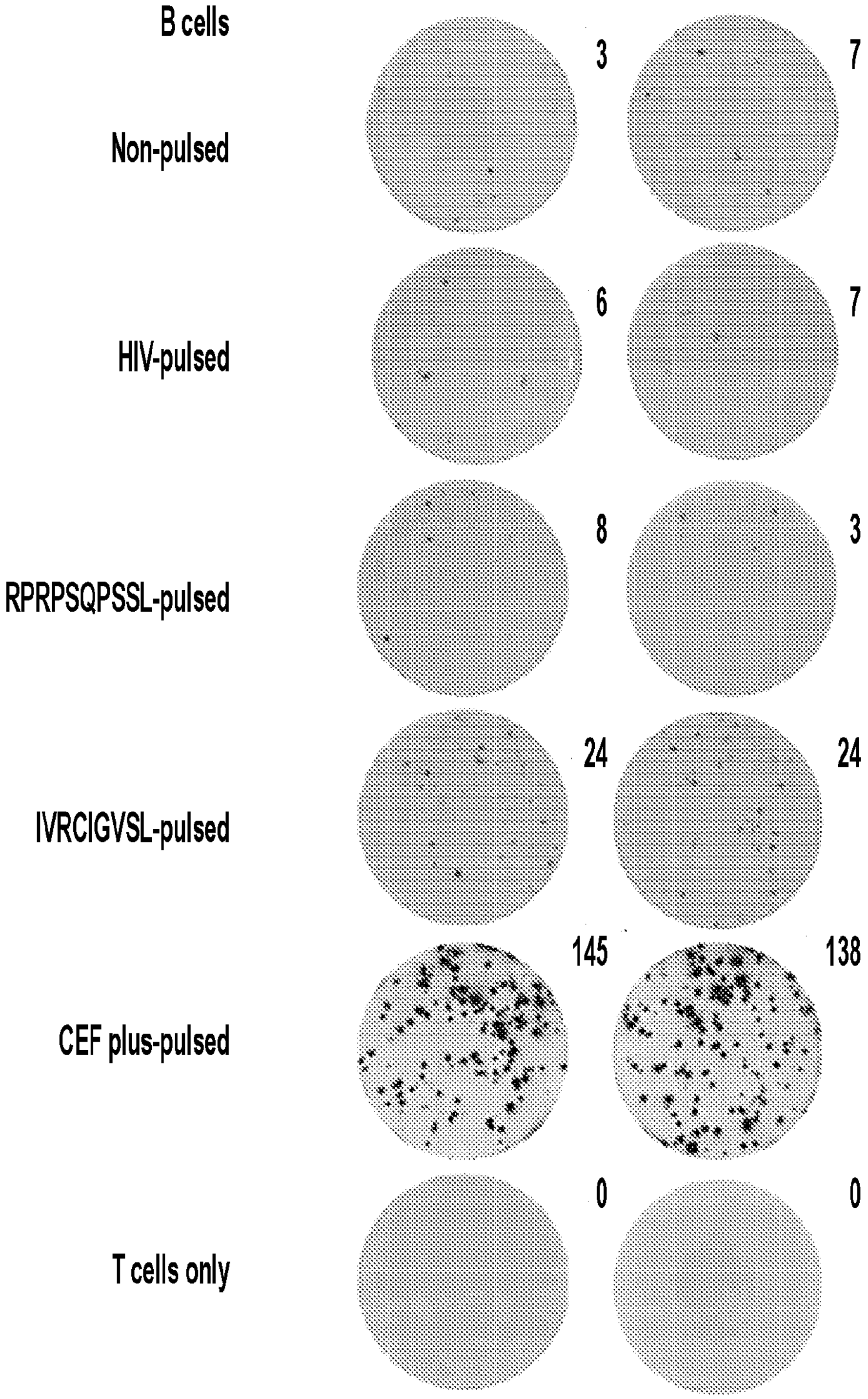
Figure 5C:
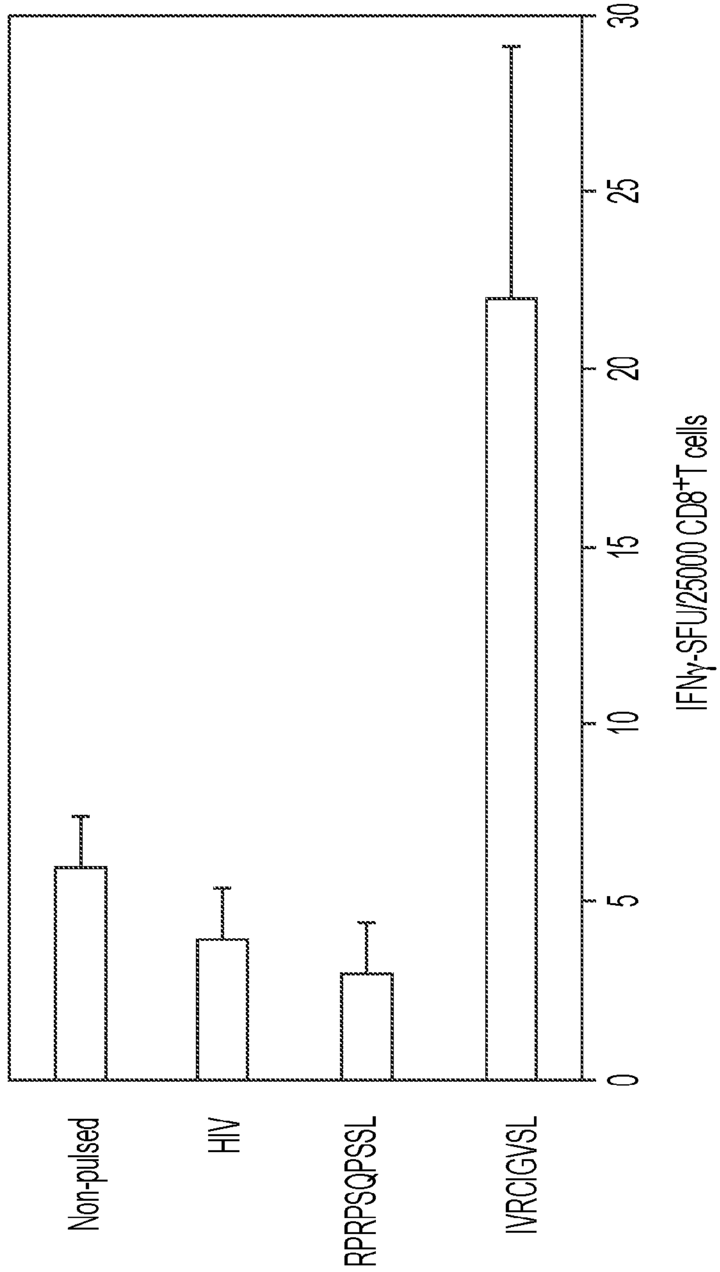

When performing an IFN-γ-ELISPOT using the IVRCIGVSL-expanded (SEQ ID NO: 3) $CD8^+$ T-cells, about four (4) times more spot forming units in wells challenged with IVRCIGVSL-pulsed (SEQ ID NO: 3) B-cells was detected compared to those wells challenged with B-cells pulsed with control peptides (FIGS. 5B and 5C). The ELISPOT was repeated twice with similar results. The same approach with the RPRPSQPSSL peptide (SEQ ID NO: 2) in PBMCs from four (4) ALK-positive NSCLC HLA B*07:02 patients did not produce significant responses.

Example 2. ALK Amphiphile Peptides

Without wishing to be bound by theory, in vitro and in vivo data suggest that amphiphile-peptide (amph-peptide) vaccines function by binding to endogenous albumin present in interstitial fluid following injection, with subsequent albumin-mediated transport to lymph nodes for efficient capture by dendritic cells (DCs) (H. Liu et al., Structure-based programming of lymph-node targeting in molecular vaccines. Nature 507, 5199522 (2014)). A schematic of this amph-peptide vaccine "albumin hitchhiking" concept is shown in FIG. 6A.

Example 2.1 ALK Peptide Selection for Amphiphile-Peptide Conjugation

In silico prediction of peptide-MHC binding is considered a reliable strategy to rank the probability of shared or neoantigens to be effectively presented on human HLA subtypes (E. F. Fritsch et al., HLA-binding properties of tumor neoepitopes in humans. Cancer Immunol Res 2, 5229529 (2014)). To determine whether conjugation with an amphiphilic tail can be applied to an ALK-specific peptide vaccine, in silico prediction and ELISpot-based screening techniques were used to identify immunogenic ALK peptides that induce strong immune responses in mouse models.

Out of twenty-eight (28) patients analyzed for HLA haplotypes, thirteen (13) patients were HLA A*02:01, eight (8) patients were HLA B*07:02, and eight (8) patients were HLA C*07:02. NetMHCpan and IEDB algorithms were used to predict which ALK peptides were most likely to be presented on HLA A*02:01, HLA B*07:02, and HLA C*07:02. The predicted ALK peptides for these three HLA haplotypes are shown in Table 4.

TABLE 4

Selection of ALK peptides for synthesis of an ALK vaccine

| NetMHCpan | nM | IEDB | Percentile Rank |
|---|---|---|---|
| HLA A*02:01 | | | |
| 9 mer | | 9 mer | |
| VLLWEIFSL (SEQ ID NO: 18) | 5 | VLLWEIFSL (SEQ ID NO: 18) | 0.3 |
| AMLDLLHVA (SEQ ID NO: 1) | 8 | FLMEALIIS (SEQ ID NO: 19) | 0.5 |
| KTDTWSFGV (SEQ ID NO: 20) | 11 | AMLDLLHVA (SEQ ID NO: 1) | 0.5 |
| FLMEALIIS (SEQ ID NO: 19) | 16 | KTDTWSFGV (SEQ ID NO: 20) | 1.1 |
| GMARDIYRA (SEQ ID NO: 21) | 77 | GMARDIYRA (SEQ ID NO: 21) | 1.2 |
| 10 mer | | 10 mer | |
| SLAMLDLLHV (SEQ ID NO: 16) | 16 | SLAMLDLLHV (SEQ ID NO: 16) | 0.4 |
| FLMEALIISK (SEQ ID NO: 22) | 35 | FLMEALIISK (SEQ ID NO: 22) | 0.55 |
| SLPRFILLEL (SEQ ID NO: 23) | 53 | SLPRFILLEL (SEQ ID NO: 23) | 1.45 |
| LLLEPSSLTA (SEQ ID NO: 24) | 71 | GVLLWEIFSL (SEQ ID NO: 25) | 1.55 |
| GVLLWEIFSL (SEQ ID NO: 25) | 93 | LLLEPSSLTA (SEQ ID NO: 24) | 1.6 |
| HLA B*07:02 | | | |
| 9 mer | | 9 mer | |
| KPTKKNNPI (SEQ ID NO: 26) | 14 | RPSQPSSLA (SEQ ID NO: 27) | 0.3 |
| RPSQPSSLA (SEQ ID NO: 27) | 16 | LPRFILLEL (SEQ ID NO: 28) | 0.5 |
| LPRFILLEL (SEQ ID NO: 28) | 18 | VPRKNITLI (SEQ ID NO: 4) | 0.5 |
| IVRCIGVSL (SEQ ID NO: 3) | 20 | KPTKKNNPI (SEQ ID NO: 26) | 1.1 |
| VPRKNITLI (SEQ ID NO: 4) | 27 | RPRPSQPSS (SEQ ID NO: 29) | 1.2 |

TABLE 4-continued

Selection of ALK peptides for synthesis of an ALK vaccine

| NetMHCpan | nM | IEDB | Percentile Rank |
|---|---|---|---|
| 10 mer | | 10 mer | |
| RPRPSQPSSL (SEQ ID NO: 2) | 7 | RPRPSQPSSL (SEQ ID NO: 2) | 0.1 |
| RPSQPSSLAM (SEQ ID NO: 30) | 14 | RPSQPSSLAM (SEQ ID NO: 30) | 0.25 |
| YPSKSNQEVL (SEQ ID NO: 31) | 55 | LPRFILLELM (SEQ ID NO: 32) | 0.3 |
| LPRFILLELM (SEQ ID NO: 32) | 60 | YPSKSNQEVL (SEQ ID NO: 31) | 0.65 |
| SPLQVAVKTL (SEQ ID NO: 33) | 85 | SPLQVAVKTL (SEQ ID NO: 33) | 0.85 |
| HLA C*07:02 | | | |
| 9 mer | | 9 mer | |
| YYRKGGCAM (SEQ ID NO: 34) | 62 | VYEGQVSGM (SEQ ID NO: 35) | 0.7 |
| YRKGGCAML (SEQ ID NO: 36) | 194 | YRKGGCAML (SEQ ID NO: 36) | 0.75 |
| VYRRKHQEL (SEQ ID NO: 37) | 225 | VYRRKHQEL (SEQ ID NO: 37) | 0.85 |
| KWMPPEAFM (SEQ ID NO: 38) | 257 | VRVPRGPAV (SEQ ID NO: 39) | 1.2 |
| GRLPGASLL (SEQ ID NO: 40) | 316 | YYRKGGCAM (SEQ ID NO: 34) | 1.35 |
| 10 mer | | 10 mer | |
| YYRKGGCAML (SEQ ID NO: 41) | 64 | YYRKGGCAML (SEQ ID NO: 41) | 0.2 |
| SYYRKGGCAM (SEQ ID NO: 42) | 145 | SYYRKGGCAM (SEQ ID NO: 42) | 0.5 |
| ERSPAAPPPL (SEQ ID NO: 43) | 429 | RRKHQELQAM (SEQ ID NO: 44) | 1.2 |
| RRKHQELQAM (SEQ ID NO: 44) | 443 | ERSAPAAPPPL (SEQ ID NO: 45) | 1.2 |
| GRLPGASLLL (SEQ ID NO: 46) | 495 | SFGVLLWEIF (SEQ ID NO: 47) | 1.3 |

Twenty-three (23) synthetic long peptides (SLP) were synthesized, each approximately thirty (30) amino acids in length (Table 5). The SLPs were synthesized to overlap with one another and span the entire region of ALK, which is translocated in human cancers. The peptides were synthesized by standard solid-phase GMP synthesis. Each peptide was purified by HPLC, and pooled and coupled through amino terminal residues with N-hydroxy succinimidyl ester-end-functionalized poly(ethylene glycol)-lipid (NHS-PEG2KDa-DSPE), forming the amphiphile-peptide conjugate, followed by size exclusion chromatography (SEC) purification.

TABLE 5

| | ALK synthetic long peptides (SLPs) |
|---|---|
| 1 | VYRRKHQELQAMQMELQSPEYKLSKLRTSTIMTDYN (SEQ ID NO: 48) |
| 2 | KLRTSTIMTDYNPNYCFAGKTSSISDLKEVPRKNIT (SEQ ID NO: 49) |
| 3 | SDLKEVPRKNITLIRGLGHGAFGEVYEGQVSGMPND (SEQ ID NO: 50) |
| 4 | VYEGQVSGMPNDPSPLQVAVKTLPEVCSEQDELDFL (SEQ ID NO: 51) |
| 5 | EVCSEQDELDFLMEALIISKFNHQNIVRCIGVSLQS (SEQ ID NO: 52) |
| 6 | NIVRCIGVSLQSLPRFILLELMAGGDLKSFLRETRP (SEQ ID NO: 53) |
| 7 | GDLKSFLRETRPRPSQPSSLAMLDLLHVARDIACGC (SEQ ID NO: 54) |
| 8 | LLHVARDIACGCQYLEENHFIHRDIAARNCLLTCPG (SEQ ID NO: 55) |
| 9 | IAARNCLLTCPGPGRVAKIGDFGMARDIYRASYYRK (SEQ ID NO: 56) |
| 10 | ARDIYRASYYRKGGCAMLPVKWMPPEAFMEGIFTSK (SEQ ID NO: 57) |
| 11 | PEAFMEGIFTSKTDTWSFGVLLWEIFSLGYMPYPSK (SEQ ID NO: 58) |
| 12 | IFSLGYMPYPSKSNQEVLEFVTSGGRMDPPKNCPGP (SEQ ID NO: 59) |
| 13 | GRMDPPKNCPGPVYRIMTQCWQHQPEDRPNFAIILE (SEQ ID NO: 60) |
| 14 | PEDRPNFAIILERIEYCTQDPDVINTALPIEYGPLV (SEQ ID NO: 61) |
| 15 | NTALPIEYGPLVEEEEKVPVRPKDPEGVPPLLVSQQ (SEQ ID NO: 62) |
| 16 | PEGVPPLLVSQQAKREEERSPAAPPPLPTTSSGKAA (SEQ ID NO: 63) |
| 17 | PPLPTTSSGKAAKKPTAAEISVRVPRGPAVEGGHVN (SEQ ID NO: 64) |
| 18 | PRGPAVEGGHVNMAFSQSNPPSELHKVHGSRNKPTS (SEQ ID NO: 65) |
| 19 | HKVHGSRNKPTSLWNPTYGSWFTEKPTKKNNPIAKK (SEQ ID NO: 66) |
| 20 | KPTKKNNPIAKKEPHDRGNLGLEGSCTVPPNVATGR (SEQ ID NO: 67) |
| 21 | SCTVPPNVATGRLPGASLLLEPSSLTANMKEVPLFR (SEQ ID NO: 68) |
| 22 | LTANMKEVPLFRLRHFPCGNVNYGYQQQGLPLEAAT (SEQ ID NO: 69) |
| 23 | GYQQQGLPLEAATAPGAGHYEDTILKSKNSMNQPGP (SEQ ID NO: 70) |

Example 2.2 ALK Amph-Peptides Elicit Protective T-Cell Responses

Figure 6B:
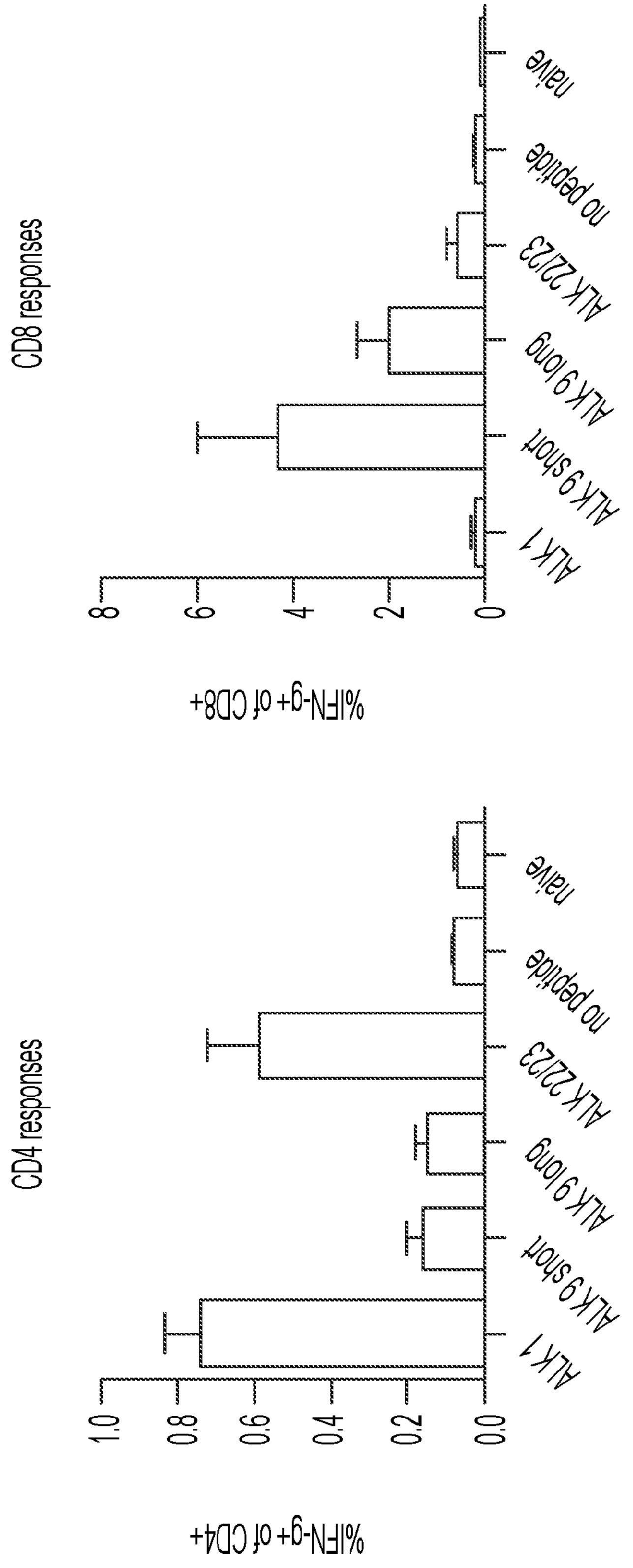
Figure 6C:
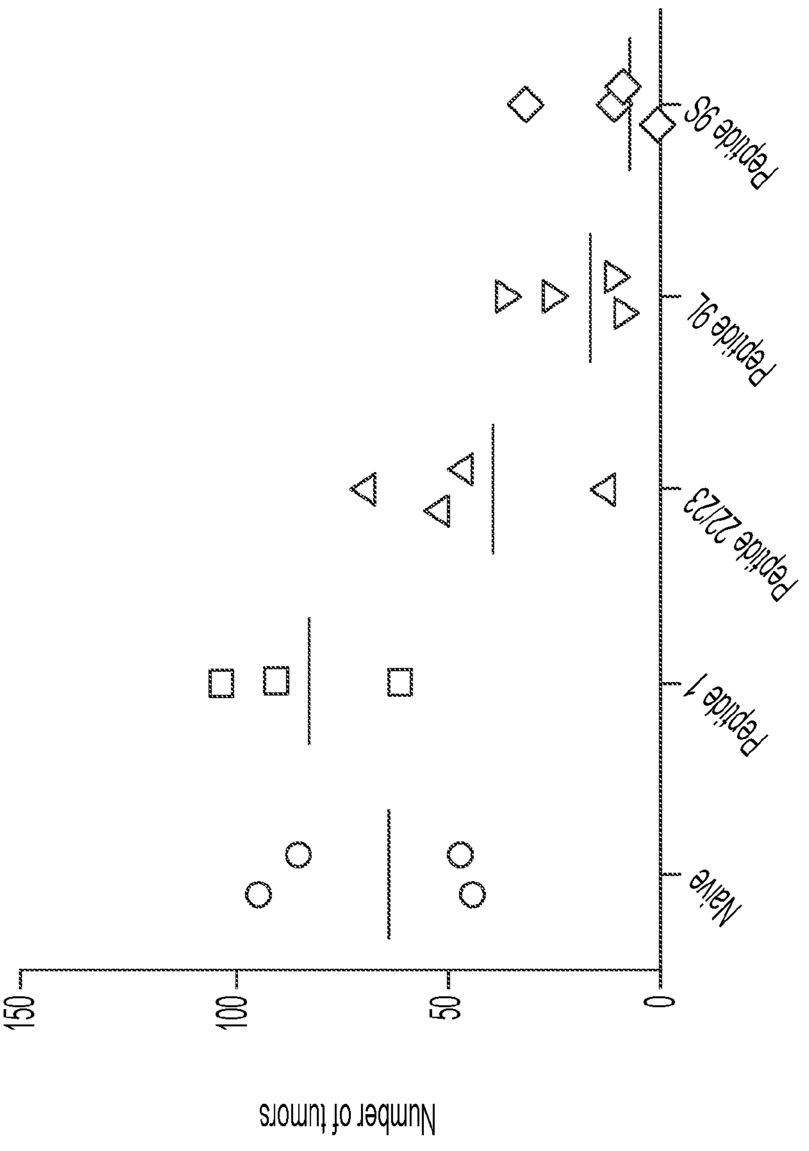

To determine whether, ALK amph-peptides elicited a T-cell response, Balb/c mice (Charles River Laboratories) were immunized with a series of different ALK amph-peptides and then assayed for ex vivo antigen-specific cytokine production. ALK amph-peptides may be generated as provided in H. Liu et al., Structure-based programming of lymph-node targeting in molecular vaccines. Nature 507, 5199522 (2014). The ALK amph-peptides assayed include: VYRRKHQEL (SEQ ID NO: 37) (ALK Peptide 1); PGPGRVAKI (SEQ ID NO: 71) (ALK Peptide 9 short); PGPGRVAKIGDFGMARDIY (SEQ ID NO: 72) (ALK Peptide 9 long); and CGNVNYGYQQQGLPLEAAT (SEQ ID NO: 73) (ALK Peptide 22/23). FIG. 6B shows that the reactive ALK sequences identified by ELISPOT are immunogenic as amph-peptides, eliciting both CD4+ and $CD8^+$ T-cell responses. Further, the number of tumors were assessed fourteen (14) days after the Balb/c mice were immunized with the different ALK peptides. Naïve peptide was used as a negative control. Mice vaccinated with ALK amph-peptides and then challenged with $ALK^+$ tumor cells were strongly resistant to the establishment of lung tumors (FIG. 6C). This data shows that compared to "naked" peptides, peptides modified with an amphiphilic conjugate significantly increased T-cell expansion and greatly enhanced anti-tumor efficacy.

Figure 7B:
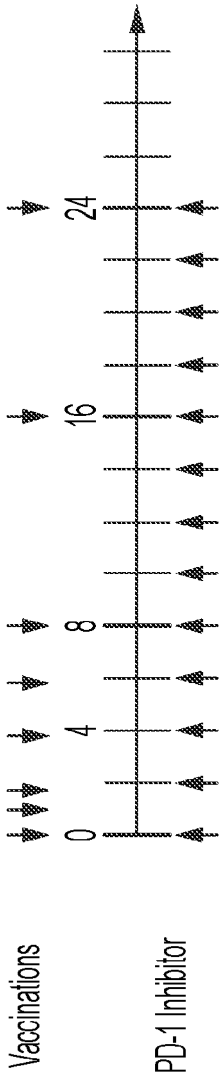

Example 3. ALK Vaccination Schedule for NSCLC Patients Harboring ALK Rearrangements In selecting patients with advanced ALK-positive NSCLC for administration of an ALK vaccine, patients were required to have progressive disease and at least one prior ALK tyrosine kinase inhibitor treatment or treatment with multiple ALK tyrosine kinase inhibitors. A washout period of three (3) weeks for standard chemotherapy or five (5) half-lives for oral tyrosine kinase inhibitors was required prior to vaccine administration. At baseline, all patients were required to undergo both blood collection to measure ALK specific autoantibodies and ALK-specific T-cell responses as well as a tumor core biopsy in order to assess for infiltrating immune cell subsets. The first portion of this study consisted of peptide administration alone. Six (6) patients (Cohort TA) received "naked" ALK peptides, and six (6) patients (Cohort 1B) received amphiphilic-conjugated peptides. Twenty (20) peptides were synthesized and pools of five (5) peptides and the adjuvant poly-ICLC, which is a synthetic complex of carboxynethylcellulose, polyinosinic-polycytidylic acid, and poly-L-lysine double-stranded RNA, were injected into four (4) different anatomic sites that drain to separate lymph node basins in order to reduce potential antigenic competition between peptides binding to the same HLA molecule. ALK vaccine was administered on days 1, 8, 15, 29, 43, and 57 with a booster vaccine at 16 and 24 weeks according to the schedule shown in FIG. 7A. Patients were assessed for dose-limiting toxicities (DLTs) for a period of six (6) weeks. Based on an analysis of safety, tolerability, efficacy, and ability to generate immunologic responses to ALK at eight (8) weeks, one of the two peptide formulations (naked or amphiphilic) was selected for use in patients for Cohort 2. In Cohort 2A, eight (8) patients received concurrent ALK peptide vaccine in combination with a commercially available PD-1 inhibitor according to the schedule as shown in FIG. 7B. In Cohort 2B, eight (8) patients initially received ALK peptide vaccine alone, and then upon disease progression, the PD-1 inhibitor was added to the treatment regimen.

Figure 8A:
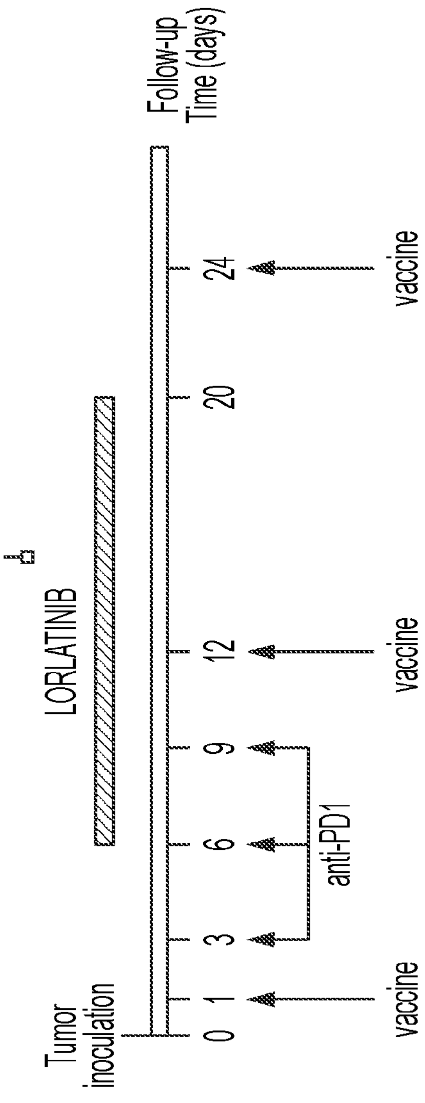
FIGS. 8A and 8B depict schematic illustrations of ALK-peptide vaccination administration in combination with ALK inhibitor therapy (lorlatinib) and immune checkpoint therapy (anti-PD-1 antibody).
Figure 8B:
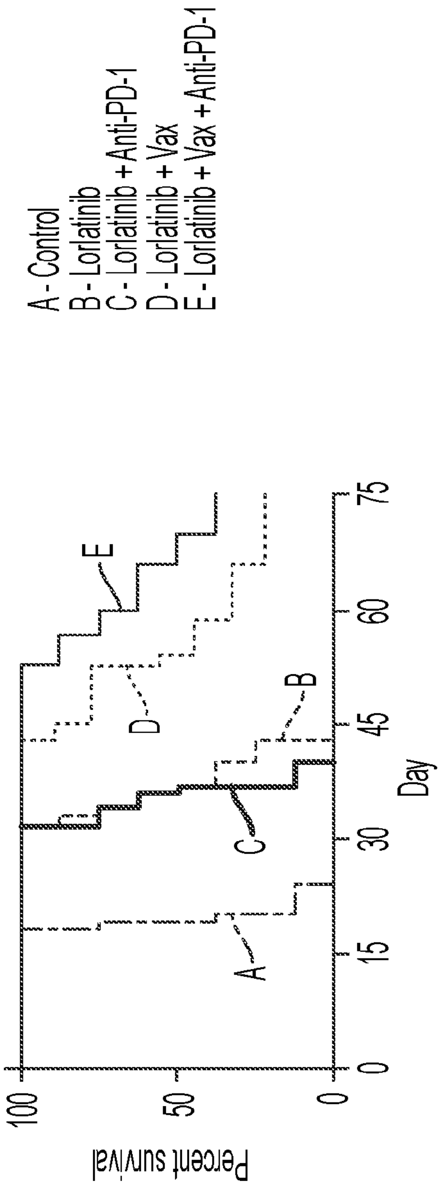

Example 4. Efficacy of ALK-Peptide Vaccine in Combination with ALK Inhibitor Therapy and Immune Checkpoint Therapy To test the efficacy of an ALK-peptide vaccine in combination with ALK inhibitor therapy and immune checkpoint therapy, a non-small cell lung cancer (NSCLC) mouse model was utilized. To perform the experiments in immunocompetent mice, EML4-ALK rearranged NSCLC cell line syngeneic to the BALB/c mouse strain was generated. These cells were further edited by CRISPR/Cas9 technology to introduce in the ALK gene a $CD8^+$ epitope specific for BALB/c mice. These NSCLC cell lines colonize the lung when injected into the tail vein and generate lung tumors. Once tumors formed in the lungs, mice were treated with either: i) the ALK-specific inhibitor, lorlatinib, for 15 days (n=9); ii) with a combination of lorlatinib and the checkpoint inhibitor, PD-1, (n=9); iii) with lorlatinib and the ALK vaccine (n=9); or iv) a combination of lorlatinib, anti-PD1 and ALK vaccine (n=8) (FIG. 8A). The control group did not receive any type of treatment (n=5). All mice injected with tumor cells that did not receive any treatment died before day 21 due to the development of multiple tumors. Lorlatinib treatment delayed tumor progression (median survival 36.5 days). Anti-PD-1 did not add any benefit to the treatment with lorlatinib (median survival 36.5 days). The addition of the ALK vaccine to lorlatinib significantly extended the survival of the mice (median survival 54 days). Adding anti-PD-1 to the ALK vaccine in combination with lorlatinib further extended survival (median survival 68 days) (FIG. 8B). Thus, the ALK vaccine, alone or in combination with anti-PD-1, significantly reduced tumor growth and extended survival of mice with ALK-positive lung tumors treated with an ALK inhibitor.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of some embodiments herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A vaccine or immunogenic composition comprising an isolated anaplastic lymphoma kinase (ALK) peptide, wherein the isolated ALK peptide: i) is an isolated fragment of the cytoplasmic portion of an ALK protein shared by cancers having an ALK rearrangement and cancers expressing the ALK protein; ii) is capable of binding a human leukocyte antigen (HLA) encoded by an HLA class 1 allele; and iii) is capable of generating an immune response against one or more ALK-positive cancers which express the ALK protein and/or have an ALK rearrangement; wherein the amino acid sequence of the peptide is RPRPSQPSSL as set forth in SEQ ID NO: 2.

2. The vaccine or immunogenic composition of claim 1, wherein the isolated peptide is conjugated to an amphiphile.

3. The vaccine or immunogenic composition of claim 2, wherein the amphiphile is N-hydroxy succinimidyl ester-end-functionalized poly(ethylene glycol)-lipid (NHS-PEG2KDa-DSPE).

4. The vaccine or immunogenic composition of claim 1, wherein the one or more ALK-positive cancers is selected from the group consisting of non-small cell lung cancer (NSCLC), anaplastic large cell lymphoma (ALCL), neuroblastoma, B-cell lymphoma, thyroid cancer, colon cancer, breast cancer, inflammatory myofibroblastic tumors (IMT), renal carcinoma, esophageal cancer, and melanoma.

5. The vaccine or immunogenic composition of claim 1, wherein the HLA class I allele that is bound by the ALK peptide is HLA A*02:01, HLA A*68:02, HLA B*07:02, or HLA C*07:02.

6. The vaccine or immunogenic composition of claim 1, wherein the ALK protein shared by cancers having an ALK rearrangement and cancers expressing the ALK protein is a full-length human ALK protein.

7. The vaccine or immunogenic composition of claim 1, wherein the ALK rearrangement is a nucleophosmin-ALK rearrangement (NPM-ALK) or an echinoderm microtubule-associate protein-like 4-ALK rearrangement (EML4-ALK).

8. A polynucleotide encoding the isolated ALK peptide of the vaccine or immunogenic composition of claim 1.

9. A vaccine or immunogenic composition comprising the polynucleotide of claim 8.

10. A method of treating an ALK-positive cancer in a subject, the method comprising administering to the subject an effective amount of the vaccine or immunogenic composition of claim 1.

11. A method of generating an immune response in a subject, the method comprising administering to the subject an effective amount of the vaccine or immunogenic composition of claim 1.

12. A kit comprising an agent for administration to a subject with one or more ALK-positive cancers, wherein the agent comprises the vaccine or immunogenic composition of claim 1.

13. The vaccine or immunogenic composition of claim 1, wherein the HLA class I allele that is bound by the ALK peptide is HLA A*68:02 or HLA B*07:02.

14. A method of treating an ALK-positive cancer or generating an immune response in a subject, the method comprising administering to the subject an effective amount of the vaccine or immunogenic composition of claim 13.

15. The vaccine or immunogenic composition of claim 1, wherein the HLA class I allele that is bound by the ALK peptide is selected from HLA A*02:01; HLA A(1)*02:01; HLA A(2)*02:01; HLA A*68:02; HLA A(2)*68:02; HLA B*07:02; HLA B(1)*07:02; HLA C*07:02; or HLA C(2)*07:02.

* * * * *